US008999656B2

(12) United States Patent
Jirström et al.

(10) Patent No.: US 8,999,656 B2
(45) Date of Patent: Apr. 7, 2015

(54) PODXL PROTEIN IN COLORECTAL CANCER

(75) Inventors: Karin Jirström, Limhamn (SE); Mathias Uhlén, Stocksund (SE); Fredrik Pontén, Uppsala (SE)

(73) Assignee: Atlas Antibodies AB, Stockholm (SE)

(*) Notice: Subject to any disclaimer, the term of this patent is extended or adjusted under 35 U.S.C. 154(b) by 0 days.

(21) Appl. No.: 13/456,354

(22) Filed: Apr. 26, 2012

(65) Prior Publication Data

US 2012/0219548 A1    Aug. 30, 2012

Related U.S. Application Data

(63) Continuation-in-part of application No. PCT/EP2010/066168, filed on Oct. 26, 2010.

(60) Provisional application No. 61/254,830, filed on Oct. 26, 2009.

(30) Foreign Application Priority Data

Oct. 26, 2009  (EP) .................................... 09174045

(51) Int. Cl.
   *G01N 33/574* (2006.01)
   *C07K 16/30* (2006.01)
(52) U.S. Cl.
   CPC ...... *G01N 33/57419* (2013.01); *C07K 16/3046* (2013.01); *G01N 2800/52* (2013.01); *G01N 2800/56* (2013.01)
(58) Field of Classification Search
   None
   See application file for complete search history.

(56) References Cited

U.S. PATENT DOCUMENTS

| | | | |
|---|---|---|---|
| 7,842,291 B1 * | 11/2010 | Ruben et al. ............... | 424/130.1 |
| 2006/0294607 A1 | 12/2006 | Fitzhugh et al. | |
| 2007/0065888 A1 | 3/2007 | Ring et al. | |
| 2009/0138977 A1 * | 5/2009 | Domon et al. .................. | 800/13 |

FOREIGN PATENT DOCUMENTS

| | | |
|---|---|---|
| WO | WO 02/102837 A2 | 12/2002 |
| WO | WO2005017530 * | 2/2005 |
| WO | WO 2007/102787 A1 | 9/2007 |
| WO | WO 2009/108932 A2 | 9/2009 |

OTHER PUBLICATIONS

Wolpin et Al., Adjuvant Treatment of Colorectal Cancer, 2007, Cancer Journal for Clinicians, vol. 57, p. 168-185.*
Brown et Al., Cox-2: A molecular target for colorectal cacner prevention, 2005, Journal of Clinical Oncology, vol. 23, p. 2840-2855.*
Ney et Al., Pdocalyxin-like protein 1 expression is useful to differentiate pancreatic ductal adenocarcinomas from adenocarcinomas of the biliary and gastrointestinal tracts, 2007, Human Pathology, vol. 38, p. 359-364.*
Somasiri et Al., Overexpression of the anti0adhesin podocalyxin is an independent predictor of breast cancer progression, 2004, Cancer Research, vol. 64, p. 5068-5073.*
Larsson, British Journal of Cancer, vol. 105, p. 666-672, 2011, published online Aug. 9, 2011.*
Wang, American Journal of Surgical Pathology, vol. 33, p. 134-141, 2009.*
Thomas, Am J. Physiol Cell Physiol, vol. 296, C505-C513, 2008.*
Andre, Journal of Clinical Oncology, vol. 27, No. 19, 2009.*
Casey et al., "Podocalyxin variants and risk of prostate cancer and tumor aggressiveness," Hum. Mol. Genet. 15:735-41 (2006).
Larrucea et al., "Expression of podocalyxin enhances the adherence, migration, and intercellular communication of cells," Exp. Cell Res. 314:2004-15 (2008).
Naishiro et al., "Morphological and transcriptional responses of untransformed intestinal epithelial cells to an oncogenic beta-catenin protein," Oncogene 24:3141-53 (2005).
Ney et al., "Podocalyxin-like protein 1 expression is useful to differentiate pancreatic ductal adenocarcinomas from adenocarcinomas of the biliary and gastrointestinal tracts," Hum. Pathol. 38:359-364 (2007).
Pasche et al., "Molecular markers in prognosis of colorectal cancer and prediction of response to treatment," Best Pract. Res. Clin. Gastroenterol. 16:331-345 (2002).
Thomas et al., "Identification, characterization and utilization of tumor cell selectin ligands in the design of colon cancer diagnostics," Biorheology 46:207-225 (2009).
Zhan et al., "Relationship between COX-2 expression and clinicopathological features of colorectal cancers," Chin. Med. J. 117:1151-1154 (2004).
International Application No. PCT/EP2010/066168, filed Oct. 26, 2010, international preliminary report on patentability, mailed May 1, 2012.
International Application No. PCT/EP2010/066168, filed Oct. 26, 2010, international search report and written opinion, mailed Dec. 6, 2010.

* cited by examiner

*Primary Examiner* — Misook Yu
*Assistant Examiner* — Michael D Allen
(74) *Attorney, Agent, or Firm* — Myers Bigel Sibley & Sajovec, P.A.

(57) ABSTRACT

The present disclosure provides a method for determining whether a mammalian subject having a colorectal cancer belongs to a first or a second group, wherein the prognosis of subjects of the first group is better than the prognosis of subjects of the second group, comprising the steps of: a) evaluating an amount of PODXL protein in at least part of a sample earlier obtained from the subject, and determining a sample value corresponding to the evaluated amount; b) comparing said sample value from step a) with a predetermined reference value; and if said sample value is higher than said reference value, c1) concluding that the subject belongs to said second group; and if said sample value is lower than or equal to said reference value, c2) concluding that the subject belongs to said first group. Related uses, means and a method of treatment are also provided.

6 Claims, 14 Drawing Sheets

PODXL PROTEIN IN COLORECTAL CANCER

This application is a Continuation-In-Part of International Patent Application No. PCT/EP2010/0066168, filed Oct. 26, 2010 which claims priority to EP09174045.6, filed Oct. 26, 2009 and U.S. Provisional Application No. 61/254,830, filed Oct. 26, 2009. The entire content of each of these applications is incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 18, 2012 is named 21041680US2_Seq list_ST25.txt and is 25,600 KB in size.

FIELD OF THE INVENTION

The present invention relates to the field of colorectal cancer prognostics and colorectal cancer treatment.

BACKGROUND OF THE INVENTION

Cancer

Cancer is one of the most common causes of disease and death in the western world. In general, incidence rates increase with age for most forms of cancer. As human populations continue to live longer, due to an increase in the general health status, cancer may affect an increasing number of individuals. The cause of most common cancer types is still largely unknown, although there is an increasing body of knowledge providing a link between environmental factors (dietary, tobacco smoke, UV radiation etc) as well as genetic factors (germ line mutations in "cancer genes" such as p53, APC, BRCA1, XP etc) and the risk of developing cancer.

No definition of cancer is entirely satisfactory from a cell biological point of view, despite the fact that cancer is essentially a cellular disease, and defined as a transformed cell population with net cell growth and anti-social behavior. Malignant transformation represents the transition to a malignant phenotype based on irreversible genetic alterations. Although this has not been formally proven, malignant transformation is believed to take place in one cell, from which a subsequently developed tumor originates (the "clonality of cancer" dogma). Carcinogenesis is the process by which cancer is generated and is generally accepted to include multiple events that ultimately lead to growth of a malignant tumor. This multi-step process includes several rate-limiting steps, such as addition of mutations and possibly also epigenetic events, leading to formation of cancer following stages of precancerous proliferation. The stepwise changes involve accumulation of errors (mutations) in vital regulatory pathways that determine cell division, asocial behavior and cell death. Each of these changes may provide a selective Darwinian growth advantage compared to surrounding cells, resulting in a net growth of the tumor cell population. A malignant tumor does not only necessarily consist of the transformed tumor cells themselves but also surrounding normal cells which act as a supportive stroma. This recruited cancer stroma consists of connective tissue, blood vessels and various other normal cells, e.g., inflammatory cells, which act in concert to supply the transformed tumor cells with signals necessary for continued tumor growth.

The most common forms of cancer arise in somatic cells and are predominantly of epithelial origin, e.g., prostate, breast, colon, urothelium and skin, followed by cancers originating from the hematopoetic lineage, e.g., leukemia and lymphoma, neuroectoderm, e.g., malignant gliomas, and soft tissue tumors, e.g., sarcomas.

Cancer Diagnostics and Prognostics

Microscopic evaluation of a tissue section taken from a tumor has for many years been the golden standard for determining a diagnosis of cancer. For example, biopsy material from suspected tumors is collected and examined under the microscope. To obtain a firm diagnosis, the tumor tissue is fixated in formalin, histo-processed and paraffin embedded. From the resulting paraffin block, tissue sections can be produced and stained using both histochemical, i.e., hematoxylin-eosin staining, and immunohistochemical (IHC) methods. The surgical specimen is then evaluated with pathology techniques, including gross and microscopic analysis. This analysis often forms the basis for assigning a specific diagnosis, i.e., classifying the tumor type and grading the degree of malignancy, of a tumor.

Malignant tumors can be categorized into several stages according to classification schemes specific for each cancer type. The most common classification system for solid tumors is the tumor-node-metastasis (TNM) staging system. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and T1-4, N1-3, M0, tumors that have metastasized to lymph nodes and T1-4, N1-3, M1, tumors with a metastasis detected in a distant organ. TNM stage I refers to T1-2, N0, M0; TNM stage II refers to T3-4, N0, M0; TNM stage III refers to T1-4, N1-2, M0; and TNM stage IV refers to any T, any N, M1. Sometimes the respective stages are divided into stage: IIA, IIB and IIC; IIIA, IIIB and IIIC; and IVA and IVB. Staging of tumors is often based on several forms of examination, including surgical, radiological and histopathological analyses. In addition to staging, for most tumor types there is also a classification system to grade the level of malignancy. The grading systems rely on morphological assessment of a tumor tissue sample and are based on the microscopic features found in a given tumor. These grading systems may be based on the degree of differentiation, proliferation and atypical appearance of the tumor cells. Examples of generally employed grading systems include Gleason grading for prostatic carcinomas and the Nottingham Histological Grade (NHG) grading for breast carcinomas.

Accurate staging and grading is often crucial for a correct diagnosis and may provide an instrument to predict a prognosis. The diagnostic and prognostic information for a specific tumor may subsequently determine an adequate therapeutic strategy for a given cancer patient. A commonly used method, in addition to histochemical staining of tissue sections, to obtain more information regarding a tumor is immunohistochemical staining. IHC allows for the detection of protein expression patterns in tissues and cells using specific antibodies. The use of IHC in clinical diagnostics allows for the detection of immunoreactivity in different cell populations, in addition to the information regarding tissue architecture and cellular morphology that is assessed from the histochemically stained tumor tissue section. IHC can be involved in supporting the accurate diagnosis, including staging and grading, of a primary tumor as well as in the diagnostics of metastases of unknown origin. The most commonly used antibodies in clinical practice today include antibodies against cell type "specific" proteins, e.g., PSA (prostate), MelanA (melanocytes) and Thyroglobulin (thyroid gland), and antibodies recognizing intermediate filaments (epithelial, mesenchymal, glial), cluster of differentiation (CD) antigens (hematopoetic, sub-classification of lympoid cells) and markers of malignant potential, e.g., Ki67 (proliferation), p53 (commonly mutated tumor suppressor gene) and HER-2 (growth factor receptor).

Aside from IHC, the use of in situ hybridization for detecting gene amplification and gene sequencing for mutation analysis are evolving technologies within cancer diagnostics. In addition, global analysis of transcripts, proteins or metabolites all add relevant information. However, most of these analyses still represent basic research and have yet to be evaluated and standardized for use in clinical medicine.

Adenocarcinomas from Colon and Rectum (Colorectal Cancer)

Colorectal cancer, a malignant epithelial tumor that presents as an adenocarcinoma, is one of the most common forms of human cancer worldwide. Data from the GLOBOCAN 2002 database presented by Parkin et al show that around 1 million new cases of colorectal cancer are identified yearly (Parkin D M et al (2005) CA Cancer J Clin 55, 74-108). Further, the world incidence of colorectal cancer is approximately 9.4% of all cancers, and colorectal cancer constitutes the second most common cause of death in the western world. The five-year survival rate of colorectal cancer is approximately 60% in the western world, but as low as 30% in Eastern Europe and India.

Early detection, and surgery with excision of the tumor, is normally of critical importance for successful treatment. For localized tumors, i.e. tumors that have not evolved into a metastasizing disease, surgical intervention with radical resection of the tumor and surrounding bowel and tissues is performed. Colorectal tumors are categorized into several stages according to Dukes' stages A-D, or more recently according to the TNM classification. Early stage tumors (Dukes' stages A and B) are generally associated with a relatively favorable outcome, while later stage tumors, presenting with metastasis (Dukes' stage C and D) have poor survival rates. Dukes' stage A, B, C and D corresponds to TNM stage I, II, III and IV, respectively.

Unfortunately, colorectal tumors have often grown to a considerable size before detection, and metastases are not uncommon. The tumor typically metastasizes to regional lymph nodes, but distant metastasis to the liver and lung are also common.

Symptoms depend on where in the distal gastrointestinal tract the tumor is located, and include bowel distress, diarrhea, constipation, pain and anemia (secondary to bleeding from the tumor into the bowel). Current diagnostics are often based on patient history, clinical and endoscopic examination (rectoscopy and colonoscopy), optionally followed by radiological mapping to determine extensiveness of tumor growth. In conjunction with endoscopic examination, tissue biopsies are performed from dubious lesions.

In differential diagnostics, cytokeratin 20 (CK20), an intermediate filament marker abundant in the glandular cells of the GI-tract, is commonly used to diagnose primary tumors in the GI-tract including colorectal cancer. The CK20 marker is not ideal as several other adenocarcinomas also can be positive for CK20 antibodies, whereas not all colorectal cancers are positive.

Today, prognostic information is mainly obtained from tumor staging classification as there are no accepted grading systems or biomarkers that provide additional prognostic data. For example, there are no available biomarkers that can distinguish tumors of low malignancy grade and low risk for developing into a metastasizing disease from highly malignant tumors with a reduced chance of survival. Thus, there is a great need for molecular markers that can be used to predict patient outcome and to guide patient management including therapeutic intervention.

Endpoint Analysis

Endpoint analysis for trials with adjuvant treatments for cancer gives important information on how the patients respond to a certain therapy. Overall survival (OS) has long been considered the standard primary endpoint. OS takes in to account time to death, irrespective of cause, e.g. if the death is due to cancer or not. Loss to follow-up is censored and regional recurrence, distant metastases, second primary colorectal cancers, and second other primary cancers are ignored.

Today, an increasing number of effective treatments available in many types of cancer have resulted in the need for surrogate endpoints to allow for a better evaluation of the effect of adjuvant treatments. Thus, the much longer follow-up required to demonstrate that adjuvant treatments improve OS is often complemented with other clinical endpoints that gives an earlier indication on how successful the treatment is.

In the present disclosure, patient cohorts were evaluated by OS analysis, however a surrogate endpoint was also considered, namely disease-free survival (DFS). Analysis of DFS includes time to any event related to the same cancer, i.e. all cancer recurrences and deaths from the same cancer are events.

BRIEF DESCRIPTION

It is an object of some aspects of the present disclosure to provide a method for establishing a colorectal cancer prognosis.

Further, it is an object of some aspects of the present disclosure to provide a method for obtaining colorectal cancer treatment-related information and/or perform colorectal cancer treatment.

Also, it is an object of some other aspects of the present disclosure to provide means for performing one or both of the above methods as well as other uses or means useful for obtaining prognostic or treatment-related information.

The following is a non-limiting and itemized listing of embodiments of the present disclosure, presented for the purpose of providing various features and combinations provided by the invention in certain of its aspects.

Items

1. Method for determining whether a mammalian subject having a colorectal cancer belongs to a first or a second group, wherein the prognosis of subjects of the first group is better than the prognosis of subjects of the second group, comprising the steps of:
   a) evaluating an amount of PODXL protein in at least part of a sample earlier obtained from the subject, and determining a sample value corresponding to the evaluated amount;
   b) comparing said sample value from step a) with a predetermined reference value; and
   if said sample value is higher than said reference value,
   c1) concluding that the subject belongs to said second group; and if said sample value is lower than or equal to said reference value,
c2) concluding that the subject belongs to said first group.

2. Method according to item 1, wherein each of the first and the second group has two subgroups, α and β, and the prognosis of subjects of the subgroup α is better than the prognosis of subjects of the subgroup β in each of the first and the second group, the method further comprising the steps of:
d) evaluating an amount of COX-2 protein in at least part of a sample earlier obtained from the subject, and determining a sample value corresponding to the evaluated amount;
e) comparing said sample value from step d) with a predetermined reference value; and
if the sample value from step d) is higher than the reference value of step e),
f1) concluding that the subject belongs to subgroup β; and
if the sample value from step d) is lower than or equal to the reference value of step e),
f2) concluding that the subject belongs to subgroup α.

3. Method according to item 2, wherein the sample of step a) and the sample of step d) is the same type of sample selected from the group consisting of tissue sample, body fluid sample, stool sample and cytology sample.

4. Method according to item 3, wherein the sample of step a) and the sample of step d) is the same sample.

5. Method for determining a prognosis for a mammalian subject having a colorectal cancer, comprising the steps of:
a) evaluating an amount of PODXL protein present in at least part of a sample earlier obtained from the subject, and determining a sample value corresponding to the evaluated amount;
b) comparing the sample value obtained in step a) with a reference value associated with a reference prognosis; and,
if said sample value is higher than said reference value,
c1) concluding that the prognosis for said subject is worse than said reference prognosis; or
if said sample value is lower than or equal to said reference value,
c2) concluding that the prognosis for said subject is better than or equal to said reference prognosis.

6. Method for determining whether a subject having a colorectal cancer is not in need of a treatment with a colorectal cancer treatment regimen, comprising the steps of:
a) evaluating an amount of PODXL protein present in at least part of a sample earlier obtained from the subject, and determining a sample value corresponding to the evaluated amount;
b) comparing the sample value obtained in step a) with a reference value; and,
if said sample value is lower than or equal to said reference value,
c) concluding that said subject is not in need of the treatment with said colorectal cancer treatment regimen.

7. Non-treatment strategy method for a subject having a colorectal cancer, comprising:
a) evaluating an amount of PODXL protein present in at least part of a sample earlier obtained from the subject, and determining a sample value corresponding to the evaluated amount;
b) comparing the sample value obtained in step a) with a reference value; and,
if said sample value is lower than or equal to said reference value,
c) refraining from treating said subject with a colorectal cancer treatment regimen.

8. Method according to item 6 or 7, wherein the colorectal cancer is COX-2 low.

9. Method of treatment of a subject having a colorectal cancer, comprising:
a) evaluating an amount of PODXL protein present in at least part of a sample from the subject and determining a sample value corresponding to the evaluated amount;
b) comparing the sample value obtained in step a) with a reference value; and, if said sample value is higher than said reference value,
c) treating said subject with a colorectal cancer treatment regimen.

10. Method according to item 9, wherein said colorectal cancer is COX-2 high.

11. Method according to any one of items 6-10, wherein said colorectal cancer treatment regimen is neo-adjuvant therapy and/or adjuvant therapy.

12. Method according to item 11, wherein said neo-adjuvant therapy is radiation therapy and said adjuvant therapy is selected from colorectal cancer chemotherapies, colorectal cancer immunotherapies, radiation therapies and combinations thereof.

13. Method according to any one of the preceding items, wherein said colorectal cancer is located in the colon.

14. Method according to any one of the preceding items, wherein said colorectal cancer is located in the sigmoideum.

15. Method according to any one of the preceding items, wherein said colorectal cancer is located in the rectum.

16. Method according to any one of the preceding items, wherein said colorectal cancer is colorectal carcinoma.

17. Method according to any one of items 1-5, wherein said prognosis is a probability of survival, such as overall survival or disease free survival.

18. Method according to item 17, wherein the probability of survival is a probability of five-year, ten-year or 15-year survival.

19. Method according to any one of the preceding items, wherein said sample is a body fluid sample, stool sample or cytology sample.

20. Method according to item 19, wherein said body fluid sample is selected from the group consisting of blood, plasma, serum, cerebral fluid, urine, semen and exudate.

21. Method according to any one of the preceding items, wherein said sample comprises cells, such as tumor cells, from said subject.

22. Method according to any one of items 1-8, wherein said sample is a tissue sample.

23. Method according to item 23, wherein said tissue sample comprises tumor cells.

24. Method according to item 24, wherein said tissue sample is derived from colon or rectum.

25. Method according to item 20, wherein said tissue sample is derived from sigmoid colon.

26. Method according to any one of items 21-25, wherein the evaluation of step a) is limited to the membranes and/or cytoplasms of cells of said sample.

27. Method according to item 26, wherein the evaluation of step a) is limited to the membranes and/or cytoplasms of tumor cells of said sample.

28. Method according to any one of the preceding items, wherein said subject is a human.

29. Method according to any one of the preceding items, wherein said reference value is a value corresponding to a predetermined amount of PODXL protein in a reference sample.

30. Method according to any preceding item, wherein the sample value of step a) is determined as being either 1, corresponding to detectable PODXL protein in the sample, or 0, corresponding to no detectable PODXL protein in the sample.

31. Method according to any preceding item, wherein the reference value of step b) corresponds to a reference sample having no detectable PODXL protein.

32. Method according to any preceding item, wherein the reference value of step b) or e) is 0.

33. Method according to any one of the preceding items, wherein said reference value is a cytoplasmic fraction, a cytoplasmic intensity, or a function of a cytoplasmic fraction and a cytoplasmic intensity.

34. Method according to item 33, wherein said reference value of b) is a weak cytoplasmic intensity.

35. Method according to item 33, wherein said reference value of b) is an absent cytoplasmic intensity.

36. Method according to item 33, wherein said reference value of b) is a cytoplasmic fraction of 60% or lower.

37. Method according to item 36, wherein said reference value of b) is a cytoplasmic fraction of 5% or lower, such as 1% or lower.

38. Method according to any one of the preceding items, wherein the amino acid sequence of the PODXL protein comprises a sequence selected from:
  i) SEQ ID NO:1; and
  ii) a sequence which is at least 85% identical to SEQ ID NO:1.

39. Method according to any one of the preceding items, wherein the amino acid sequence of the PODXL protein comprises or consists of a sequence selected from:
  i) SEQ ID NO:2 or 3; and
  ii) a sequence which is at least 85% identical to SEQ ID NO:2 or 3.

40. Method according to any one of the preceding items, wherein step a) comprises:
  aI) applying to said sample of step a) a quantifiable affinity ligand capable of selective interaction with the PODXL protein to be evaluated, said application being performed under conditions that enable binding of the affinity ligand to PODXL protein present in the sample; and
  aII) quantifying the affinity ligand bound to said sample to evaluate said amount.

41. Method according to any one of items 1-40, wherein step a) comprises:
  a1) applying to said sample or step a) a quantifiable affinity ligand capable of selective interaction with the PODXL protein to be quantified, said application being performed under conditions that enable binding of the affinity ligand to PODXL protein present in the sample;
  a2) removing non-bound affinity ligand; and
  a3) quantifying affinity ligand remaining in association with the sample to evaluate said amount.

42. Method according to item 40 or 41, wherein the quantifiable affinity ligand is selected from the group consisting of antibodies, fragments thereof and derivatives thereof.

43. Method according to item 42, wherein said quantifiable affinity ligand is obtainable by a process comprising a step of immunizing an animal with a peptide whose amino acid sequence consists of the sequence SEQ ID NO:1.

44. Method according to item 40 or 41, wherein said quantifiable affinity ligand is an oligonucleotide molecule.

45. Method according to item 40 or 41, wherein the quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

46. Method according to any one of items 40-45, wherein said quantifiable affinity ligand is capable of selective interaction with a peptide whose amino acid sequence consists of the sequence SEQ ID NO:1.

47. Method according to any one of items 40-46, wherein the quantifiable affinity ligand comprises a label selected from the group consisting of fluorescent dyes and metals, chromophoric dyes, chemiluminescent compounds and bioluminescent proteins, enzymes, radioisotopes, particles and quantum dots.

48. Method according to any one of items 40-47, in which said quantifiable affinity ligand is detected using a secondary affinity ligand capable of recognizing the quantifiable affinity ligand.

49. Method according to item 48, in which said secondary affinity ligand capable of recognizing the quantifiable affinity ligand comprises a label selected from the group consisting of fluorescent dyes and metals, chromophoric dyes, chemiluminescent compounds and bioluminescent proteins, enzymes, radioisotopes, particles and quantum dots.

50. Kit for establishing a prognosis of colorectal cancer, which comprises
  a) a quantifiable affinity ligand capable of selective interaction with a PODXL protein;
  b) reagents necessary for quantifying the amount of the quantifiable affinity ligand of a);
  c) a quantifiable affinity ligand capable of selective interaction with a COX-2 protein; and
  d) reagents necessary for quantifying the amount of the quantifiable affinity ligand of c),
  wherein the reagents of b) and d) are the same or different.

51. Kit according to item 50, in which the affinity ligand of a) and/or c) is selected from the group consisting of antibodies, fragments thereof and derivatives thereof.

52. Kit according to item 51, in which the affinity ligand of a) is obtainable by a process comprising a step of immunizing an animal with a protein whose amino acid sequence consists of the sequence SEQ ID NO:1.

53. Kit according to item 50, in which the affinity ligand of a) and/or c) is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

54. Kit according to item 50, in which the affinity ligand of a) and/or c) is an oligonucleotide molecule.

55. Kit according to any one of items 50-54, in which the affinity ligand of a) is capable of selective interaction with a PODXL protein comprising, or consisting of, a sequence selected from:
  i) SEQ ID NO:2 or 3; and
  ii) a sequence which is at least 85% identical to SEQ ID NO:2 or 3.

56. Kit according to any one of items 50-55, in which the affinity ligand of a) is capable of selective interaction with a PODXL protein comprising, or consisting of, a sequence selected from:
  i) SEQ ID NO:1; and
  ii) a sequence which is at least 85% identical to SEQ ID NO:1.

57. Kit according to any one of items 50-56, in which the affinity ligand of a) and/or c) comprises a label selected from the group consisting of fluorescent dyes and metals, chromophoric dyes, chemiluminescent compounds and bioluminescent proteins, enzymes, radioisotopes, particles and quantum dots.

58. Kit according to any one of items 50-57, in which said reagents of b) and/or d) comprise a secondary affinity ligand capable of recognizing said quantifiable affinity ligand.

59. Kit according to item 58, in which said secondary affinity ligand comprises a label selected from the group consisting of fluorescent dyes or metals, chromophoric dyes, chemiluminescent compounds and bioluminescent proteins, enzymes, radioisotopes, particles and quantum dots.

60. Kit according to any one of items 50-59, further comprising at least one reference sample for provision of a reference value.

61. Kit according to item 60, in which at least one reference sample is a tissue sample comprising no detectable PODXL protein.

62. Kit according to item 60 or 61 in which at least one reference sample comprises PODXL protein and/or at least one reference sample comprises COX-2.

63. Kit according to any one of items 60-62, in which at least one reference sample comprises an amount of PODXL protein corresponding to a weak cytoplasmic intensity.

64. Kit according to any one of items 60-62, in which at least one reference sample comprises an amount of PODXL protein corresponding to an absent cytoplasmic intensity.

65. Kit according to any one of items 60-62, in which at least one reference sample comprises an amount of PODXL protein corresponding to a cytoplasmic fraction of 60% or lower.

66. Kit according to any one of items 65, in which at least one reference sample comprises an amount of PODXL protein corresponding to a cytoplasmic fraction of 5% or lower, such as 1% or lower.

67. Kit according to any one of items 60-66, in which at least one reference sample comprises an amount of PODXL protein corresponding to a value being higher than a PODXL protein reference value.

68. Kit according to item 67, in which at least one reference sample comprises an amount of PODXL protein corresponding to a strong cytoplasmic intensity.

69. Kit according to item 67 or 68, in which at least one reference sample comprises an amount of PODXL protein corresponding to a cytoplasmic fraction of 75% or higher.

70. Kit according to any one of items 60-69 comprising:
a first reference sample comprising an amount of PODXL protein corresponding to a value (positive reference value) being higher than a reference value; and
a second reference sample comprising an amount of PODXL protein corresponding to a value (negative reference value) being lower than or equal to said reference value.

71. Kit according to any one of items 60-70, in which at least one reference sample comprises an amount of COX-2 corresponding to a value being higher than a COX-2 reference value.

72. Kit according to item 71, in which at least one reference sample comprises an amount of COX-2 corresponding to a strong cytoplasmic intensity.

73. Kit according to item 71 or 72, in which at least one reference sample comprises an amount of COX-2 protein corresponding to a cytoplasmic fraction of 75% or higher.

74. Kit according to any one of items 60-73 comprising:
a first reference sample comprising an amount of COX-2 corresponding to a value (positive reference value) being higher than a reference value; and
a second reference sample comprising an amount of COX-2 corresponding to a value (negative reference value) being lower than or equal to said reference value.

75. Kit according to any one of items 60-74, in which said reference sample(s) comprise(s) cell lines.

76. Use in vitro of a PODXL protein as a prognostic marker for colorectal cancer.

77. Use according to item 76, wherein said protein is provided in a biological sample from a subject having a colorectal cancer.

78. Use according to item 77, wherein said protein is provided in a colorectal tissue sample comprising tumor cells.

79. Use according to item 78, wherein said colorectal tissue sample is a colon sample.

80. Use according to item 79, wherein said colorectal tissue sample is a sigmoideum sample.

81. Use in vitro of a PODXL protein, or an antigenically active fragment thereof, for the selection or purification of a prognostic agent for establishing a prognosis for a mammalian subject having a colorectal cancer.

82. Use of a PODXL protein, or an antigenically active fragment thereof, as an antigen in an immunization for the production of a prognostic agent for establishing a prognosis for a mammalian subject having a colorectal cancer.

83. Use according any one of items 76-82, wherein the amino acid sequence of the PODXL protein comprises a sequence selected from:
i) SEQ ID NO:1; and
ii) a sequence which is at least 85% identical to SEQ ID NO:1.

84. Use according any one of items 76-83, wherein the amino acid sequence of the PODXL protein comprises or consists of a sequence selected from:
i) SEQ ID NO:2 or 3; and
ii) a sequence which is at least 85% identical to SEQ ID NO:2 or 3.

85. Use in vitro of an affinity ligand capable of selective interaction with a PODXL protein as a prognostic agent for colorectal cancer.

86. Use according to item 85, wherein said prognostic agent is an affinity ligand capable of selective interaction with the PODXL protein, or an antigenically active fragment thereof.

87. Use of an affinity ligand capable of selective interaction with a PODXL protein in the manufacture of a prognostic agent for in vivo establishment of a prognosis for a mammalian subject having a colorectal cancer.

88. Use according to any one of items 85-87, wherein said affinity ligand is obtainable by a process comprising a step of immunizing an animal with a peptide whose amino acid sequence consists of the sequence SEQ ID NO:1.

89. Use according to any one of items 85-88, wherein said affinity ligand is capable of selective interaction with a peptide whose amino acid sequence consists of the sequence SEQ ID NO:1.

90. Affinity ligand capable of selective interaction with a PODXL protein fragment consisting of 20 amino acids or less, such as 15 amino acids or less, and comprising an amino acid sequence selected from SEQ ID NO:10-15.

91. Affinity ligand capable of selective interaction with a PODXL protein for use in treatment of a subject having colorectal cancer.

92. Affinity ligand according to item 91, capable of selective interaction with the extracellular region SEQ ID NO:6 or 7 of the PODXL protein.

93. Affinity ligand according to item 92, capable of selective interaction with a peptide whose amino acid sequence consists of the sequence SEQ ID NO:1.

94. Affinity ligand according to any one of items 91-93, which is a monoclonal or polyclonal antibody.

95. Affinity ligand according to any one of items 91-94, wherein said colorectal cancer is colon cancer, such as sigmoid colon cancer.

96. Method of treatment of a subject having a colorectal cancer comprising the step of administrating an effective amount of an affinity ligand capable of selective interaction with the PODXL protein.

97. Method according to item 96, wherein the affinity ligand is capable of selective interaction with the extracellular region SEQ ID NO:6 or 7 of the PODXL protein.

98. Method according to item 97, wherein the affinity ligand is capable of selective interaction with a peptide whose amino acid sequence consists of the sequence SEQ ID NO:1.

99. Method according to any one of items 96-98, wherein the affinity ligand is a monoclonal or polyclonal antibody, or a fragment thereof.

100. Use of a PODXL protein, or an antigenically active fragment thereof, as an antigen in an immunization for the production of a therapeutic affinity ligand according to any one of items 90-94.

101. Use according to item 100, wherein the PODXL protein consists of the extracellular region SEQ ID NO:6 or 7 or a subsequence thereof.

BRIEF DESCRIPTION OF THE FIGURES

FIG. 3 shows the results of survival analysis of 279 subjects diagnosed with sigmoid colon cancer. Briefly, the subjects were split into two groups based on PODXL protein expression, wherein "low" represents "0" according to FIG. 1 and "high" represents "1", "2" or "3" according to FIG. 1.

"PODXL protein low" and "PODXL protein high" are as in FIG. 2. "COX-2 low" is a CF of <10% and/or an absent, weak or moderate CI. "COX-2 high" is a CF of ≥10% and a strong CI.

Figure 5B:
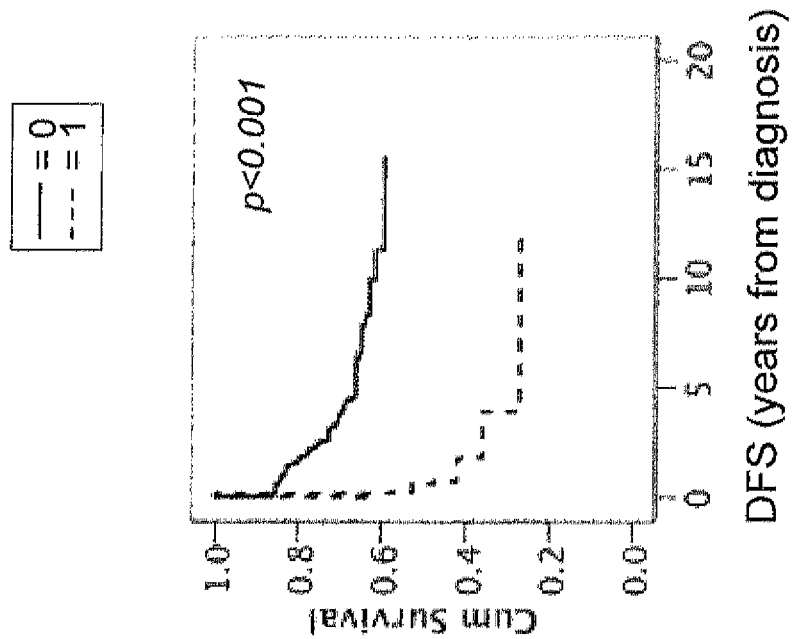
Figure 5A:
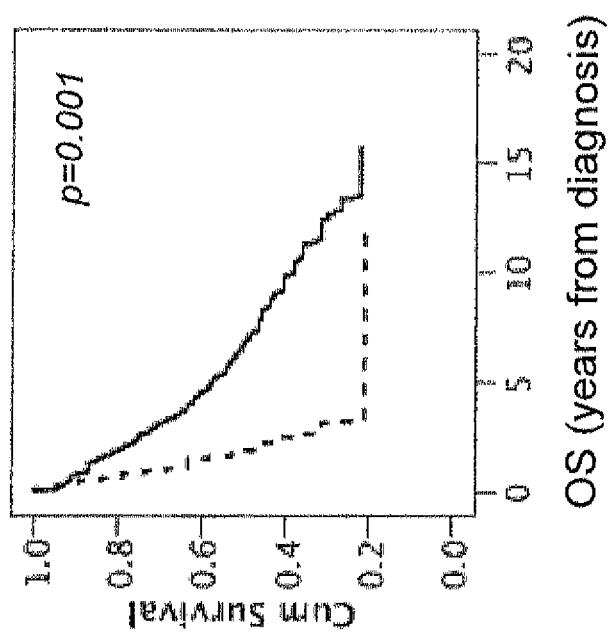

FIG. 5 shows the results of survival analysis of 279 subjects diagnosed with sigmoid colon cancer. Briefly, the subjects were split into two groups based on expression of PODXL protein and COX-2.
"0" represents subjects that are PODXL protein low and/or COX-2 low.
"1"=represents subjects that are PODXL high and COX-2 high. "PODXL protein low" and "PODXL protein high" are as in FIG. 2. "COX-2 low" is a CF of <10% and/or an absent, weak or moderate CI. "COX-2 high" is a CF of ≥10% and a strong CI. FIG. 5A shows OS and 5B shows DFS.

Figure 1B:
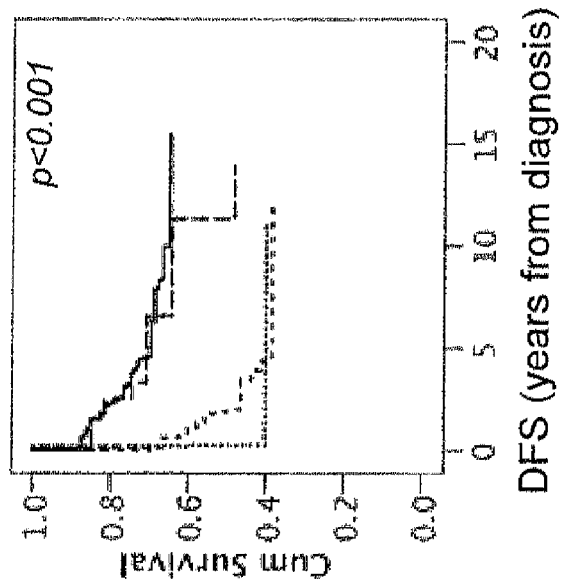
FIG. 1 shows the results of survival analysis of 279 subjects diagnosed with sigmoid colon cancer. Briefly, the subjects were split into four groups based on PODXL protein expression. "0" represents an absent cytoplasmic intensity (CI) and a cytoplasmic fraction (CF) of <1%. "1" represents a weak CI and a CF of >1%. "2" represents a moderate or strong CI and a CF of 1-50%. Finally, "3" represents moderate or strong CI and a CF of >50%.
FIG. 1A shows overall survival (OS) and 1B shows disease free survival (DFS).
Figure 1A:
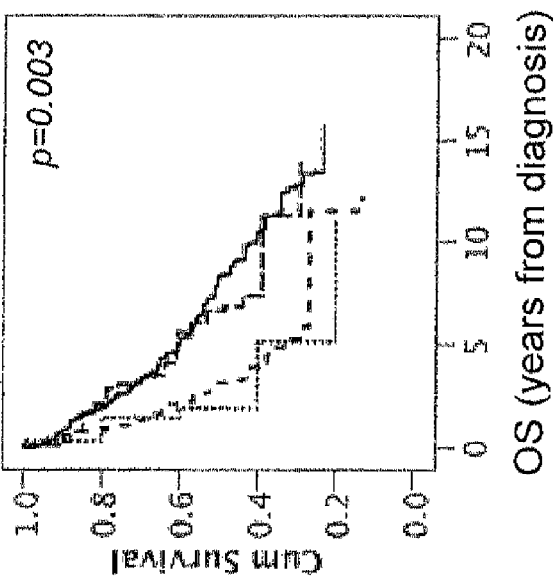
Figure 6B:
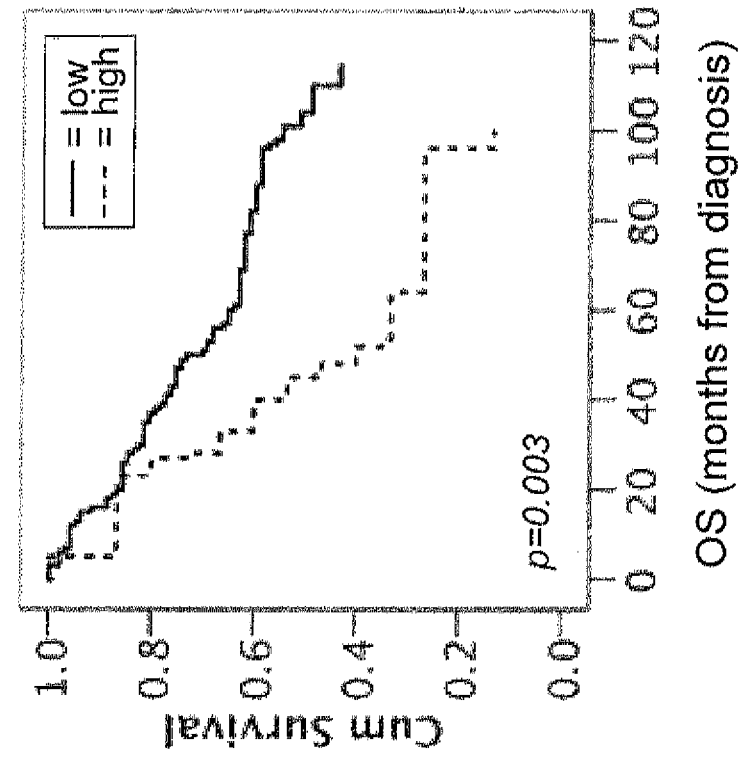
Figure 6A:
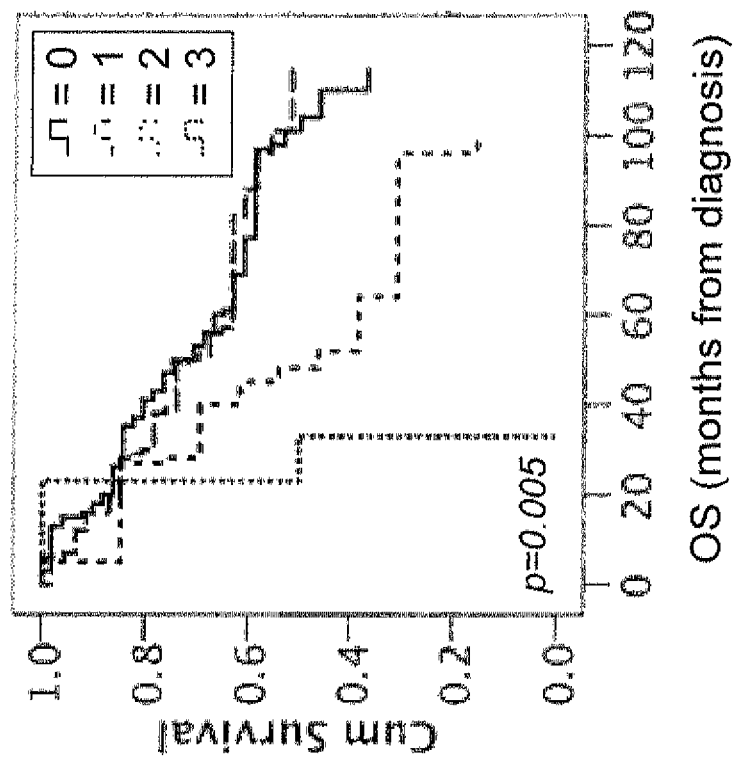

FIG. 6 shows the results of OS analysis of 112 subjects diagnosed with colorectal cancer. In FIG. 6A the subjects were split into four groups in the same way as in FIG. 1. In FIG. 6B the subjects were split into two groups in the same way as in FIG. 2.

Figure 7:
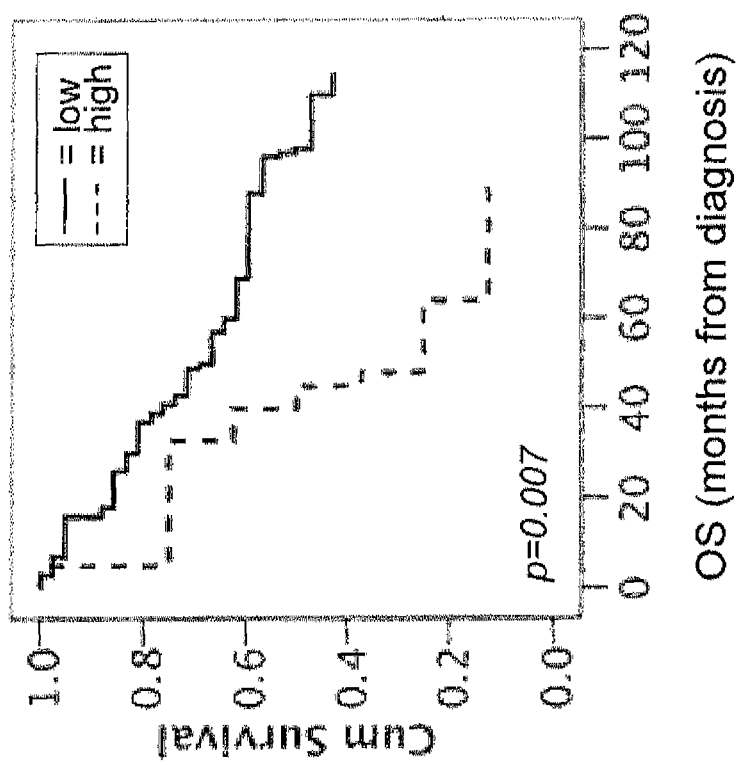

FIG. 7 shows the results of OS analysis of 50 subjects diagnosed with colon cancer. Briefly, the subjects were split into two groups in the same way as in FIG. 2.

Figure 8B:
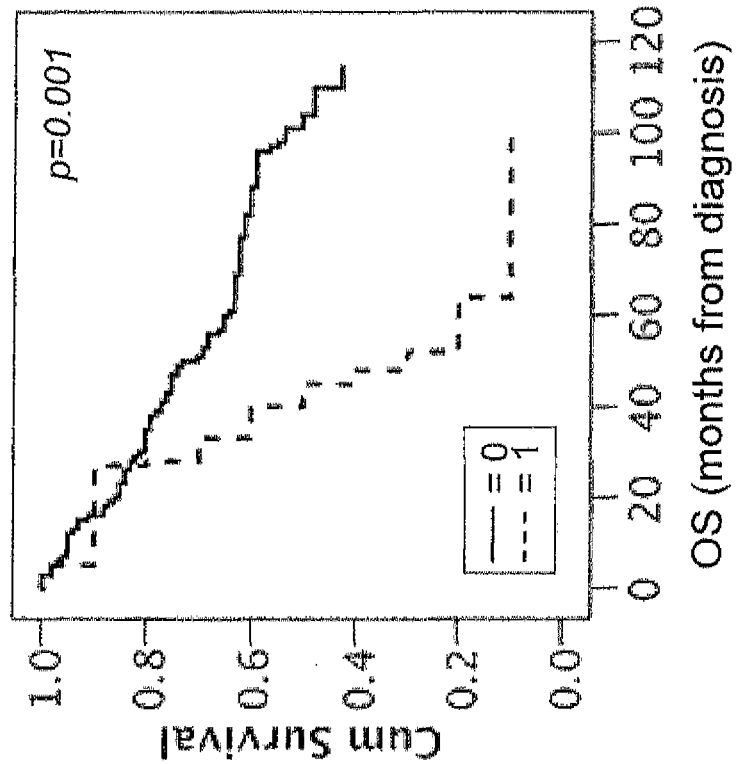
Figure 8A:
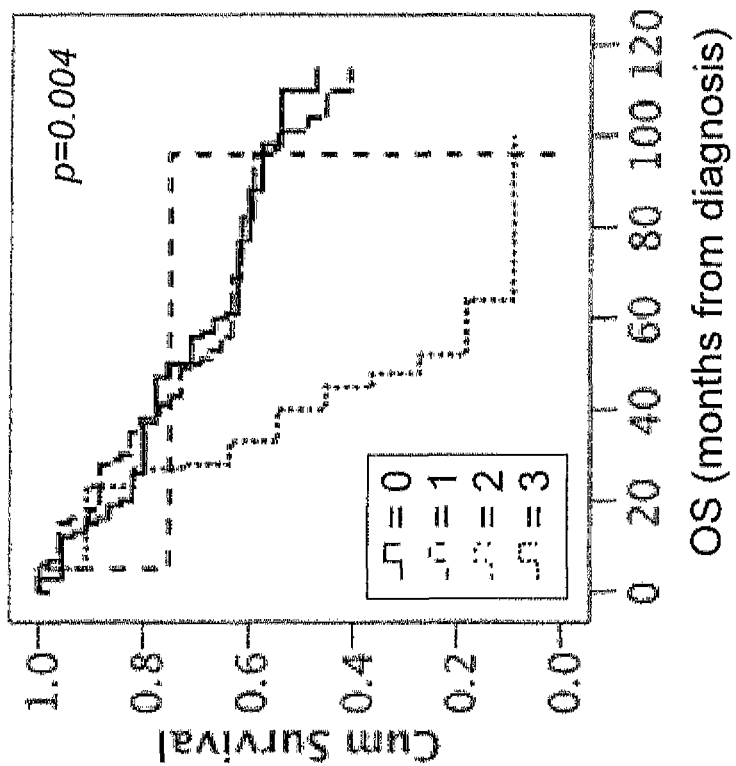

FIG. 8A shows the results of OS analysis of 112 subjects diagnosed with colorectal cancer. Briefly, the subjects were split into four groups based on expression of PODXL protein and COX-2.
"0" represents subjects that are PODXL protein low and COX-2 low.
"1" represents subjects that are PODXL protein low and COX-2 high.
"2" represents subjects that are PODXL protein high and COX-2 low. Finally,
"3" represents subjects that are PODXL protein high and COX-2 high.
"PODXL protein low" and "PODXL protein high" are as in FIG. 2. "COX-2 low" is a CF of <10% and/or an absent or weak CI. "COX-2 high" is a CF of ≥10% and a moderate or strong CI.

FIG. 8B shows the results of OS analysis of 112 subjects diagnosed with colorectal cancer. Briefly, the subjects were split into two groups based on expression of PODXL protein and COX-2. "0" represents subjects that are PODXL protein low and/or COX-2 low. "1"=represents subjects that are PODXL high and COX-2 high. "PODXL protein low" is absent or weak CI. "PODXL protein high" is moderate or strong CI. "COX-2 low" is a CF of <10% and/or an absent or weak CI. "COX-2 high" is a CF of ≥10% and a moderate or strong CI.

Figure 9B:
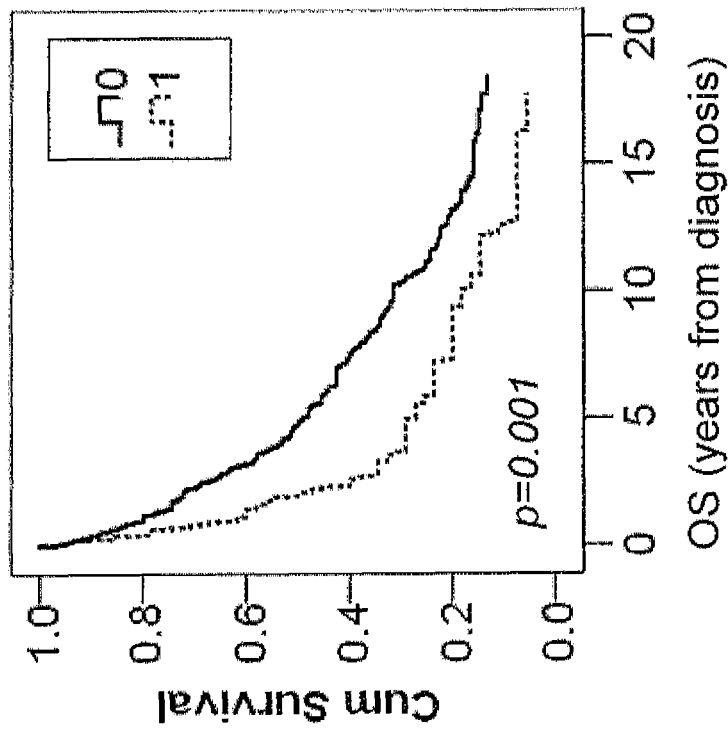
Figure 9A:
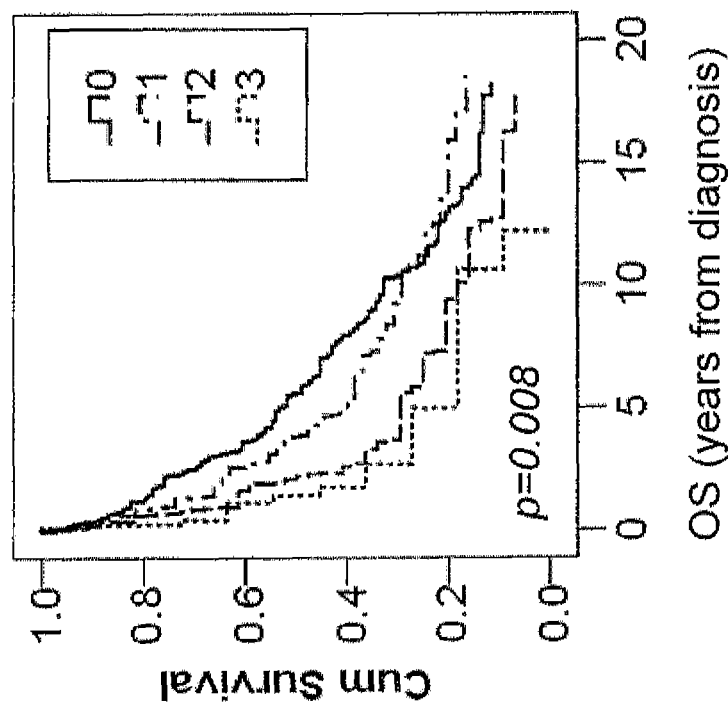

FIG. 9A shows overall survival for 270 colorectal cancer patients (colorectal cancer cohort II) with absent, weak, moderate, and strong PODXL expression (score 0 to 3) as determined by IHC analysis. "0" represents an absent cytoplasmic intensity (CI) and a cytoplasmic fraction (CF) of <1%. "1" represents a weak CI and a CF of >1%. "2" represents a moderate or strong CI and a CF of 1-50%. Finally, "3" represents moderate or strong CI and a CF of >50%.

FIG. 9B shows overall survival for the 270 colorectal cancer patients (colorectal cancer cohort II) with absent or weak PODXL expression (solid line) and moderate or high PODXL expression (dotted line). "Absent or weak" represents "0" or "1" according to FIG. 9A and "moderate or high" represents "2" or "3" according to FIG. 9A.

Figure 10B:
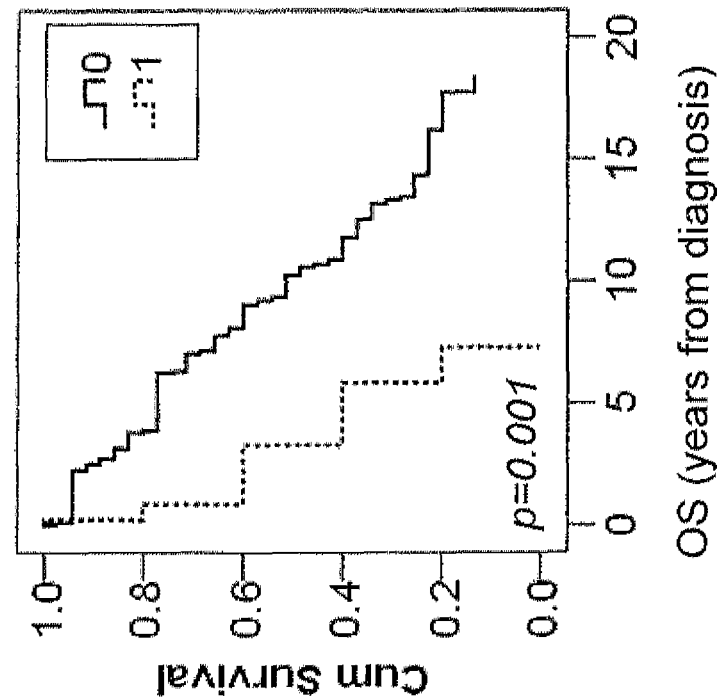
Figure 10A:
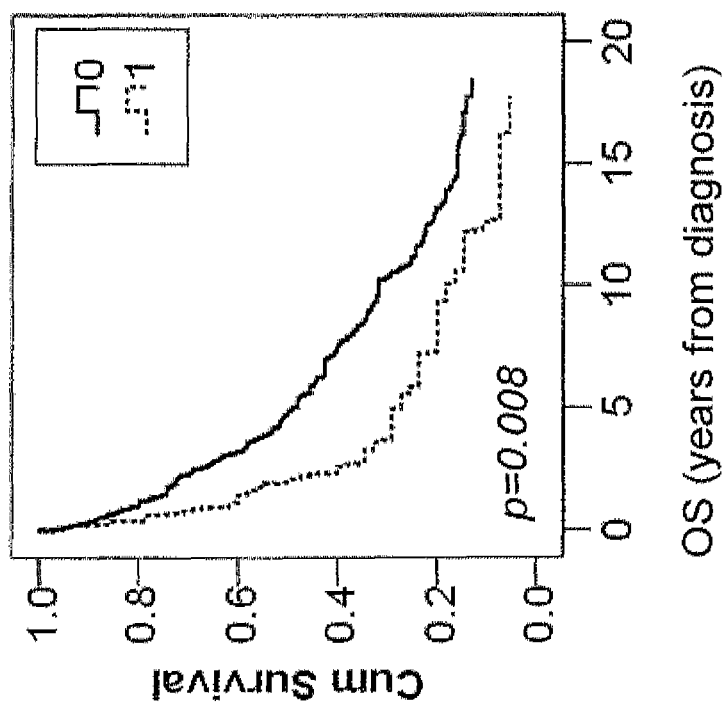

FIG. 10A shows overall survival for 21 patients from colorectal cancer cohort II with highly differentiated tumors. Briefly, the subjects were split into two groups based on PODXL protein expression. An absent PODXL expression (solid line) represents "0" according to FIG. 9A, and tumors that stained positive for PODXL (dotted line) represents "1", "2" or "3" according to FIG. 9A.

FIG. 10B shows overall survival for 42 patients from colorectal cancer cohort H with Dukes stage A tumors analyzed for PODXL expression. Briefly, the subjects were split into two groups based on PODXL protein expression. An absent or weak PODXL expression (solid line) represents "0" or "1" according to FIG. 9A and tumors that stained positive for PODXL (dotted line) represents "2" or "3" according to FIG. 9A.

Figure 11:
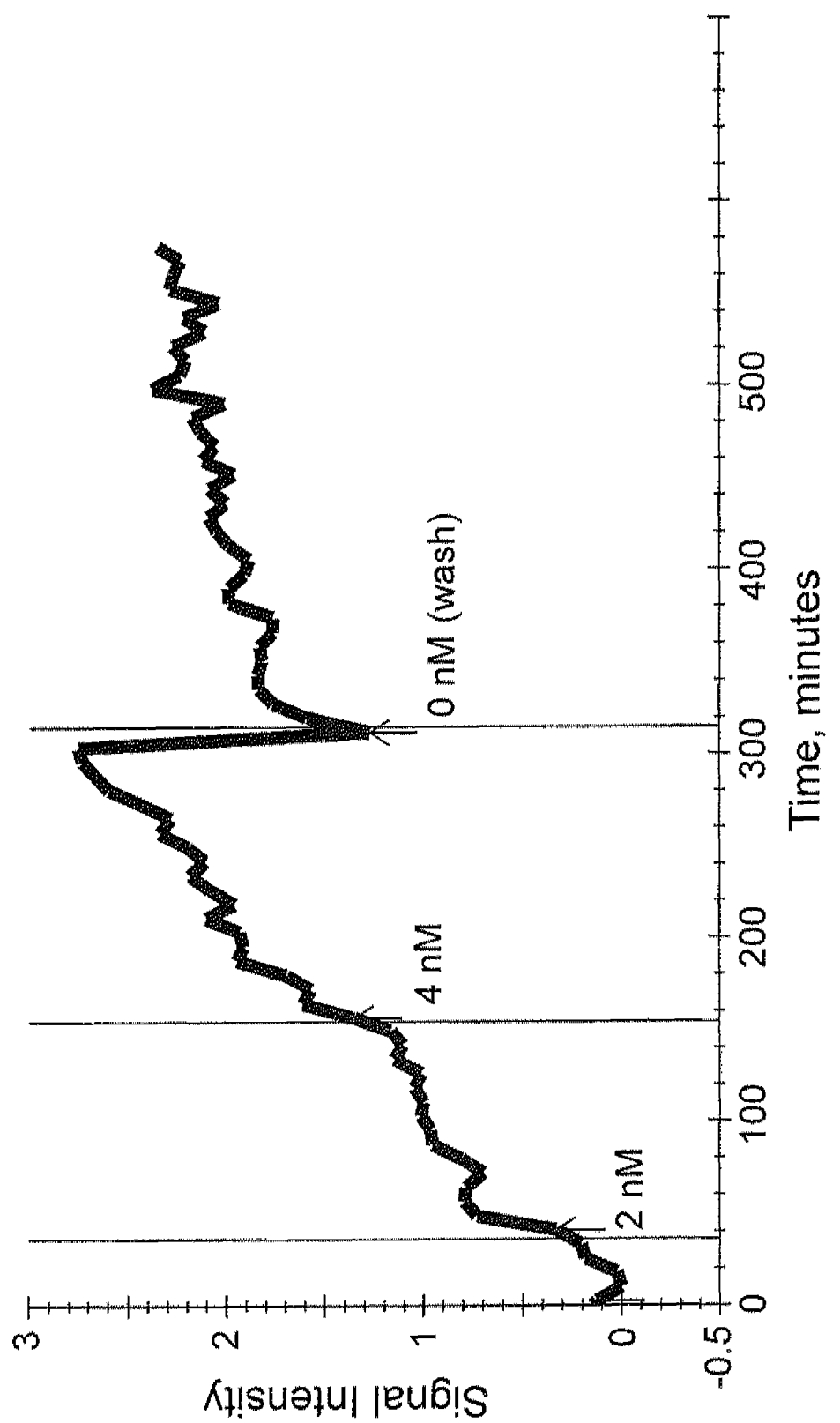

FIG. 11 shows the binding of the polyclonal anti-PODXL antibody to the surface of living human colon cancer cells in vitro. Increasing concentrations of anti-PODXL antibody was added to CACO-2 cells, indicated by vertical lines in the figure. After approximately 5 hours, also indicated by a vertical line in the figure, the anti-PODXL antibody was removed, the cells were washed and incubated with fresh complete medium only. Thus, from 5 hours on, the retention phase can be seen.

Figure 12:
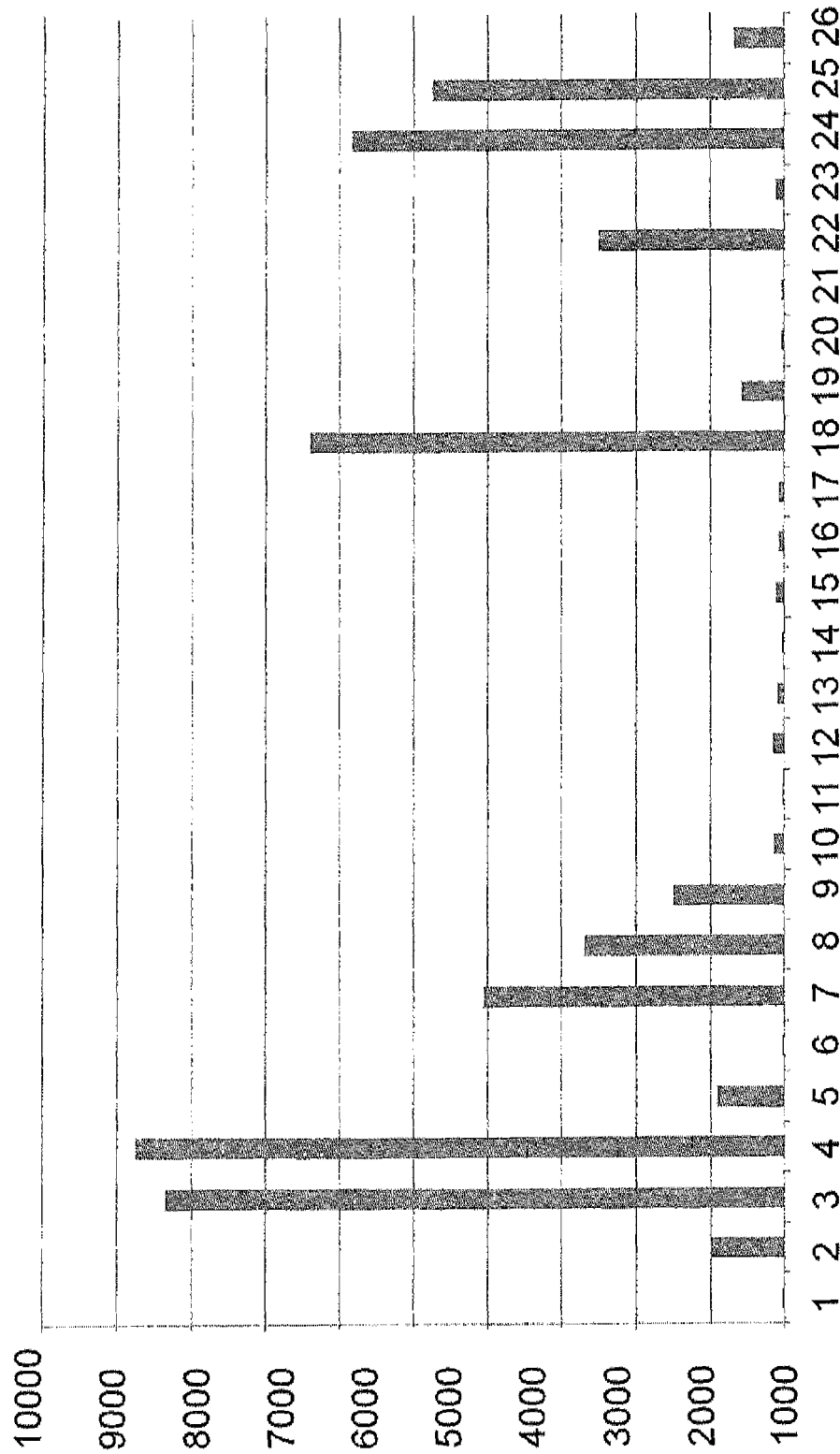

FIG. 12 shows the epitope mapping of the anti-PODXL polyclonal antibody. Antibody binding to 26 different peptides, with a length of 15 amino acids (aa) and with a 10 aa overlap, covering the entire PrEST region (SEQ ID NO:1) is shown. The y-axis represents fluorescence intensity.

Figure 13A:
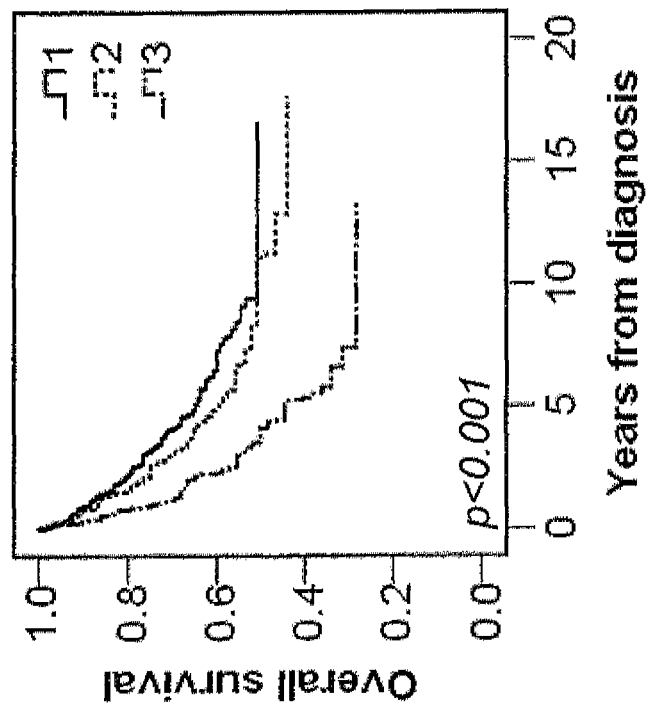
Figure 13B:
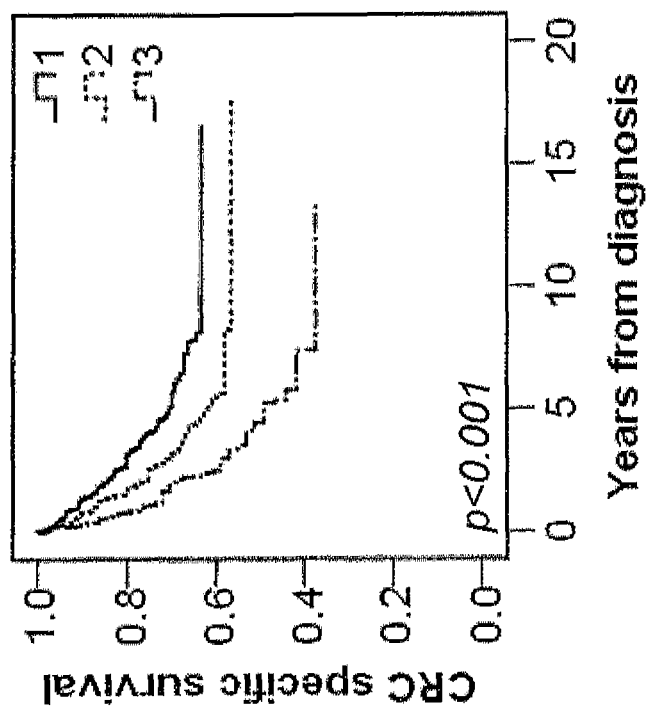

FIG. 13 shows colorectal cancer specific survival (13A) and overall survival (13B) of 536 colorectal cancer patients divided into 3 groups based on PODXL expression. Solid line ("1") represents patients with no PODXL expression (n=268), dotted line ("2") represents patients with weak or moderate PODXL expression (n=196), and intermittent line ("3") represents patients with high PODXL expression (n=72).

FIG. 14 shows impact of PODXL expression and adjuvant chemotherapy on colorectal cancer specific survival (14A) and overall survival (14B) of 122 colorectal cancer patients with curatively resected stage III disease. The line "0" represents patients with no PODXL expression that did not receive adjuvant chemotherapy, "1" represents patients with no PODXL expression that received adjuvant chemotherapy, "2" represents patients with PODXL expression that did not receive adjuvant chemotherapy, and "3" represents patients with no PODXL expression that received adjuvant chemotherapy.

DETAILED DESCRIPTION

As a first aspect of the present disclosure, there is thus provided a method for determining whether a mammalian subject having a colorectal cancer belongs to a first or a second group, wherein the prognosis of subjects of the first group is better than the prognosis of subjects of the second group, comprising the steps of:
  a) evaluating an amount of PODXL protein in at least part of a sample earlier obtained from the subject, and determining a sample value corresponding to the evaluated amount;
  b) comparing said sample value from step a) with a predetermined reference value; and
    if said sample value is higher than said reference value,
  c1) concluding that the subject belongs to said second group; and
    if said sample value is lower than or equal to said reference value,
  c2) concluding that the subject belongs to said first group.

The present aspect based on the finding that levels of PODXL protein may indicate the prognosis for a subject having colorectal cancer has a number of benefits. In general, establishing a prognosis may be of vital importance as it may help a physician selecting an appropriate treatment strategy. For example, if a cancer form of poor prognosis is identified, a painful or in any other sense unpleasant treatment, which normally is avoided, may anyway be considered. Further, if a cancer form of good prognosis can be identified, over-treatment may be avoided. As a further example, the PODXL protein, as a marker for which a certain level of expression is correlated with a certain pattern of disease progression, has a great potential, for example, in a panel for making predictions or prognoses, or for the selection of a treatment regimen.

In the method of the first aspect, it is determined whether a colorectal cancer subject belongs to a first or a second group, wherein subjects of the first group generally have a better prognosis than subjects of the second group. The division of colorectal cancer subjects into the two groups is determined by comparing samples values from the subjects with a reference value. In the present disclosure it is shown that various reference values may be employed to discriminate between subjects that generally survived for a comparatively long period, and subjects that generally survived for a comparatively short period. The reference value is thus the determinant for the size of the respective groups; the lower the reference value, the fewer the subjects in the first group and the lower the likelihood that a tested subject belongs to the first group. As the time of survival generally decreases as the PODXL expression level increases, a high reference value may in some instances be selected to identify subjects with a particularly poor prognosis. Guided by the present disclosure, the person skilled in the art may select relevant reference values without undue burden. This is further discussed below.

The first and the second group may consist exclusively of subjects having colorectal cancers of the same or similar stage, differentiation grade and/or location as the tested subject. Further, the groups may consist only of subjects having the same or similar age, race, sex, genetic (heretic) characteristics or medical status or history.

Consequently, a physician may use the method according to the first aspect to obtain additional information regarding the prognosis of a colorectal cancer subject, which in turn may help him to select the most appropriate treatment regimen. For example, a subject shown to belong to the second group using the method of the first aspect, may be given a more aggressive treatment than what would otherwise have been considered, and vice versa.

Further, the inventors have realized that an even more detailed prognosis may be obtained if the level of COX-2 protein is also measured in a sample from the subject. This is illustrated in FIGS. 4, 5 and 8 and discussed further below.

Consequently, in an embodiment of the first aspect, each of the first and the second group has two subgroups, α and β, wherein the prognosis of subjects of the subgroup α is better than the prognosis of subjects of the subgroup β in each of the first and the second group, the method further comprising the steps of:
  d) evaluating an amount of COX-2 protein in at least part of a sample earlier obtained from the subject, and determining a sample value corresponding to the evaluated amount;
  e) comparing said sample value from step d) with a predetermined reference value; and
    if the sample value from step d) is higher than the reference value of step e),
  f1) concluding that the subject belongs to subgroup β; and
    if the sample value from step d) is lower than or equal to the reference value of step e), f2) concluding that the subject belongs to subgroup α.

As seen in FIGS. 4 and 8a, subjects expressing levels of PODXL and COX-2 protein which both are higher than the reference values have a particularly poor prognosis, while subjects expressing levels of PODXL and COX-2 protein which both are lower than or equal to the reference values have a particularly good prognosis.

The prognostic information obtained by measuring the level of PODXL protein may thus be resolved further by also measuring the level of COX-2 protein.

In some embodiments, the sample of step a) and the sample of step d) may be the same type of sample selected for the group consisting of tissue sample, body fluid sample, stool sample and cytology sample. Consequently, it may be enough to collect only one type of samples from the subject, which may simplify the testing procedure and minimize uncomfortable/painful interaction with the subject's body. The sample of step a) and the sample of step d) may also be the same sample, which further simplifies the procedure and reduces discomfort/pain.

The embodiments relating to measurements of both PODXL protein and COX-2 protein apply mutatis mutandis to the configurations of the first aspect presented below as well as to the second aspect.

The prognosis of the tested subject may also be determined relative to a reference prognosis. Accordingly, as a first configuration of the first aspect, there is provided a method for determining a prognosis for a mammalian subject having a colorectal cancer, comprising the steps of:
  a) evaluating an amount of PODXL protein present in at least part of a sample earlier obtained from the subject, and determining a sample value corresponding to the evaluated amount;
  b) comparing the sample value obtained in step a) with a reference value associated with a reference prognosis; and,
    if said sample value is higher than said reference value,
  c1) concluding that the prognosis for said subject is worse than said reference prognosis; and/or
    if said sample value is lower than or equal to said reference value,
  c2) concluding that the prognosis for said subject is better than or equal to said reference prognosis.

However closely related and covered by the same concept, c1) and c2) provide two alternative conclusions.

In the present disclosure, different PODXL protein values (sample values) corresponding to various prognoses are presented. Typically, a low sample value is associated with a better prognosis than a high sample value. In the method of the first configuration of the first aspect, the sample value is compared to a reference value, and if the sample value is equal to or lower than the reference value, it is concluded that the prognosis for the subject is equal to, or better than, a reference prognosis associated with the reference value.

Consequently, the method may be adapted to a reference value. In such case, starting from a sample value which under the circumstances is considered to be relevant, a reference value which is equal to the sample value may be selected. Subsequently, a reference prognosis associated with that reference value may be established. Guided by the present disclosure, the person skilled in the art understands how to establish a reference prognosis which corresponds to a given reference value. For example, the relation between sample values and survival data in a relevant group of cancer patients may be examined in line with what is described in Examples, Section 3 or 4, below. The procedure described therein may be adapted to a given reference value. Then, a prognosis corresponding to the given reference value may be selected as the reference prognosis.

Also, the above method may be adapted to a given reference prognosis. In such case, starting from a reference prognosis which under the circumstances is considered to be relevant, for example for selecting an appropriate therapy, a corresponding reference value may be established. Guided by the present disclosure, the person skilled in the art understands how to establish a reference value which corresponds to a given reference prognosis. For example, the relation between sample values and survival data in a group of cancer patients may be examined as in Examples, Section 3 or 4, below, but the procedure described therein may be adapted to establish reference values corresponding to a given reference prognosis. For example, different reference values may be tested until one which correlates with the given reference prognosis is found.

Accordingly, the reference prognosis may be based on a previously established prognosis, e.g., obtained by an examination of a relevant population of subjects. Such reference population may be selected to match the tested subject's age, sex, race, Dukes' stage and/or medical status and history. Further, a prognosis may be adapted to a background risk in the general population, a statistical prognosis/risk or an assumption based on an examination of the subject. Such examination may also comprise the subject's age, sex, race, Dukes' cancer stage, menopausal status and/or medical status and history. Thus, a physician may for example adapt the reference prognosis to the subject's colorectal cancer history, the stage of the tumor, the morphology of the tumor, the location of the tumor, the menopausal status, the presence and spread of metastases and/or further cancer characteristics.

The inventive concept of the present disclosure may also form the basis for a decision to refrain from a certain treatment regimen.

For example, as shown in the attached figures, the prognoses for subjects showing low PODXL protein levels are generally better than those for subjects showing high PODXL protein levels. Provided with the teachings of the present disclosure, a physician may consider the prognosis of an PODXL protein low subject as being so favorable that certain adjuvant treatment regimens are avoided and a less aggressive adjuvant treatment regimen is selected instead. For example, monotherapy may be selected instead of a combination therapy or a therapeutic agent may be given in a lower dose. Also, in some cases, the decision may be to refrain from all types of adjuvant treatment. In conclusion, the present disclosure may relieve subjects from over-treatment.

Thus, as a second configuration of the first aspect, there is provided a method for determining whether a subject having a colorectal cancer is not in need of a treatment with a colorectal cancer treatment regimen, comprising the steps of:
  a) evaluating an amount of PODXL protein present in at least part of a sample earlier obtained from the subject, and determining a sample value corresponding to the evaluated amount;
  b) comparing the sample value obtained in step a) with a reference value; and,
    if said sample value is lower than or equal to said reference value,
  c) concluding that said subject is not in need of the treatment with said colorectal cancer treatment regimen.

Further, as a third configuration of the first aspect, there is provided a non-treatment strategy method for a subject having a colorectal cancer, comprising:

a) evaluating an amount of PODXL protein present in at least part of a sample earlier obtained from the subject, and determining a sample value corresponding to the evaluated amount;

b) comparing the sample value obtained in step a) with a reference value; and, if said sample value is lower than or equal to said reference value, c) refraining from treating said subject with a colorectal cancer treatment regimen.

For example, the refraining of step c) of the fifth configuration may be a refraining from treatment during at least one week from the completion of steps a)-b), such as at least one month from the completion of steps a)-b), such as at least three months from the completion of steps a)-b), such as at least six months from the completion of steps a)-b), such as at least one year from the completion of steps a)-b), such as at least two years from the completion of steps a)-b).

Alternatively, the refraining of step c) may be a refraining from treatment until the next time the method is performed or until recurrence of an colorectal cancer tumor.

As discussed above and shown in FIG. 4, subjects showing comparatively low levels of both PODXL protein and COX-2 have a particularly good prognosis and may therefore not be in need of a certain treatment.

Embodiments of the methods of the second and third configuration of the first aspect may therefore comprise COX-2 measurements (see above). Also, in embodiments of the second and third configuration of the first aspect, the subject may be COX-2 low.

"COX-2 low" refers to that a measured COX-2 level from the subject is lower than or equal to a reference level. Accordingly, "COX-2 high" refers to that a measured COX-2 level from the subject is higher than a reference level. Consequently, "COX-2 high" always corresponds to, at the least, detectable COX-2 in a relevant part of the subject's body or a relevant sample from the subject's body. For example, "COX-2 high" may be that a COX-2 sample value is higher than a reference value according to what is described in the above embodiment of the first aspect involving COX-2 evaluation. In the present disclosure, two different definitions of "COX-2 high" are employed. One definition is that a sample from the subject shows a CF of ≥10% and moderate or strong CI. An alternative definition is that a sample from the subject shows a CF of ≥10% and strong CI. If a subject is not "COX-2 high", it is "COX-2 low". In general, the cut-off used for determining whether a subject is "COX-2 high" or "COX-2 low" should be selected such that the division becomes clinically relevant. A CF of 10% (without regard to CI) may also be used as cut-off (see also Lambropoulou M et al (2009) J Cancer Res Clin Oncol, September 16). Given the teachings of the present disclosure, the skilled person understands how to discriminate between "COX-2 high" and "COX-2 low" such that relevant prognosis information is obtained.

As an alternative configuration of the first aspect, there is provided a method for establishing a prognosis for a mammalian subject having a colorectal cancer, comprising the steps of:

a) evaluating an amount of PODXL protein present in at least part of a sample from the subject, and determining a sample value corresponding to the evaluated amount; and b) correlating the sample value of step a) to the prognosis for the subject.

In the context of the present disclosure, "establishing a prognosis" refers to establishing a specific prognosis or a prognosis interval.

In an embodiment of the alternative configuration, the sample may be an earlier obtained sample.

The correlating of step b) refers to any way of associating survival data to the obtained sample value so as to establish a prognosis for the subject.

In general, when deciding on a suitable treatment strategy for a patient having colorectal cancer, the physician responsible for the treatment may take several parameters into account, such as the result of an immunohistochemical evaluation, patient age, tumor type, stage and grade, general condition and medical history, such as colorectal cancer history. To be guided in the decision, the physician may perform a PODXL protein test, or order a PODXL protein test to be performed, according to the first aspect. Further, the physician may assign to someone else, such as laboratory staff, to perform step a), and optionally step b), while performing step c), and optionally b), himself.

The inventive concept of the present disclosure may also form the basis for applying various treatment regimes.

For example, as shown in the attached figures, the prognoses for subjects showing high PODXL protein levels are generally worse than those for subjects showing low PODXL protein levels. Provided the teachings of the present disclosure, a physician may thus consider the prognosis of a PODXL protein high subject as being so poor that a certain adjuvant treatment regimen is appropriate. If the subject is also COX2 high, the indications in favor of the treatment may be even stronger. The present disclosure may thus provide for accurate treatment of a previously undertreated group.

As a second aspect of the present disclosure, there is thus provided a method of treatment of a subject having a colorectal cancer, comprising:

a) evaluating an amount of PODXL protein present in at least part of a sample from the subject and determining a sample value corresponding to the evaluated amount;

b) comparing the sample value obtained in step a) with a reference value;

and, if said sample value is higher than said reference value, c) treating said subject with a colorectal cancer treatment regimen.

According to one embodiment, the method may comprise the additional step:

d) and if said sample value is lower than or equal to said reference value, refraining from treating said subject with the colorectal cancer treatment regimen.

In one embodiment of the second aspect, the reference value of step b) may be associated with a reference prognosis and said treatment regimen of step c) may be adapted to a prognosis which is worse than the reference prognosis. In such an embodiment of the second aspect, the method may comprise the additional step: d) and if said sample value is lower than or equal to said reference value, treating said subject with a treatment regimen adapted to a prognosis which is better than or equal to the reference prognosis, for which the appropriate treatment regimen may be no treatment.

Embodiments of the second aspect may for example comprise COX-2 measurements (see above). Also, in embodiments of the second aspect, the subject may be COX-2 high.

The treatment of step c) may for example be a more comprehensive treatment than what would have been standard under the conditions if no PODXL protein or COX-2 information was available.

A subject may have a colorectal cancer in such an advanced stage that an adjuvant therapy would normally be considered superfluous and unnecessary painful. However, in such case, a physician may anyway decide to apply the adjuvant therapy if the subject in question has an increased probability of prolonged survival due to a low PODXL protein (and optionally COX-2) value.

Thus, as a first configuration of the second aspect, there is provided a method of treatment of a subject having a colorectal cancer of an advanced stage, such as Dukes' stage C or D, comprising:
a) evaluating the amount of PODXL protein present in at least part of a sample from the subject, and determining a sample value corresponding to said evaluated amount;
b) comparing the sample value obtained in step b) with a reference value; and,
if said sample value is lower than or equal to said reference value,
c) treating said subject with a colorectal cancer treatment regimen for prolonged survival.

Further, if said sample value is higher than reference value, the subject may be treated with palliative treatment only.

The physician responsible for the treatment according to the second aspect may assign to someone else, such as a laboratory staff, to perform step a), and optionally step b), while performing step c), and optionally step b), himself.

The method of treatment may be limited to the decision-making and treatment. Thus, as an alternative configuration of the second aspect, there is provided a method of treatment of a subject having a colorectal cancer, comprising:
α) comparing a sample value corresponding to a level of PODXL protein in a sample from the subject with a reference value; and,
if said sample value is higher than said reference value,
β) treating said subject with an adjuvant colorectal cancer treatment regimen.

Numerous ways of obtaining a sample value corresponding to a level of PODXL protein in a sample from a subject are described in the present disclosure.

Regarding step a) of the methods of the present disclosure, an increase in the amount of PODXL protein typically results in an increase in the sample value, and not the other way around. However, in some embodiments, the evaluated amount may correspond to any of a predetermined number of discrete sample values. In such embodiments, a first amount and a second, increased, amount may correspond to the same sample value. In any case, an increase in the amount of PODXL protein will not result in a decrease in the sample value in the context of the present disclosure.

However inconvenient, but in an equivalent fashion, the evaluated amounts may be inversely related to sample values if the qualification between step b) and c) is inverted. For example, the qualification between step b) and c) is inverted if the phrase "if the sample value is higher than the reference value" is replaced with "if the sample value is lower than the reference value".

In the context of the present disclosure, "prognosis" refers to the prediction of the course or outcome of a disease and its treatment. For example, prognosis may also refer to a determination of chance of survival or recovery from a disease, as well as to a prediction of the expected survival time of a subject. A prognosis may specifically involve establishing the likelihood for survival of a subject during a period of time into the future, such as three years, five years, ten years or any other period of time. A prognosis may further be represented by a single value or a range of values.

Further, in the context of the methods of the present disclosure, "earlier obtained" refers to obtained before the method is performed. Consequently, if a sample earlier obtained from a subject used in a method, the method does not involve obtaining the sample from the subject, i.e., the sample was previously obtained from the subject in a step separate from the method.

All the methods and uses of the present disclosure, except the methods of treatment, may be carried out entirely in vitro unless otherwise indicated.

Further, in the context of the present disclosure, "a mammalian subject having a colorectal cancer" refers to a mammalian subject having a primary or secondary colorectal tumor or a mammalian subject which has had a tumor removed from the colon and/or rectum, wherein the removal of the tumor refers to killing or removing the tumor by any appropriate type of surgery or therapy. In the method and use aspects of the present disclosure, "a mammalian subject having a colorectal cancer" also includes the cases wherein the mammalian subject is suspected of having a colorectal at the time of the performance of the use or method and the colorectal cancer diagnosis is established later.

Thus, a subject having a colorectal cancer located in the colon, may refer to a subject who has had a tumor removed from the colon.

Further, in the context of the present disclosure, the "reference value" refers to a predetermined value found to be relevant for making decisions or drawing conclusions regarding the prognosis or a suitable treatment strategy for the subject.

Also, in the context of the present disclosure, a reference value being "associated" with a reference prognosis refers to the reference value being assigned a corresponding reference prognosis, based on empirical data and/or clinically relevant assumptions. For example, the reference value may be the average PODXL protein value in a relevant group of subjects and the reference prognosis may be an average survival in the same group. Further, the reference value does not have to be assigned to a reference prognosis directly derived from prognosis data of a group of subjects exhibiting the reference value. The reference prognosis may for example correspond to the prognosis for subjects exhibiting the reference value or lower. That is, if the reference value is 1 on a scale from 0 to 2, the reference prognosis may be the prognosis of the subjects exhibiting the values 0 or 1. Consequently, the reference prognosis may also be adapted to the nature of the available data. As further discussed above, the reference prognosis may be further adapted to other parameters as well.

Step a) of the methods of the above aspects involve evaluating the amount of PODXL protein present in at least part of the sample, and determining a sample value corresponding to the amount. The "at least part of the sample" refers to a relevant part or relevant parts of the sample for establishing the prognosis or drawing conclusions regarding suitable treatments. The person skilled in the art understands which part or parts that are relevant under the circumstances present when performing the method. For example, if evaluating a sample comprising cells, the skilled person may only consider the tumor cells, or only the membranes of tumor cells, of the sample.

Further, in step a) an amount is evaluated and a sample value corresponding to the amount is determined. Consequently, an exact measurement of the amount of PODXL protein is not required for obtaining the sample value. For example, the amount of PODXL protein may be evaluated by visual inspection of a stained tissue sample and the sample value may then be categorized as e.g. high or low based on the evaluated amount.

The evaluation and determination of step a) requires some kind of processing or manipulation of the sample. It is not possible to determine the sample value by mere inspection.

Various techniques, of which some are presented below, for such evaluation and determination, are well known to the skilled person. The methods of the present disclosure are therefore not limited to any specific technique or techniques for the performance of step a).

The treatment regimen of the first and second aspect may for example be an adjuvant and/or a neo-adjuvant therapy. The neo-adjuvant therapy may for example be radiation therapy, especially in cases of rectal cancer. Appropriate adjuvant therapies are primarily chemotherapies and immunotherapies. Further, the adjuvant treatment may be chemotherapy and/or immunotherapy in combination with radiation therapy.

The general strategy is that a more comprehensive treatment is applied if a subject is found to be PODXL protein high than if the subject is found to be PODXL protein low.

For example, if the subject has a Dukes' stage B colorectal cancer, the adjuvant treatment regimen may be chemotherapy. That means that according to some of the above methods, a chemotherapeutic agent is administered to the subject if the subject is PODXL protein high (and optionally COX-2 high). However, if the subject is PODXL protein low (and optionally COX-2 low), the treatment with the chemotherapeutic agent may be considered unnecessary, and therefore, not administered to the subject.

As another example, if the subject has a Dukes' stage C colorectal cancer, the treatment regimen may be a combination of two or more chemotherapeutic agents. That means that according to some of the above methods, the combination is administered to the subject if the subject is PODXL protein high (and optionally COX-2 high). However, if the subject is PODXL protein low (and optionally COX-2 low), the combination may be considered unnecessary, and therefore, not applied to the subject. In the latter case, treatment with one therapeutic agent may be considered necessary.

Alternatively, the combination is applied in both cases, however in a relatively high dose if the subject is PODXL protein high and in a relatively low dose if the subject is PODXL protein low. Here, the "relatively high dose" is high relative to the "relatively low dose". For example, a dose considered to be normal within the art may be decreased if a sample value from the subject is lower than or equal to the reference value and increased if the sample value from the subject is higher than the reference value.

Non-limiting examples of chemotherapeutic agents are 5-fluorouracil (5-FU), capecitabine (Xeloda®) and oxaliplatin (Eloxatin®). 5-fluorouracil, capecitabine and oxaliplatin are today given as adjuvant after surgery, either alone, e.g. 5-fluorouracil, or in combinations e.g. as FOLFOX, including 5-fluorouracil, leucovorin and oxaliplatin. These drugs are also used to treat metastatic disease, but then often in combination and/or with other chemotherapeutic agents including tegafur-uracil (UFT®), leucovorin (folonic acid) and/or irinotecan (Camptosar®).

Non-limiting examples of immunotherapeutic agents are bevacizumab (Avastin®) and cetuximab (Erbitux®).

Another example of an immunotherapy that may be applied is discussed below in connection with the eighth and ninth aspect of the present disclosure. The immunotherapy may thus be application of an affinity ligand capable of selective interaction with the PODXL protein. Various embodiments of such an affinity ligand is discussed below in connection with the eighth aspect.

The treatment regimen of the first and second aspect may also comprise or consist of COX-2 inhibition treatment. This embodiment is particularly relevant when the subject is both PODXL protein high and COX-2 high.

In embodiments of the first and second aspect, the prognosis may be a probability of survival and the reference prognosis may be a reference probability of survival, wherein both survivals are the same type of survival. As explained in the background section, there are several ways to measure "survival". The survivals of the first and second aspects may for example be recurrence free survivals, overall survivals or disease free survivals. Further, the "survival" may be measured over different periods, such as five, ten or 15 years. Accordingly, the survivals may be five-year, ten-year or 15-year survivals.

In embodiments of the methods of the above aspects, the subject may have colorectal cancer in different forms and/or stages.

In some embodiments of these aspects, the colorectal cancer in question may be a node-negative colorectal cancer, i.e. colorectal cancer that has not progressed to the lymph node metastazing stage. In other similar embodiments, the colorectal cancer in question is in either Dukes' stage A or B. In yet other embodiments, the colorectal cancer in question is colorectal adenoma or colorectal carcinoma. In these embodiments, determining that the subject exhibits high PODXL protein expression may be of great value for the prognosis of future progression of the disease and thus form the basis for an informed decision with regard to future disease management. Within a group of subjects afflicted with such a comparatively early stage of disease, subjects with high PODXL protein expression probably are at a comparatively high risk of developing a more aggressive disease. High PODXL protein expression among subjects having node-negative colorectal cancer or Dukes' stage A or B colorectal cancer may therefore indicate that these subjects should be monitored more closely and/or treated differently than subjects that do not exhibit high PODXL protein expression. The methods according to the present disclosure therefore offers the possibility of a greater chance for survival over a certain period of time and/or longer survival time for such subjects, owing to the additional prognostic information given by the PODXL protein marker.

The inventors have found that the finding of the present disclosure applies to colorectal cancers in all of the Dukes' stages. In other words, the prognostic relevance appears to be independent of the stage of the colorectal cancer in question.

Subjects having a Dukes' stage A colorectal cancer are traditionally not treated with adjuvant chemotherapy. However, guided by the teachings of the present disclosure, a physician may decide to give such a subject exhibiting high PODXL protein expression an adjuvant treatment anyway.

Consequently, in embodiments of the methods of the above aspects, the colorectal cancer is in Dukes' stage A. In an alternative or complementary embodiment, said colorectal cancer is in T1-2, N0 and M0 according to the TNM staging system described above.

Regarding subjects having a Dukes' stage B cancer, it may be particularly difficult to determine whether to apply an adjuvant therapy or not. Dukes' stage B subjects in particular may thus be revealed from treatment after a favorable prognosis has been determined by means of a PODXL protein measurement. Accordingly, in some embodiments, the colorectal cancer of the methods of the above aspects may be in Dukes' stage B.

Subjects having Dukes' stage C colorectal cancers are normally treated with adjuvant treatment. If such a subject is found to have a relatively poor prognosis, a combined adjuvant treatment may be considered more appropriate than a single treatment, even though the combined treatment causes more side-effects and is more costly.

Accordingly, in some embodiments, the colorectal cancer of the methods of the above aspects may be a metastazing colorectal cancer. In similar embodiments, the colorectal cancer in question may be in Dukes' stage C or D, preferably C.

A colorectal cancer invading the serosa layer (T4) is normally considered to be particularly aggressive. Consequently, a subject having such a colorectal cancer generally has a relatively poor prognosis with risk for tumor spreading to the abdominal cavity. The inventors have found that PODXL protein is overexpressed in colorectal tumors invading the serosa. Consequently, high levels of PODXL protein expression is an indicator of a serosa-invading tumors (and thus of poor prognosis). Further, the inventors see a connection between serosa invasion and metastazing cancer. Consequently, high levels of PODXL protein expression may also be an indicator of risk of metastasis. Accordingly, colorectal cancer subjects having high levels of PODXL may, according to one embodiment of the present disclosure, be examined for metastases and/or monitored for the development of metastases.

It follows that in embodiments of the first aspect, the first and the second group may consist of subjects having cancers of the same stage, grade and/or type as the subject of the method.

In conclusion, the methods of the present disclosure may yield information which forms the basis of a personalized treatment regimen.

In embodiments of the methods of the above aspects, the sample may be a body fluid sample. For example, the body fluid sample may be selected from the group consisting of blood, plasma, serum, cerebral fluid, urine, semen, lymph and exudate. Alternatively, the sample may be a cytology sample or a stool sample.

Here, blood (or blood-derived) samples are particularly interesting. The inventors have noted that cells expressing PODXL protein migrate towards blood vessels and are thus likely to leak into the circulatory system. Further, anti-PODXL antibodies are shown to bind living cells (see Examples, section 8) and the PODXL protein has been detected in blood. Thus, step a) may involve evaluating the amount of PODXL protein expressed in circulating tumor cells.

The level of PODXL protein expression may preferably be measured intracellularly. Thus, the body fluid, cytology or stool sample may for example comprise cells, such as tumor cells.

In further embodiments of the methods of the above aspects, the sample may be a tissue sample, such as a colorectal tissue sample (a sample derived from the colon or rectum), such as a colorectal tumor tissue sample. Tissue samples facilitate PODXL protein expression analysis by means of immunohistochemistry.

The results of FIG. 7 are based on examination of tissue samples from non-rectal colorectal tumors. Accordingly, in embodiments of the methods of the above aspects the sample may be a tissue sample derived from the colon.

The results of Examples, Section 3, are based on examination on tissue samples from the sigmoid colon. Accordingly, in embodiments of the methods of the above aspects the sample may be a tissue sample derived from the sigmoid colon.

The inventors have noted that the PODXL expression in a subset of tumor cells at the invasive tumor front may be particularly relevant for the establishment of a prognosis or selection of a treatment. Sometimes, such a subset of tumor cells is referred to as "tumor budding cells", see e.g. Prall and Hase et al. (Prall F: Tumour budding in colorectal carcinoma. Histopathology 2007, 50(1):151-162 and Hase K et al: Prognostic value of tumor "budding" in patients with colorectal cancer. *Dis Colon Rectum* 1993, 36(7):627-635). The evaluation of step a) may thus be limited to tumor budding cells of said sample.

Further, the inventors have noted that membranous or cytoplasmic, in particular membranous, expression of PODXL protein is relevant for determining prognoses or selecting treatments. The evaluation of step a) may thus be limited to the membranes of cells, such as tumor cells, of said sample.

Consequently, when a tissue sample is examined, only the membranes of tumor cells, such as tumor budding cells, may be taken into consideration. Such examination may for example be aided by immunohistochemical staining.

The tissue samples in Examples, Sections 3 and 4, are from male and female humans, and the inventors have found that the prognostic relevance of PODXL protein is independent of the subject's sex. Accordingly, the subject of the methods of the above aspects may be a human, and further, the subject of the methods of the above aspects may be male or female.

Figures 3A, 3B:
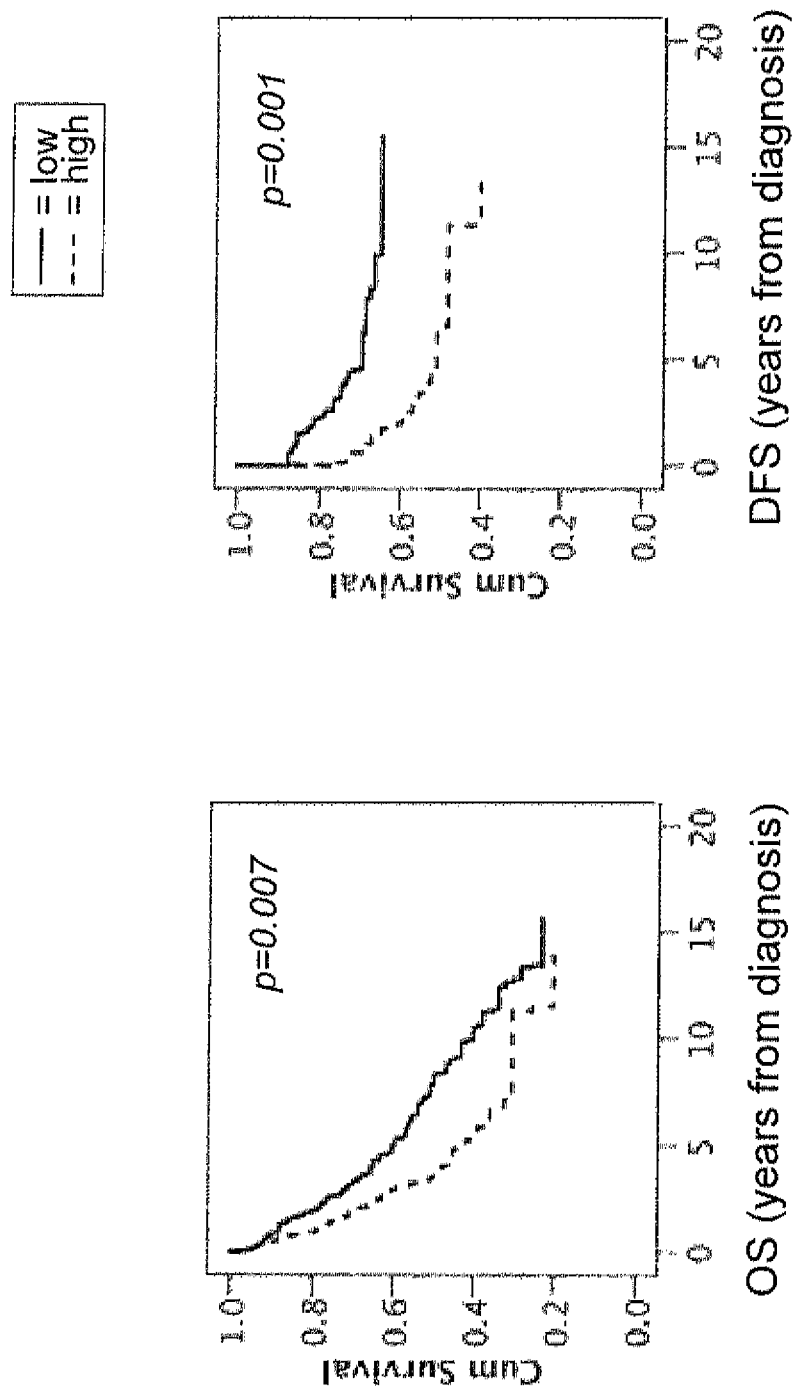
FIG. 3A shows OS and 3B shows DFS.

When performing the methods according to the above aspects, it may be convenient to use zero as the reference value, because in such case, it has only to be established in step a) whether PODXL protein is present in the sample or not. FIG. 3 indicates that zero (i.e. no detectable PODXL protein) is a working cut-off value for establishing two subgroups of different prognosis.

Thus, in embodiments of the methods of the above aspects, the sample value of step a) may be either 1, corresponding to detectable PODXL protein in the sample, or 0, corresponding to no detectable PODXL protein in the sample. Consequently, in such embodiments, the evaluation of the sample is digital: PODXL protein is considered to be either present or not. In the context of the present disclosure, "no detectable PODXL protein" refers to an amount of PODXL protein that is so small that it is not, during normal operational circumstances, detectable by a person or an apparatus performing the step a). The "normal operational circumstances" refer to the laboratory methods and techniques a person skilled in the art would find appropriate for performing the methods of the present disclosure.

Likewise, in embodiments of the methods of the above aspects, the sample value of step d) may be either 1, corresponding to detectable COX-2 in the sample, or 0, corresponding to no detectable COX-2 in the sample.

Accordingly, in embodiments of the methods of the present disclosure, the reference value of step b) may be 0. And it follows that, in further embodiments of the methods of the present disclosure, the reference value of step b) may correspond to a reference sample having no detectable PODXL protein (see below).

Likewise, in embodiments of the methods of the present disclosure, the reference value of step e) may be 0. And it follows that, in further embodiments of the methods of the present disclosure, the reference value of step e) may correspond to a reference sample having no detectable COX-2 (see below).

A sample value of PODXL protein being higher than the reference value, or a subject from which such sample value is obtained, is sometimes referred to herein as being "PODXL protein high". Further, a sample value of PODXL protein being lower than, or equal to, the reference value, or a subject from which such sample value is obtained, is sometimes referred to herein as being "PODXL protein low".

Likewise, a sample value of COX-2 being higher than the reference value, or a subject from which such sample value is obtained, is sometimes referred to herein as being "COX-2 high". Further, a sample value of COX-2 protein being lower than, or equal to, the reference value, or a subject from which such sample value is obtained, is sometimes referred to herein as being "COX-2 low".

In the context of the present disclosure, the terms "sample value" and "reference value" are to be interpreted broadly. (The discussion below applies mutatis mutandis to COX-2 and quantification thereof.) The quantification of PODXL protein to obtain these values may be done via automatic means, via a scoring system based on visual or microscopic inspection of samples, or via combinations thereof. However, it is also possible for a skilled person, such as a person skilled in the art of histopathology, to determine the sample and reference values by inspection of tissue slides from said sample that have been stained for PODXL protein expression. The determination of the sample value being higher than the reference value may thus correspond to the determination, upon visual or microscopic inspection, that a tissue slide from the sample is more densely stained and/or exhibit a larger fraction of stained cells than is the case for a reference tissue slide. The sample value may also be compared to a reference value given by a literal reference, such as a reference value described in wording or by a reference picture. Consequently, the sample and/or reference values may in some cases be mental values that the skilled person determines upon inspection and comparison.

For example, the skilled person may categorize a sample as being PODXL protein high or low, wherein the sample is categorized as high if it contains more PODXL protein than a previously inspected reference sample and low if it contains less or equally much. Such evaluation may be assisted by staining the sample, and, if necessary, a reference sample, with a staining solution comprising e.g., antibodies selective for PODXL protein.

One or more of the steps of the methods of the present disclosure may be implemented in an apparatus. For example, step a) and optionally step b) may be performed in an automatic analysis apparatus, and such apparatus may be based on a platform adapted for immunohistochemical analysis. As an example, one or more tumor tissue sample(s) from the subject in question may be prepared for immunohistochemical analysis manually and then loaded into the automatic analysis apparatus, which gives the sample value of step a) and optionally also performs the comparison with the reference value of step b). The operator performing the analysis, the physician ordering the analysis or the apparatus itself may then draw the conclusion of step c). Consequently, software adapted for drawing the conclusion of step c) may be implemented on the apparatus.

A reference value, found to be relevant for establishing a prognosis or making treatment decisions regarding colorectal cancer subjects, for use as comparison with the sample value from the subject, may be provided in various ways. With the knowledge of the teachings of the present disclosure, the skilled artisan can, without undue burden, provide relevant reference values for performing the methods of the present disclosure.

The person performing the methods of the above aspects may, for example, adapt the reference value to desired information. For example, the reference value may be adapted to yield the most significant prognostic information, e.g., the largest separation between the PODXL protein high survival curve and the PODXL protein low survival curve (see the figures), which corresponds to the largest difference in survival between the first and the second group of the first aspect. Alternatively, the reference value may be selected such that a group of subjects having particularly good prognoses or particularly poor prognoses is singled out.

In embodiments of the methods of the above aspects, the reference value may correspond to the amount of PODXL protein expression in a healthy tissue, such as healthy colorectal tissue, or stroma tissue of the subject of the method. As another example, the reference value may be provided by the amount of PODXL protein expression measured in a standard sample of normal tissue from another, comparable subject. As another example, the reference value may be provided by the amount of PODXL protein expression measured in a reference sample comprising tumor cells, such as a reference sample of tumor tissue, e.g., colorectal tumor tissue. The amount of protein expression of the reference sample may preferably be previously established.

Further, the reference value may for example be provided by the amount of PODXL protein expression measured in a reference sample comprising cell lines, such as cancer cell lines, expressing a predetermined, or controlled, amount of PODXL protein. The person skilled in the art understands how to provide such cell lines, for example guided by the disclosure of Rhodes et al. (2006) *The biomedical scientist*, p 515-520.

Consequently, the reference value may be provided by the amount of PODXL protein measured in a reference sample comprising cells expressing a predetermined amount of PODXL protein. Accordingly, in embodiments of the methods of the present disclosure, the reference value may be a predetermined value corresponding to the amount of PODXL protein expression in a reference sample.

However, the amount of PODXL protein in the reference sample does not have to directly correspond to the reference value (this is further discussed below). The reference sample may also provide an amount of PODXL protein that helps a person performing the method to assess various reference values. For example, the reference sample(s) may help in creating a mental image of the reference value by providing a "positive" reference value and/or a "negative" reference value.

One alternative for the quantification of PODXL protein in a sample, such as the sample earlier obtained from the subject or the reference sample, is the determination of the fraction of cells in the sample that exhibit PODXL protein expression over a certain level. The fraction may for example be: a "cellular fraction", wherein the PODXL protein expression of the whole cells is taken into account; a "cytoplasmic fraction", wherein the PODXL protein expression of only the membranes/cytoplasms of the cells is taken into account; or a "nuclear fraction", wherein the PODXL protein expression of only the nuclei of the cells is taken into account. The nuclear or cytoplasmic fraction may for example be classified as <1%, 1-50%, >50% immunoreactive cells of the relevant cell population. The "cytoplasmic fraction" corresponds to the percentage of relevant cells in a sample that exhibits a positive staining in the membrane/cytoplasm, wherein a medium or distinct and strong immunoreactivity in the membrane/cytoplasm is considered positive and no or faint immunoreactivity in the membrane/cytoplasm is considered negative. The person skilled in the art of pathology understands which cells that are relevant under the conditions present when performing the method and may determine a cytoplasmic or nuclear fraction based on his general knowledge and the teachings of the present disclosure. The relevant cells may for example be tumor cells.

Another alternative for the quantification of PODXL protein expression in a sample, such as the sample earlier obtained from the subject or the reference sample, is the determination of the overall staining intensity of the sample. The intensity may for example be: a "cellular intensity", wherein the PODXL protein expression of the whole cells is taken into account; a "cytoplasmic intensity", wherein the PODXL protein expression of only the membranes/cytoplasms of the cells is taken into account, or a "nuclear intensity", wherein the PODXL protein expression of only the nuclei of the cells is taken into account. Cytoplasmic and nuclear intensity is subjectively evaluated in accordance with standards used in clinical histopathological diagnostics. Outcome of a cytoplasmic intensity determination may be classified as: absent=no overall immunoreactivity in the membranes/cytoplasms of relevant cells of the sample, weak=faint overall immunoreactivity in the membranes/cytoplasms of relevant cells of the sample, moderate=medium overall immunoreactivity in the membranes/cytoplasms of relevant cells of the sample, or strong=distinct and strong overall immunoreactivity in the membranes/cytoplasms of relevant cells of the sample. In some embodiments, the absent and weak values may be combined into a absent/weak value. The person skilled in the art understands which cells that are relevant under the conditions present when performing the method and may determine a nuclear or cytoplasmic intensity based on his general knowledge and the teachings of the present disclosure. The relevant cells may for example be tumor cells.

The inventors have found that membranous/cytoplasmic expression of PODXL protein is particularly relevant for establishing prognoses.

Thus, in embodiments of the methods of the above aspects, the reference value may be a cytoplasmic fraction, a cytoplasmic intensity or a combination thereof. Accordingly, the sample value may be a cytoplasmic fraction, a cytoplasmic intensity or a combination thereof.

As seen in the figures, more than one reference value based on cytoplasmic expression of PODXL protein may function as a relevant reference value for determining whether the prognosis for survival is relatively good or relatively poor.

Thus, in embodiments of the methods of the above aspects, the reference value of step b) is a cytoplasmic fraction of 95% or lower, such as 90% or lower, such as 85% or lower, such as 80% or lower, such as 75% or lower, such as 70% or lower, such as 65% or lower, such as 60% or lower, such as 55% or lower, such as 50% or lower, such as 45% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

Further, in embodiments of the methods of the above aspects the reference value of step b) may be a moderate cytoplasmic intensity of PODXL protein expression or lower, such as a weak cytoplasmic intensity of PODXL protein expression or lower, such as an absent cytoplasmic of PODXL protein expression.

The results of the present disclosure are based on reference values which are combinations or functions of cytoplasmic intensities and cytoplasmic fractions.

For example, each sample may be assigned a value from 0-3, wherein:

"0" represents a negative cytoplasmic intensity and a cytoplasmic fraction of <1%, "1" represents a weak cytoplasmic intensity and a cytoplasmic fraction of 1-100%, "2" represents a moderate or strong cytoplasmic intensity and a cytoplasmic fraction of 1-50%, and "3" represents a moderate or strong cytoplasmic intensity and a cytoplasmic fraction of >50%.

The cut-off line may for example be drawn between 1 and 2 (FIG. 2, 6B 7) or between 0 and 1 (FIG. 3).

Accordingly, an absent or moderate cytoplasmic intensity may be a particularly relevant reference value. Further, a low cytoplasmic fraction, such as 0-25% (or 0-10%) or an intermediate cytoplasmic fraction, such as 25-75% (or 40-60%) may also be a particularly relevant reference value.

Also, the criterion for the conclusion in step c) may for example be that the sample value is higher than a cytoplasmic fraction of 1% and higher than an absent cytoplasmic intensity. Further, the criterion for the conclusion in step c) may for example be that the sample value is higher than a cytoplasmic fraction of 1% and higher than a weak cytoplasmic intensity.

The reference value of step e) (regarding COX-2) may for example be a cytoplasmic fraction of 0-50%, such as 0-25%, such as 5-15%. Further, it may for example be an absent, weak or moderate cytoplasmic intensity. Also, it may be combination or a function of a cytoplasmic fraction and a cytoplasmic intensity.

The person skilled in the art realizes that another reference value which is an intensity value or a fraction value also fall within the scope of the present invention. Likewise, the person skilled in the art realizes that other combinations or functions of fractions and intensities also fall within the scope of the present invention. Consequently, the reference value may involve two, and possibly even more, criteria.

In general, the selection of an intensity value and/or a fraction value as the reference value may depend on the staining procedure, e.g., on the employed anti-PODXL antibody and on the staining reagents.

Guided by the present disclosure, a person skilled in the art, e.g. a pathologist, understands how to perform the evaluation yielding a fraction, such as a cellular, cytoplasmic or nuclear fraction, or an intensity, such as a cellular, cytoplasmic or nuclear intensity. For example, the skilled artisan may use a reference sample comprising a predetermined amount of PODXL protein for establishing the appearance of a certain fraction or intensity.

However, a reference sample may not only be used for the provision of the actual reference value, but also for the provision of an example of a sample with an amount of PODXL protein that is higher than the amount corresponding to the reference value. As an example, in histochemical staining, such as in immunohistochemical staining, the skilled artisan may use a reference sample for establishing the appearance of a stained sample having a high amount of PODXL protein, e.g., a positive reference. Subsequently, the skilled artisan may assess the appearances of samples having lower amounts of PODXL protein, such as the appearance of a sample with an amount of PODXL protein corresponding to the reference value. In other words, the skilled artisan may use a reference sample to create a mental image of a reference value corresponding to an amount of PODXL protein which is lower than that of the reference sample. Alternatively, or as a complement, in such assessments, the skilled artisan may use another reference sample having a low amount of PODXL protein, or lacking detectable PODXL protein, for establishing the appearance of such sample, e.g., as a "negative reference".

For example, if a weak cytoplasmic intensity is used as the reference value, two reference samples may be employed: a first reference sample having no detectable PODXL protein, and thus corresponding to a absent cytoplasmic intensity, which is lower than the reference value; and a second reference sample having an amount of PODXL protein corresponding to a strong cytoplasmic intensity, which is higher than the reference value.

Consequently, in the evaluation, the skilled artisan may use a reference sample for establishing the appearance of a sample with a high amount of PODXL protein. Such reference sample may be a sample comprising tissue expressing a high amount of PODXL protein, such as a sample comprising colorectal tumor tissue having a pre-established high expression of PODXL protein.

Accordingly, the reference sample may provide an example of a strong cytoplasmic intensity (CI). With the knowledge of the appearance of a sample with strong CI, the skilled artisan may then divide samples into the CI categories absent, weak, moderate and strong. This division may be further assisted by a reference sample lacking detectable PODXL protein (negative reference), i.e., a reference sample providing an absent cytoplasmic intensity. Also, the reference sample may provide an example of a sample with a cytoplasmic fraction (CF) higher than 75%. With the knowledge of the appearance of a sample with more than 75% positive cells, the skilled artisan may then evaluate the CF of other samples having e.g., a lower percentage of positive cells. This division may be further assisted by a reference sample essentially lacking PODXL protein (negative reference), i.e., a reference sample providing a low CF (such as <1% or 0).

As mentioned above, cell lines expressing a controlled amount of PODXL protein may be used as the reference, in particular as a positive reference.

One or more pictures may also be provided as the "reference sample". For example, such a picture may show an example of a tumor tissue slide stained with a certain antibody during certain conditions exhibiting a certain cellular intensity and/or fraction. The above discussion about the "reference sample" applies mutatis mutandis to pictures.

The discussion above regarding reference samples applies mutatis mutandis to the determination of the COX-2 status.

The cell lines or pictures may also form part of the kit according to the present disclosure (see below).

Further, the skilled person should recognize that the usefulness of the methods according to the above aspects is not limited to the quantification of any particular variant of the PODXL protein present in the subject in question, as long as the protein is encoded by the relevant gene and presents the relevant pattern of expression. As a non-limiting example, the PODXL protein may comprise a sequence selected from:
  i) SEQ ID NO:1; and
  ii) a sequence which is at least 85% identical to SEQ ID NO:1.

In some embodiments, sequence ii) above is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:1.

As another non-limiting example, the PODXL protein may comprise, or consists of, a sequence selected from:
  i) SEQ ID NO:2 or 3; and
  ii) a sequence which is at least 85% identical to SEQ ID NO:2.

SEQ ID NO:2 and 3 are two splice variants of the PODXL protein. SEQ ID NO:1 is a subregion which is common to the extracellular regions of the respective splice variants.

In some embodiments, sequence ii) above is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:2 or 3.

The term "% identical", as used in the context of the present disclosure, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). The amino acid residues at each position are compared, and the percentage of positions in the query sequence that have identical correspondences in the target sequence is reported as % identical. Also, the target sequence determines the number of positions that are compared. Consequently, in the context of the present disclosure, a query sequence that is shorter than the target sequence can never be 100% identical to the target sequence. For example, a query sequence of 85 amino acids may at the most be 85% identical to a target sequence of 100 amino acids.

In some embodiments, step a) of the methods of the above aspects may comprise:
  obtaining biological material from the subject, excising or selecting a relevant part of the biological material to obtain said sample and optionally arranging the sample on a solid phase to facilitate the evaluation of step a). Step a) may thus, as an example, comprise obtaining tissue material from the colon or rectum of said subject, optionally fixating the tissue material in paraffin or formalin, histo-processing the tissue material to obtain a section which constitute said sample and optionally mounting said sample on a transparent slide, such as a glass slide, for microscopy.

In embodiments of the methods of the aspects above, the PODXL protein may be detected and/or quantified through the application to the sample of a detectable and/or quantifiable affinity ligand, which is capable of selective interaction with the PODXL protein. The application of the affinity ligand is performed under conditions that enable binding of the affinity ligand to any PODXL protein in the sample.

To concretize, in embodiments of the methods of the aspects above, step a) may comprise:
  a1) applying to said sample a quantifiable affinity ligand capable of selective interaction with the PODXL protein to be evaluated, said application being performed under conditions that enable binding of said affinity ligand to PODXL protein present in said sample;
  a2) removing non-bound affinity ligand; and
  a3) quantifying the affinity ligand remaining in association with said sample to evaluate said amount.

"Affinity ligand remaining in association with the sample" refers to affinity ligand which was not removed in step a2), e.g., the affinity ligand bound to the sample. Here, the binding may for example be the interaction between antibody and antigen.

However, the removal of non-bound affinity ligand according to a2), e.g. the washing, is not always necessary. Thus, in some embodiments of the methods of the aspects above, step a) may comprise:
  aI) applying to said sample a quantifiable affinity ligand capable of selective interaction with the PODXL protein to be evaluated, said application being performed under conditions that enable binding of said affinity ligand to PODXL protein present in said sample;
  aII) quantifying the affinity bound to said sample to evaluate said amount.

The two embodiments above apply mutatis mutandis to step d) (COX-2 detection).

In the context of the present disclosure, "specific" or "selective" interaction of e.g., an affinity ligand with its target or antigen means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an antibody and its antigen is from $10^{-7}$ to $10^{-11}$ M. However, high specificity does not necessarily require high affinity. Molecules with low affinity (in the molar range) for its counterpart have been shown to be as specific as molecules with much higher affinity. In the case of the present disclosure, a specific or selective interaction refers to the extent to which a particular method can be used to determine the presence and/or amount of a specific protein, the target protein, under given conditions in the presence of other proteins in a tissue sample or fluid sample of a naturally occurring or processed biological fluid. In other words, specificity or selectivity is the capacity to distinguish between related proteins. Specific and selective are sometimes used interchangeably in the present description. For example, the specificity or selectivity of an antibody may be determined as in Examples, section 2, below, wherein analysis is performed using a protein array set-up, a suspension bead array and a multiplexed competition assay, respectively. Specificity and selectivity determinations are also described in Nilsson P et al. (2005) Proteomics 5:4327-4337.

It is regarded as within the capabilities of those of ordinary skill in the art to select or manufacture the proper affinity ligand and to select the proper format and conditions for detection and/or quantification. Nevertheless, examples of affinity ligands that may prove useful, as well as examples of formats and conditions for detection and/or quantification, are given below for the sake of illustration.

Thus, in embodiments of the present disclosure, the affinity ligand may be selected from the group consisting of antibodies, fragments thereof and derivatives thereof, i.e., affinity ligands based on an immunoglobulin scaffold. The antibodies and the fragments or derivatives thereof may be isolated and/or mono-specific. Antibodies comprise monoclonal and polyclonal antibodies of any origin, including murine, rabbit, human and other antibodies, as well as chimeric antibodies comprising sequences from different species, such as partly humanized antibodies, e.g., partly humanized mouse antibodies. Polyclonal antibodies are produced by immunization of animals with the antigen of choice. Monoclonal antibodies of defined specificity can be produced using the hybridoma technology developed by Köhler and Milstein (Köhler G and Milstein C (1976) Eur. J. Immunol. 6:511-519). The antibody fragments and derivatives of the present disclosure are capable of selective interaction with the same antigen (e.g. PODXL protein) as the antibody they are fragments or derivatives of. Antibody fragments and derivatives comprise Fab fragments, consisting of the first constant domain of the heavy chain (CH1), the constant domain of the light chain (CL), the variable domain of the heavy chain (VH) and the variable domain of the light chain (VL) of an intact immunoglobulin protein; Fv fragments, consisting of the two variable antibody domains VH and VL (Skerra A and Plückthun A (1988) Science 240:1038-1041); single chain Fv fragments (scFv), consisting of the two VH and VL domains linked together by a flexible peptide linker (Bird R E and Walker B W (1991) Trends Biotechnol. 9:132-137); Bence Jones dimers (Stevens F J et al. (1991) Biochemistry 30:6803-6805); camelid heavy-chain dimers (Hamers-Casterman C et al. (1993) Nature 363:446-448) and single variable domains (Cai X and Garen A (1996) Proc. Natl. Acad. Sci. U.S.A. 93:6280-6285; Masat L et al. (1994) Proc. Natl. Acad. Sci. U.S.A. 91:893-896), and single domain scaffolds like e.g., the New Antigen Receptor (NAR) from the nurse shark (Dooley H et al. (2003) Mol. Immunol. 40:25-33) and minibodies based on a variable heavy domain (Skerra A and Plückthun A (1988) Science 240:1038-1041).

SEQ ID NO:1 was designed for immunizations, e.g., designed to lack transmembrane regions to ensure efficient expression in E. coli, and to lack any signal peptide, since those are cleaved off in the mature protein. Consequently, an antibody or fragment or derivative thereof according to the present disclosure may for example be one that is obtainable by a process comprising a step of immunizing an animal, such as a rabbit, with a protein whose amino acid sequence comprises, preferably consists of, the sequence SEQ ID NO:1. For example, the immunization process may comprise primary immunization with the protein in Freund's complete adjuvant. Also, the immunization process may further comprise boosting at least two times, in intervals of 2-6 weeks, with the protein in Freund's incomplete adjuvant. Processes for the production of antibodies or fragments or derivatives thereof against a given target are known in the art.

In the context of the present disclosure, a "mono-specific antibody" is one of a population of polyclonal antibodies which has been affinity purified on its own antigen, thereby separating such mono-specific antibodies from other antiserum proteins and non-specific antibodies. This affinity purification results in antibodies that bind selectively to its antigen. In the case of the present disclosure, the polyclonal antisera are purified by a two-step immunoaffinity based protocol to obtain mono-specific antibodies selective for the target protein. Antibodies directed against generic affinity tags of antigen fragments are removed in a primary depletion step, using the immobilized tag protein as the capturing agent. Following the first depletion step, the serum is loaded on a second affinity column with the antigen as capturing agent, in order to enrich for antibodies specific for the antigen (see also Nilsson P et al. (2005) Proteomics 5:4327-4337).

Polyclonal and monoclonal antibodies, as well as their fragments and derivatives, represent the traditional choice of affinity ligands in applications requiring selective biomolecular recognition, such as in the detection and/or quantification of PODXL protein according to the method aspects above. However, those of skill in the art know that, due to the increasing demand of high throughput generation of selective binding ligands and low cost production systems, new biomolecular diversity technologies have been developed during the last decade. This has enabled a generation of novel types of affinity ligands of both immunoglobulin as well as non-immunoglobulin origin that have proven equally useful as binding ligands in biomolecular recognition applications and can be used instead of, or together with, immunoglobulins.

The biomolecular diversity needed for selection of affinity ligands may be generated by combinatorial engineering of one of a plurality of possible scaffold molecules, and specific and/or selective affinity ligands are then selected using a suitable selection platform. The scaffold molecule may be of immunoglobulin protein origin (Bradbury A R and Marks J D (2004) J. Immunol. Meths. 290:29-49), of non-immunoglobulin protein origin (Nygren PÅ and Skerra A (2004) J. Immunol. Meths. 290:3-28), or of an oligonucleotide origin (Gold L et al. (1995) Annu. Rev. Biochem. 64:763-797).

A large number of non-immunoglobulin protein scaffolds have been used as supporting structures in development of novel binding proteins. Non-limiting examples of such structures, useful for generating affinity ligands against PODXL protein for use according to the present disclosure, are staphylococcal protein A and domains thereof and derivatives of these domains, such as protein Z (Nord K et al. (1997) Nat. Biotechnol. 15:772-777); lipocalins (Beste G et al. (1999) Proc. Natl. Acad. Sci. U.S.A. 96:1898-1903); ankyrin repeat domains (Binz H K et al. (2003) J. Mol. Biol. 332:489-503); cellulose binding domains (CBD) (Smith G P et al. (1998) J.

Mol. Biol. 277:317-332; Lehtiö J et al. (2000) Proteins 41:316-322); γ crystallines (Fiedler U and Rudolph R, WO01/04144); green fluorescent protein (GFP) (Peelle B et al. (2001) Chem. Biol. 8:521-534); human cytotoxic T lymphocyte-associated antigen 4 (CTLA-4) (Hufton S E et al. (2000) FEBS Lett. 475:225-231; Irving R A et al. (2001) J. Immunol. Meth. 248:31-45); protease inhibitors, such as Knottin proteins (Wentzel A et al. (2001) J. Bacteriol. 183:7273-7284; Baggio R et al. (2002) J. Mol. Recognit. 15:126-134) and Kunitz domains (Roberts B L et al. (1992) Gene 121:9-15; Dennis M S and Lazarus R A (1994) J. Biol. Chem. 269: 22137-22144); PDZ domains (Schneider S et al. (1999) Nat. Biotechnol. 17:170-175); peptide aptamers, such as thioredoxin (Lu Z et al. (1995) Biotechnology 13:366-372; Klevenz B et al. (2002) Cell. Mol. Life Sci. 59:1993-1998); staphylococcal nuclease (Norman T C et al. (1999) Science 285:591-595); tendamistats (McConell S J and Hoess R H (1995) J. Mol. Biol. 250:460-479; Li R et al. (2003) Protein Eng. 16:65-72); trinectins based on the fibronectin type III domain (Koide A et al. (1998) J. Mol. Biol. 284:1141-1151; Xu L et al. (2002) Chem. Biol. 9:933-942); and zinc fingers (Bianchi E et al. (1995) J. Mol. Biol. 247:154-160; Klug A (1999) J. Mol. Biol. 293:215-218; Segal D J et al. (2003) Biochemistry 42:2137-2148).

The above-mentioned examples of non-immunoglobulin protein scaffolds include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities.

In addition to non-immunoglobulin proteins, oligonucleotides may also be used as affinity ligands. Single stranded nucleic acids, called aptamers or decoys, fold into well-defined three-dimensional structures and bind to their target with high affinity and specificity. (Ellington A D and Szostak J W (1990) Nature 346:818-822; Brody E N and Gold L (2000) J. Biotechnol. 74:5-13; Mayer G and Jenne A (2004) BioDrugs 18:351-359). The oligonucleotide ligands can be either RNA or DNA and can bind to a wide range of target molecule classes.

For selection of the desired affinity ligand from a pool of variants of any of the scaffold structures mentioned above, a number of selection platforms are available for the isolation of a specific novel ligand against a target protein of choice. Selection platforms include, but are not limited to, phage display (Smith G P (1985) Science 228:1315-1317), ribosome display (Hanes J and Plückthun A (1997) Proc. Natl. Acad. Sci. U.S.A. 94:4937-4942), yeast two-hybrid system (Fields S and Song O (1989) Nature 340:245-246), yeast display (Gai S A and Wittrup K D (2007) Curr Opin Struct Biol 17:467-473), mRNA display (Roberts R W and Szostak J W (1997) Proc. Natl. Acad. Sci. U.S.A. 94:12297-12302), bacterial display (Daugherty P S (2007) Curr Opin Struct Biol 17:474-480, Kronqvist N et al. (2008) Protein Eng Des Sel 1-9, Harvey B R et al. (2004) PNAS 101(25):913-9198), microbead display (Nord O et al. (2003) J Biotechnol 106:1-13, WO01/05808), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399).

Thus, in embodiments of the present disclosure, the affinity ligand may be a non-immunoglobulin affinity ligand derived from any of the protein scaffolds listed above, or an oligonucleotide molecule.

The PODXL protein fragment SEQ ID NO:1 was designed to consist of a unique sequence with low homology with other human proteins and to minimize cross reactivity of generated affinity reagents. Consequently, in embodiments of the present disclosure, the affinity ligand may be capable of selective interaction with a polypeptide consisting of the sequence SEQ ID NO:1.

"The affinity ligand capable of selective interaction with a polypeptide consisting of the sequence SEQ ID NO:1" is capable of distinguishing a SEQ ID NO:1 fragment from a fragment consisting of another, non-overlapping, part of the PODXL protein.

As shown in Examples, sections 6 and 7, below, six epitope regions have been identified within SEQ ID NO:1. Thus, in embodiments of the present disclosure, the affinity ligand may be capable of selective interaction with a polypeptide consisting of 20 amino acids or less, such as 15 amino acids or less and comprising an amino acid sequence selected from SEQ ID NO:10-15.

The detection and/or quantification of the affinity ligand capable of selective interaction with the PODXL protein may be accomplished in any way known to the skilled person for detection and/or quantification of binding reagents in assays based on biological interactions. Accordingly, any affinity ligand described above may be used to quantitatively and/or qualitatively detect the presence of the PODXL protein. These "primary" affinity ligands may be labeled themselves with various markers or may in turn be detected by secondary, labeled affinity ligands to allow detection, visualization and/or quantification. This can be accomplished using any one or more of a multitude of labels, which can be conjugated to the affinity ligand capable of interaction with PODXL protein or to any secondary affinity ligand, using any one or more of a multitude of techniques known to the skilled person, and not as such involving any undue experimentation.

Non-limiting examples of labels that can be conjugated to primary and/or secondary affinity ligands include fluorescent dyes or metals (e.g., fluorescein, rhodamine, phycoerythrin, fluorescamine), chromophoric dyes (e.g., rhodopsin), chemiluminescent compounds (e.g., luminal, imidazole), bioluminescent proteins (e.g., luciferin, luciferase), and haptens (e.g., biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g., horseradish peroxidase, alkaline phosphatase, beta-lactamase), radioisotopes (e.g., $^{3}H$, $^{14}C$, $^{32}P$, $^{35}S$ or $^{125}I$) and particles (e.g., gold). In the context of the present disclosure, "particles" refer to particles, such as metal particles, suitable for labeling of molecules. Further, the affinity ligands may also be labeled with fluorescent semiconductor nanocrystals (quantum dots). Quantum dots have superior quantum yield and are more photostable compared to organic fluorophores and are therefore more easily detected (Chan et al. (2002) *Curr Opi Biotech.* 13: 40-46). The different types of labels can be conjugated to an affinity ligand using various chemistries, e.g., the amine reaction or the thiol reaction. However, other reactive groups than amines and thiols can be used, e.g., aldehydes, carboxylic acids and glutamine.

The method aspects above may be put to use in any of several known formats and set-ups, of which a non-limiting selection is discussed below.

In a set-up based on histology, the detection, localization and/or quantification of a labeled affinity ligand bound to its PODXL protein target may involve visualizing techniques, such as light microscopy or immunofluoresence microscopy. Other methods may involve the detection via flow cytometry or luminometry.

A biological sample, such as a tumor tissue sample (biopsy), which has been removed from the subject, may be used for detection and/or quantification of PODXL protein. The biological sample, such as the biopsy, may be an earlier obtained sample. If using an earlier obtained sample in a method, no steps of the method are practiced on the human or animal body. The affinity ligand may be applied to the biological sample for detection and/or quantification of the PODXL protein. This procedure enables not only detection of PODXL protein, but may in addition show the distribution and relative level of expression thereof.

The method of visualization of labels on the affinity ligand may include, but is not restricted to, fluorometric, luminometric and/or enzymatic techniques. Fluorescence is detected and/or quantified by exposing fluorescent labels to light of a specific wavelength and thereafter detecting and/or quantifying the emitted light in a specific wavelength region. The presence of a luminescently tagged affinity ligand may be detected and/or quantified by luminescence developed during a chemical reaction. Detection of an enzymatic reaction is due to a color shift in the sample arising from a chemical reaction. Those of skill in the art are aware that a variety of different protocols can be modified for proper detection and/or quantification.

In embodiments of the methods of the above aspects, a biological sample may be immobilized onto a solid phase support or carrier, such as nitrocellulose or any other solid support matrix capable of immobilizing PODXL protein present in the biological sample applied to it. Some well-known solid state support materials useful in the present invention include glass, carbohydrate (e.g., Sepharose), nylon, plastic, wool, polystyrene, polyethene, polypropylene, dextran, amylase, films, resins, cellulose, polyacrylamide, agarose, alumina, gabbros and magnetite. After immobilization of the biological sample, primary affinity ligand specific to PODXL protein may be applied, e.g., as described in Examples, Section 3, of the present disclosure. If the primary affinity ligand is not labeled in itself, the supporting matrix may be washed with one or more appropriate buffers known in the art, followed by exposure to a secondary labeled affinity ligand and washed once again with buffers to remove unbound affinity ligands. Thereafter, selective affinity ligands may be detected and/or quantified with conventional methods. The binding properties for an affinity ligand may vary from one solid state support to the other, but those skilled in the art should be able to determine operative and optimal assay conditions for each determination by routine experimentation.

Consequently, in embodiments of the methods of the above aspects, the quantifiable affinity ligand of a1) or aI) may be detected using a secondary affinity ligand capable of recognizing the quantifiable affinity ligand. The quantification of a3) or aII) may thus be carried out by means of a secondary affinity ligand with affinity for the quantifiable affinity ligand. As an example, the secondary affinity ligand may be an antibody or a fragment or a derivative thereof.

As an example, one available method for detection and/or quantification of the PODXL protein is by linking the affinity ligand to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a solid material or with a solid material conjugated to an affinity ligand against the PODXL protein, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

As stated above, primary and any secondary affinity ligands can be labeled with radioisotopes to enable detection and/or quantification. Non-limiting examples of appropriate radiolabels in the present disclosure are $^{3}H$, $^{14}C$, $^{32}P$, $^{35}S$ or $^{125}I$. The specific activity of the labeled affinity ligand is dependent upon the half-life of the radiolabel, isotopic purity, and how the label has been incorporated into the affinity ligand. Affinity ligands are preferably labeled using well-known techniques (Wensel T G and Meares C F (1983) in: *Radioimmunoimaging and Radioimmunotherapy* (Burchiel S W and Rhodes B A eds.) Elsevier, New York, pp 185-196). A thus radiolabeled affinity ligand can be used to visualize PODXL protein by detection of radioactivity in vivo or in vitro. Radionuclear scanning with e.g., gamma camera, magnetic resonance spectroscopy or emission tomography function for detection in vivo and in vitro, while gamma/beta counters, scintillation counters and radiographies are also used in vitro.

To perform the methods of the present disclosure, a kit may be employed. As a third aspect of the present disclosure, there is thus provided a kit for establishing a prognosis of colorectal cancer, which comprises a) a quantifiable affinity ligand capable of selective interaction with a PODXL protein;

b) reagents necessary for quantifying the amount of the quantifiable affinity ligand of a);

c) a quantifiable affinity ligand capable of selective interaction with a COX-2 protein; and d) reagents necessary for quantifying the amount of the quantifiable affinity ligand of c), wherein the reagents of b) and d) are the same or different.

Accordingly, the same reagents, such as the same secondary antibody, may be used for quantifying both the anti-PODXL protein affinity ligand and the anti-COX-2 affinity ligand.

The present kit is thus particularly useful in the methods wherein the level of COX-2 is evaluated.

Various components of the kit according to the third aspect may be selected and specified as described above in connection with the method aspects of the present disclosure.

Thus, the kit according to the present disclosure comprises affinity ligands against PODXL protein and COX-2, as well as other means that help to quantify the specific and/or selective affinity ligands after they have bound specifically and/or selectively to the respective target proteins. For example, the kit may contain a secondary affinity ligand for detecting and/or quantifying a complex formed by the target proteins and the affinity ligands. The kit may also contain various auxiliary substances other than affinity ligands, to enable the kit to be used easily and efficiently. Examples of auxiliary substances include solvents for dissolving or reconstituting lyophilized protein components of the kit, wash buffers, substrates for measuring enzyme activity in cases where an enzyme is used as a label, target retrieval solution to enhance the accessibility to antigens in cases where paraffin or formalin-fixed tissue samples are used, and substances such as reaction arresters, e.g., endogenous enzyme block solution to decrease the background staining and/or counterstaining solution to increase staining contrast, that are commonly used in immunoassay reagent kits.

In embodiments of the kit aspect, the affinity ligand may be selected as described above in connection with the method aspects.

Consequently, the affinity ligand of a) and/or c) may be selected from the group consisting of antibodies, fragments thereof and derivatives thereof.

Further, in accordance with what is described above in connection with the method aspects, the detectable affinity ligands may in embodiments of the kit aspect comprise a label selected from the group consisting of fluorescent dyes and metals, chromophoric dyes, chemiluminescent compounds and bioluminescent proteins, enzymes, radioisotopes, particles and quantum dots. Alternatively, the reagents necessary for quantifying the amount of the affinity ligands comprise one or more secondary affinity ligand(s) capable of recognizing the quantifiable affinity ligands. As an example, the secondary affinity ligand(s) capable of recognizing the quantifiable affinity ligand(s) comprises a label selected from the group consisting of fluorescent dyes or metals, chromophoric dyes, chemiluminescent compounds and bioluminescent proteins, enzymes, radioisotopes, particles and quantum dots.

The kit according to the kit aspect may also advantageously comprise one or more reference sample(s) for provision of, or yielding, one or more reference value(s) to be used for comparison with PODXL protein and/or COX-2 sample values. For example, a reference sample may comprise a predetermined amount of PODXL protein or COX-2. Such a reference sample may for example be constituted by a tissue or cell line sample containing the predetermined amount of PODXL protein or COX-2. The tissue or cell line reference sample may then be used by the person of skill in the art in the determination of the protein expression status in the sample being studied, by manual, such as ocular, or automated comparison of expression levels in the reference tissue sample and the subject sample.

The above-mentioned cell lines may for example be cancer cell lines. Further, the cell lines may be expressing a predetermined, or controlled, amount of PODXL protein. The person skilled in the art understands how to provide such cell lines, for example guided by the disclosure of Rhodes et al. (2006) The biomedical scientist, p 515-520. As an example, the cell lines may be formalin fixed. Also, such formalin fixed cell lines may be paraffin embedded.

The above-mentioned tissue reference sample may be a tissue sample adapted to ocular or microscopic evaluation. As an example, the tissue reference sample may be fixated in paraffin or buffered formalin and/or histo-processed to sections (e.g., μm-thin sections) that are mounted on microscopic glass-slides. The tissue reference sample may be further adapted to staining with affinity ligands, such as antibodies.

Consequently, in embodiments of the kit aspect, the reference sample may be adapted to directly, or indirectly, provide any relevant reference value, such as any one of the reference values discussed above.

The wording "reference sample for provision of the reference value" is to be interpreted broadly in the context of the present disclosure. The reference sample may comprise an amount of PODXL protein or COX-2 actually corresponding to the reference value, but it may also comprise an amount of PODXL protein or COX-2 corresponding to a value being higher than the reference value. In the latter case, the "high" value may be used by a person performing the method as an upper reference (positive reference) for assessing, e.g., the appearance of, a reference value which is lower than the "high" value. The person skilled in the art of immunohistochemistry understands how to do such an assessment. Further, as an alternative or a complementing example, the skilled person may use another reference sample comprising a low amount of PODXL protein or COX-2 for provision of a "low" value in such an assessment, e.g., as a negative reference. This is further discussed above in connection with the method aspects.

Consequently, in embodiments of the kit aspect, a reference sample may comprise an amount of PODXL protein corresponding to a reference value. Examples of such reference values are discussed above in connection with the method aspects.

And further, in embodiments of the kit aspect, a reference sample may comprise an amount of COX-2 corresponding to a reference value. Examples of such reference values are also discussed above in connection with the method aspects.

Further, in alternative or complementing embodiments of the kit aspect, the kit may comprise a reference sample comprising an amount of PODXL protein or COX-2 corresponding to a value being higher than the reference value. Such reference sample may for example comprise an amount of PODXL protein or COX-2 corresponding to a cytoplasmic fraction of 75% or higher and/or a strong cytoplasmic intensity.

Still further, in alternative or complementing embodiments of the kit aspect, the kit may comprise a reference sample comprising an amount of PODXL protein or COX-2 corresponding to a value being lower than or equal to the reference value, e.g., an absent cytoplasmic intensity and/or a cytoplasmic fraction of <2%, such as 0%.

Consequently, in embodiments of the kit aspect, the reference sample may be adapted to directly, or indirectly, provide any relevant reference value, such as any one of the reference values discussed above.

Following the findings presented above, the inventors have realized several uses for the PODXL protein or a fragment thereof.

Thus, as a fourth aspect of the present disclosure, there is provided a use of a PODXL protein as a prognostic marker for colorectal cancer. The use may be in vitro.

In a similar manner, there is provided a use of a PODXL protein as a marker of a relatively poor prognosis for a mammalian subject having a colorectal cancer.

As a configuration of the fourth aspect, there is provided a use of the PODXL protein as a marker of serosa invasion or metastazing cancer for a subject having colorectal cancer. This configuration is further discussed above.

In the context of the present disclosure, "prognostic marker" refers to something material which presence indicates a prognosis. The marker may thus be a biomarker, such as a human protein.

In embodiments of the fourth aspect, the PODXL protein may be provided in a biological sample, such as a colorectal tumor tissue sample, from a subject having a colorectal cancer. Further, for reasons discussed above, the colorectal tumor tissue sample may be a colon tumor tissue sample. The colon tumor tissue sample may for example be derived from the sigmoideum.

As a fifth aspect of the present disclosure, there is provided a use of a PODXL protein, or an antigenically active fragment thereof, for the production, selection or purification of a prognostic agent for establishing a prognosis for a mammalian subject having a colorectal cancer. The use may be in vitro.

In the context of the present disclosure, "prognostic agent" refers to an agent having at least one property being valuable in an establishment of a prognosis, e.g., a prognosis for a mammalian subject having a colorectal cancer. For example, the prognostic agent may be capable of selective interaction with the prognostic marker.

The prognostic agent may thus be an affinity ligand capable of selective interaction with the PODXL protein or the antigenically active fragment thereof. Examples of such affinity ligands are discussed above in connection with the method aspects.

Guided by the teachings of the present disclosure, the person skilled in the art understands how to use the PODXL protein or fragment in the production, selection or purification of the prognostic agent. For example, the use may comprise affinity purification on a solid support onto which the PODXL protein has been immobilized. The solid support may for example be arranged in a column. Further, the use may comprise selection of affinity ligands having specificity for the PODXL protein using a solid support onto which the polypeptide has been immobilized. Such solid support may be well plates (such as 96 well plates), magnetic beads, agarose beads or sepharose beads. Further, the use may comprise analysis of affinity ligands on a soluble matrix, for example using a dextran matrix, or use in a surface plasmon resonance instrument, such as a Biacore™ instrument, wherein the analysis may for example comprise monitoring the affinity for the immobilized PODXL protein of a number of potential affinity ligands.

Also, for the production of the prognostic agent, the PODXL protein or an antigenically active fragment thereof may be used in an immunization of an animal.

Such use may be involved in a method comprising the steps:
  i) immunizing an animal using the PODXL protein or antigenically an active fragment thereof as the antigen;
  ii) obtaining serum comprising the prognostic agent from the immunized animal; and, optionally,
  iii) isolating the prognostic agent from the serum.
  Alternatively the steps following the first step may be:
  ii') obtaining cells from the immunized animal, which cells comprise DNA encoding the prognostic agent,
  iii') fusing the cells with myeloma cells to obtain at least one clone, and
  iv') obtaining the prognostic agent expressed by the clone.

In embodiments of the fourth or fifth aspect, the amino acid sequence of the PODXL protein (or fragment thereof) may comprise or consist of a sequence selected from:
  i) SEQ ID NO:1; and
  ii) a sequence which is at least 85% identical to SEQ ID NO:1.

In some embodiments, sequence ii) is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:1.

Further, in embodiments of the fourth aspect the amino acid sequence of the PODXL protein may comprise or consist of a sequence selected from:
  i) SEQ ID NO:2 or 3; and
  ii) a sequence which is at least 85% identical to SEQ ID NO:2 or 3.

In some embodiments, sequence ii) is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:2 or 3.

As demonstrated under Examples below, several antigenic subregions of SEQ ID NO:1 have been identified. Thus, in embodiments of the present disclosure, the "antigenically active fragment" may consist of 25 amino acids or less and comprise an amino acid sequence selected from SEQ ID NO:10-18. Here, SEQ ID NO:10-15 may be considered to be preferred. In further embodiments, the "antigenically active fragment" may consist of 20 amino acids or less, such as 15 amino acids or less.

As a sixth aspect of the present disclosure, there is provided an affinity ligand capable of selective interaction with a PODXL protein.

Different embodiments of such an affinity ligand are discussed above in connection with the method aspects.

As a seventh aspect of the present disclosure, there is provided a use of an affinity ligand according to the sixth aspect as prognostic agent for colorectal cancer. Consequently, the affinity ligand may be used for establishing a prognosis for a colorectal cancer subject. Such use may for example be performed in vitro, e.g., involving the determination of the amount of PODXL in at least part of a sample earlier obtained from the subject.

The PODXL protein is expressed on the surfaces of colorectal tumor cells. Further, it is shown herein that the prognosis for survival of a subject having a colorectal cancer decreases with increased levels of PODXL protein expression in the tumor. The inventors thus conclude that PODXL is a therapeutic target in colorectal cancer and that an affinity ligand, such as an antibody, capable of binding the PODXL protein may be employed as a therapeutic agent.

The PODXL protein is reported to be involved in cell-cell adhesion. Without being bound to any specific scientific theory, targeting the PODXL protein of the colorectal tumor cells may interfere with the cell-cell interactions and thereby affect tumor growth and/or proliferation. Further, proteoglycans (PODXL is a proteoglycan) have been suggested to be involved in response to growth factors. Thus, targeting PODXL protein may also affect growth factor signaling, which is important for tumor growth.

Thus, as an eighth aspect of the present disclosure, there is provided an affinity ligand capable of selective interaction with a PODXL protein for use as a medicament. In particular, the affinity ligand may be for use in treatment of a subject having colorectal cancer.

According to one embodiment, a part of a colorectal tumor of the subject has been found to express PODXL protein, for example at a level which is higher than the average PODXL protein expression level of a relevant reference population of subjects having colorectal cancer. Alternatively, the part of the colorectal tumor may have been found to express PODXL protein at a level corresponding to a sample value which is higher than anyone of the reference values discussed above. Consequently, the affinity ligand may according to one embodiment only be for use in treatment of subjects having a tumor which has been found to express PODXL protein. The tumor in question may for example have been surgically removed before the PODXL expression status is established.

Also, according to one embodiment, the colorectal cancer of the eighth aspect is COX-2 positive according to any one of the above definitions.

Even though the therapeutic finding is not limited to any particular type of colorectal cancer, the connection between poor prognosis and PODXL expression has been shown specifically in colon cancer subjects (FIG. 7) and sigmoid colon cancer subjects (FIG. 1-5). The colorectal cancer of the eighth aspect may thus be a colon cancer. Further, the colon cancer may for example be sigmoid colon cancer.

The affinity ligand of the eighth aspect may be any one of the affinity ligands discussed in connection with the method aspects above as long as it is still capable of selective interaction with the PODXL protein.

According to an embodiment of the eighth aspect, the affinity ligand may thus be capable of selective interaction with the extracellular region of the PODXL protein (SEQ ID NO:6 or 7). SEQ ID NO:1, which is discussed further above, is a subregion of both splice variants the extracellular region of the PODXL protein (SEQ ID NO:6 and 7). Thus, according to an embodiment of the eighth aspect, the affinity ligand may be capable of selective interaction with a peptide consisting of the amino acid sequence SEQ ID NO:1.

A monoclonal antibody capable of selective interaction with SEQ ID NO:1, such as a specific epitope within SEQ ID NO:1, may for example be generated based on the hybridoma technology developed by Kohler and Milstein (Kohler, G and Milstein, C, 1973, Nature 256, 495-497). SEQ ID NO: 1 may be used as the antigen and its production is explained in Examples, section 1. An alternative approach is to synthesize a peptide consisting of an amino acid sequence within SEQ ID NO: 1, and use this peptide as the antigen. Antigen is injected subcutaneously into BALB/c mice (4-6 weeks old, female) at three-week intervals. Prior to immunization, the antigen is mixed with complete Freund's adjuvant for the first injection and incomplete Freund's adjuvant for the following injections. Three days before fusion, the mouse is challenged with antigen intravenously. Hybridomas are generated by fusion of splenocytes from the immunized mice with a Sp2/0 myeloma cell line. Then, several hybridoma cell lines are screened using ELISA, and cell lines that secrete antibodies specific for one or more fragment(s) consisting of an amino acid sequence within SEQ ID NO: 1 are identified and selected for further characterization.

Further characterization may include epitope mapping, which can be performed according to the following protocol based on bacterial display: DNA corresponding to SEQ ID NO:1 is amplified by PCR using vector pAff8c as template. The amplified DNA is fragmentized to various lengths (approximately 50-150 bp) by sonication, followed by ligation into the staphylococcal display vector (pSCEM2) and transformed into S. carnosus. In-frame DNA fragments are displayed as peptides on the staphylococcal surface. After incubation with antibody (selective for SEQ ID NO:1, obtained as described above) and fluorescently labeled secondary reagents, positive and negative cells are separately sorted using flow cytometry in order to isolate epitope and non-epitope presenting cells (Rockberg J et al (2008) Nature Methods vol 5. no 12: 1039-45). Isolated cells are sequenced by pyrosequencing and sequences finally aligned to the PODXL antigen for identification of epitopes. A dual-labeling strategy with real-time monitoring of the surface expression level may be used (Löfblom, J et al (2005) FEMS Microbiol Lett 248: 189-198). It allows for normalization of the binding signal with the expression level, provided low cell-to-cell variations and make discrimination of different epitope populations possible. Further, it also allows for a parallel assay to determine non-binding peptides displayed on the surface. An alternative approach to map the epitopes may be to perform a peptide screen according to the following protocol: A PEPscreen library (Sigma) consisting of biotinylated peptides corresponding to SEQ ID NO:1) on PODXL will then be synthesized. The peptides may be 15 amino acids long with a 10 amino acid overlap, together covering the entire PrEST-sequence. Neutravidin (Pierce, Rockford, Ill.) is then immobilized on carboxylated beads (COOH Microspheres, Luminex-Corp., Austin, Tex.) in accordance with the manufacturer's protocol. Coupling of beads is then performed using a filter membrane bottomed microtiter plate (MultiScreen-HTS, Millipore, Billerica, Mass.) as described by Larsson et al (Larsson et al (2009) J Immunol Methods 15; 34(1-2):20-32, Schwenk et al (2007) Mol Cell Proteomics 6(1) 125:32). Distinct groups of beads with different color code IDs is activated using 1-Ethyl-3-(3-dimethylaminopropyl) carbodiimide and N-Hydroxysuccinimide. Neutravidin (100 µg/ml in MES) is then added to the beads and incubated for 120 min on a shaker. The beads are then washed, re-suspended, and transferred to micro-centrifuge tubes for storage at 4° C. in a protein containing buffer (BRE, Blocking Reagent for ELISA, Roche, Basel, Switzerland) supplemented with NaN3. All coupled bead populations are treated with sonication in an ultrasonic cleaner (Branson Ultrasonic Corporation, Danbury, Conn.) for 5 min. The biotinylated peptides are diluted in BRE to a concentration of 20 µM, and 100 µl of each peptide is used in the coupling reaction, which is conducted for 60 min with shaking at RT. Finally, the beads are washed with 3×100 µl BRE buffer and stored at 4° C. until further use. The therapeutic properties of such monoclonal antibodies or a polyclonal antibody capable of selective interaction with (the extracellular region of) the PODXL protein may be assessed using the following protocol: Cells expressing the PODXL protein are seeded at $5 \times 10^4$ cells/well in 24-well dishes. After 24 h, cells are treated in triplicate with dilutions of antibody (selective for SEQ ID NO:1, obtained as described above) in concentrations ranging from 1 ng/ml to 1000 ng/ml. Cells treated with PBS pH 7.2 are used as controls. After 5 days, cells are trypsinized and counted three times each. Growth inhibition is calculated as percentage of cells compared with untreated cultures. The antibodies showing the highest growth inhibition may then be selected as the therapeutic antibodies. The person skilled in the art may thus, without undue burden, provide the affinity ligand of the eighth aspect using his general knowledge and the teachings of the present disclosure.

According to one embodiment, the affinity ligand is not part of a targeting composition according to PCT publication WO 2009/108932. Thus, according to one embodiment, the affinity ligand is not part of a composition further comprising a second antibody to carcinoembryonic antigen (CEA) or CD44v. According to an alternative or complementary embodiment, the affinity ligand is not bound to a solid substrate. According to another alternative or complementary embodiment, the affinity ligand is not part of a composition further comprising a therapeutic or imaging agent bound to the substrate or the affinity ligand. Here, the "therapeutic agent" refers to an agent which is different from the therapeutic affinity ligand of the present aspect. Examples of such a therapeutic agent are the chemotherapeutic agents listed in claim 28 of WO 2009/108932. The embodiments based on the disclosure of WO 2009/108932 described here in connection with the eighth aspect apply mutatis mutandis to the sixth and seventh aspect. Further, it is provided that the disclosure of WO 2009/108932 is based on a concept that is different from the concept on which the present disclosure is based. For example, the affinity ligands of the present disclosure are not intended for in vivo imaging. Also, the therapeutic effect of the present aspects does not rely on the actions of another therapeutic agent (e.g. a known chemotherapeutic agent which in itself is not capable of selective interaction with PODXL protein).

As a ninth aspect of the present disclosure, there is provided a method of treatment of a subject having a colorectal cancer comprising the step of administrating an effective amount of an affinity ligand capable of selective interaction with the PODXL protein. The embodiments of the eighth aspect apply to the ninth aspect mutatis mutandis.

It follows from the above that the level PODXL protein may be detected to determine whether a colorectal cancer patient would benefit from immunotherapy based on an anti-PODXL protein affinity ligand. However, it should be noted that the eighth and ninth aspects of the present disclosure are not limited to subjects showing (high levels of) PODXL expression.

As a tenth aspect of the present disclosure, there is thus provided a method of determining whether a mammalian subject having a colorectal cancer is likely to benefit from a treatment with an affinity ligand capable of selective interaction with a PODXL protein, comprising the steps of:
a) evaluating an amount of PODXL protein in at least part of a sample earlier obtained from the subject, and determining a sample value corresponding to the evaluated amount;
b) comparing said sample value from step a) with a predetermined reference value; and
if said sample value is higher than said reference value,
c) concluding that the subject is likely to benefit from the treatment.

Being likely to benefit from the treatment refers to a having a higher probability of survival or recovery if undergoing the treatment than if not undergoing the treatment. In this context, "recovery" refers to return from a colorectal cancer state to a colorectal cancer free state. The "survival" may be an overall survival or a disease free survival. Further, the "recovery" may be a recurrence free recovery. Also, the "higher probability" may be a probability benefit at five years, ten years or 15 years of at least 5%, such as at least 10%.

The embodiments of the eighth aspect apply to the present aspect mutatis mutandis. Further, the embodiments of the method aspects above apply mutatis mutandis to the present aspect.

Also, as an eleventh aspect of the present disclosure, there is provided a use of a PODXL protein, or an antigenically active fragment thereof, as an antigen in an immunization for the production of a therapeutic affinity ligand according to the eighth aspect. The PODXL protein may for example consist of the extracellular region (SEQ ID NO:6 or 7) or a subsequence thereof. It is to be understood that such a subsequence is of sufficient size to generate an affinity ligand capable of selective interaction with the PODXL protein. An example of a PODXL protein which is a subsequence of the extracellular region of PODXL is the peptide consisting of the amino acid sequence SEQ ID NO:1, which is generated in Examples, section 1 below and used as an antigen in Examples, section 2 below.

EXAMPLES

Generation of Mono-Specific Antibodies Against PODXL Protein and Use Thereof to Detect PODXL Protein in Colorectal Cancer Samples 1. Generation of Antigen
a) Materials and Methods A suitable fragment of the target protein encoded by the EnsEMBL Gene ID ENSG00000128567 was selected using bioinformatic tools with the human genome sequence as template (Lindskog M et al (2005) Biotechniques 38:723-727, EnsEMBL, www.ensembl.org). The fragment was used as template for the production of a 138 amino acid long fragment (SEQ ID NO:1) corresponding to amino acids 278-417 of the PODXL protein ENSP00000319782 (SEQ ID NO:2) or alternatively the amino acids 310-447 of the splice variant ENSP00000367817 (SEQ ID NO:3).

A fragment of the PODXL gene transcript containing nucleotides 832-1245 of EnsEMBL entry number ENST00000322985 (SEQ ID NO:4), or alternatively nucleotides 928-1341 of the splice variant ENST00000378555 (SEQ ID NO:5), was isolated by a Superscript™ One-Step RT-PCR amplification kit with Platinum® Taq (Invitrogen) and a human total RNA pool panel as template (Human Total RNA, BD Biosciences Clontech). Flanking restriction sites NotI and AscI were introduced into the fragment through the PCR amplification primers, to allow in-frame cloning into the expression vector (forward primer: CTGCCAGAGACCAT-GAGC (SEQ ID NO:8), reverse primer: GTCCCCTAGCT-TCATGTCAC (SEQ ID NO:9)). Then, the downstream primer was biotinylated to allow solid-phase cloning as previously described, and the resulting biotinylated PCR product was immobilized onto Dynabeads M280 Streptavidin (Dynal Biotech) (Larsson M et al (2000) J. Biotechnol. 80:143-157). The fragment was released from the solid support by NotI-AscI digestion (New England Biolabs), ligated into the pAff8c vector (Larsson M et al, supra) in frame with a dual affinity tag consisting of a hexahistidyl tag for immobilized metal ion chromatography (IMAC) purification and an immunopotentiating albumin binding protein (ABP) from streptococcal protein G (Sjölander A et al (1997) J. Immunol. Methods 201:115-123; Ståhl S et al (1999) Encyclopedia of Bioprocess Technology: Fermentation, Biocatalysis and Bioseparation (Fleckinger M C and Drew S W, eds) John Wiley and Sons Inc., New York, pp 49-63), and transformed into *E. coli* BL21(DE3) cells (Novagen). The sequences of the clones were verified by dye-terminator cycle sequencing of plasmid DNA amplified using TempliPhi DNA sequencing amplification kit (GE Healthcare, Uppsala, Sweden) according to the manufacturer's recommendations.

BL21(DE3) cells harboring the expression vector were inoculated in 100 ml 30 g/l tryptic soy broth (Merck KGaA) supplemented with 5 g/l yeast extract (Merck KGaA) and 50 mg/l kanamycin (Sigma-Aldrich) by addition of 1 ml of an overnight culture in the same culture medium. The cell culture was incubated in a 1 liter shake flask at 37° C. and 150 rpm until the optical density at 600 nm reached 0.5-1.5. Protein expression was then induced by addition of isopropyl-β-D-thiogalactopyranoside (Apollo Scientific) to a final concentration of 1 mM, and the incubation was continued overnight at 25° C. and 150 rpm. The cells were harvested by centrifugation at 2400 g, and the pellet was re-suspended in 5 ml lysis buffer (7 M guanidine hydrochloride, 47 mM $Na_2HPO_4$, 2.65 mM $NaH_2PO_4$, 10 mM Tris-HCl, 100 mM NaCl, 20 mM β-mercaptoethanol; pH=8.0) and incubated for 2 hours at 37° C. and 150 rpm. After centrifugation at 35300 g, the supernatant containing the denatured and solubilized protein was collected.

The $His_6$-tagged fusion protein was purified by immobilized metal ion affinity chromatography (IMAC) on columns with 1 ml Talon® metal ($Co^{2+}$) affinity resin (BD Biosciences Clontech) using an automated protein purification procedure (Steen J et al (2006) Protein Expr. Purif. 46:173-178) on an ASPEC XL4™ (Gilson). The resin was equilibrated with 20 ml denaturing washing buffer (6 M guanidine hydrochloride, 46.6 mM $Na_2HPO_4$, 3.4 mM $NaH_2PO_4$, 300 mM NaCl, pH 8.0-8.2). Clarified cell lysates were then added to the column. Thereafter, the resin was washed with a minimum of 31.5 ml washing buffer prior to elution in 2.5 ml elution buffer (6 M urea, 50 mM $NaH_2PO_4$, 100 mM NaCl, 30 mM acetic acid, 70 mM Na-acetate, pH 5.0). The eluted material was fractioned in three pools of 500, 700 and 1300 µl. The 700 µl fraction, containing the antigen, and the pooled 500 and 1300 µl fractions were stored for further use.

The antigen fraction was diluted to a final concentration of 1 M urea with phosphate buffered saline (PBS; 1.9 mM NaH$_2$PO$_4$, 8.1 mM Na$_2$HPO$_4$, 154 mM NaCl) followed by a concentration step to increase the protein concentration using Vivapore 10/20 ml concentrator with molecular weight cut off at 7500 Da (Vivascience AG). The protein concentration was determined using a bicinchoninic acid (BCA) micro assay protocol (Pierce) with a bovine serum albumin standard according to the manufacturer's recommendations. The protein quality was analyzed on a Bioanalyzer instrument using the Protein 50 or 200 assay (Agilent Technologies).

b) Results

A gene fragment corresponding to nucleotides 832-1245 or 928-1341 of the full-lengths transcript of PODXL (SEQ ID NO:4 or 5) was successfully isolated by RT-PCR from a human RNA pool using specific primers. The fragment codes for amino acids 278-415 and 310-447 of the two splice variants of the target protein PODXL (SEQ ID NO:2 and 3), respectively. The 138 amino acid fragment (SEQ ID NO:1) of the target protein (SEQ ID NO:2 or 3) was designed to lack transmembrane regions to ensure efficient expression in *E. coli*, and to lack any signal peptide, since those are cleaved off in the mature protein. In addition, the protein fragment was designed to consist of a unique sequence with low homology with other human proteins, to minimize cross reactivity of generated affinity reagents, and to be of a suitable size to allow the formation of conformational epitopes and still allow efficient cloning and expression in bacterial systems.

A clone encoding the correct amino acid sequence was identified, and, upon expression in *E. coli*, a single protein of the correct size was produced, and subsequently purified using immobilized metal ion chromatography. After dilution of the eluted sample to a final concentration of 1 M urea, and concentration of the sample to 1 ml, the concentration of the protein fragment was determined to be 4.0 mg/ml and was 98.2% pure according to purity analysis.

2. Generation of Antibodies a) Materials and Methods

The purified PODXL fragment as obtained above was used as antigen to immunize a rabbit in accordance with the national guidelines (Swedish permit no. A 84-02). The rabbit was immunized intramuscularly with 200 µg of antigen in Freund's complete adjuvant as the primary immunization, and boosted three times in four week intervals with 100 µg antigen in Freund's incomplete adjuvant.

Antiserum from the immunized animal was purified by a three-step immunoaffinity based protocol (Agaton C et al (2004) J. Chromatogr. A 1043:33-40; Nilsson P et al (2005) Proteomics 5:4327-4337). In the first step, 7 ml of total antiserum was buffered with 10×PBS to a final concentration of 1×PBS (1.9 mM NaH$_2$PO$_4$, 8.1 mM Na$_2$HPO$_4$, 154 mM NaCl), filtered using a 0.45 µm pore-size filter (Acrodisc®, Life Science) and applied to an affinity column containing 5 ml N-hydroxysuccinimide-activated Sepharose™ 4 Fast Flow (GE Healthcare) coupled to the dual affinity tag protein His$_6$-ABP (a hexahistidyl tag and an albumin binding protein tag) expressed from the pAff8c vector and purified in the same way as described above for the antigen protein fragment. In the second step, the flow-through, depleted of antibodies against the dual affinity tag His$_6$-ABP, was loaded at a flow rate of 0.5 ml/min on a 1 ml Hi-Trap NHS-activated HP column (GE Healthcare) coupled with the PODXL protein fragment used as antigen for immunization (SEQ ID NO:1). The His$_6$-ABP protein and the protein fragment antigen were coupled to the NHS activated matrix as recommended by the manufacturer. Unbound material was washed away with 1×PBST (1×PBS, 0.1% Tween20, pH 7.25), and captured antibodies were eluted using a low pH glycine buffer (0.2 M glycine, 1 mM EGTA, pH 2.5). The eluted antibody fraction was collected automatically, and loaded onto two 5 ml HiTrap™ desalting columns (GE Healthcare) connected in series for efficient buffer exchange in the third step. The second and third purification steps were run on the ÄKTAxpress™ platform (GE Healthcare). The antigen selective (mono-specific) antibodies (msAbs) were eluted with PBS buffer, supplemented with glycerol and NaN$_3$ to final concentrations of 40% and 0.02%, respectively, for long term storage at –20° C. (Nilsson P et al (2005) Proteomics 5:4327-4337).

The specificity and selectivity of the affinity purified antibody fraction were analyzed by binding analysis against the antigen itself and against 94 other human protein fragments in a protein array set-up (Nilsson P et al (2005) Proteomics 5:4327-4337). The protein fragments were diluted to 40 µg/ml in 0.1 M urea and 1×PBS (pH 7.4) and 50 µl of each were transferred to the wells of a 96-well spotting plate. The protein fragments were spotted in duplicate and immobilized onto epoxy slides (SuperEpoxy, TeleChem) using a pin-and-ring arrayer (Affymetrix 427). The slide was washed in 1×PBS (5 min) and the surface was then blocked (SuperBlock®, Pierce) for 30 minutes. An adhesive 16-well silicone mask (Schleicher & Schuell) was applied to the glass slide before the mono-specific antibodies were added (diluted 1:2000 in 1×PBST to appr. 50 ng/ml) and incubated on a shaker for 60 min. Affinity tag-specific IgY antibodies were co-incubated with the mono-specific antibodies in order to quantify the amount of protein in each spot. The slide was washed with 1×PBST and 1×PBS twice for 10 min each. Secondary antibodies (goat anti-rabbit antibody conjugated with Alexa 647 and goat anti-chicken antibody conjugated with Alexa 555, Molecular Probes) were diluted 1:60000 to 30 ng/ml in 1×PBST and incubated for 60 min. After the same washing procedure as for the first incubation, the slide was spun dry and scanned (G2565BA array scanner, Agilent). Thereafter images were quantified using image analysis software (GenePix 5.1, Axon Instruments).

b) Results

The quality of polyclonal antibody preparations has proven to be dependent on the degree of stringency in the antibody purifications, and it has previously been shown that depletion of antibodies directed against epitopes not originated from the target protein is necessary to avoid cross-reactivity to other proteins and background binding (Agaton C et al (2004) J. Chromatogr. A 1043:33-40). Thus, a protein microarray analysis was performed to ensure that mono-specific polyclonal antibodies of high specificity had been generated by depletion of antibodies directed against the His$_6$-tag as well as of antibodies against the ABP-tag.

To quantify the amount of protein in each spot of the protein array, a two-color dye labeling system was used, with a combination of primary and secondary antibodies. Tag-specific IgY antibodies generated in hen were detected with a secondary goat anti-hen antibody labeled with Alexa 555 fluorescent dye. The specific binding of the rabbit msAb to its antigen on the array was detected with a fluorescently Alexa 647 labeled goat anti-rabbit antibody. Each protein fragment was spotted in duplicates. The protein array analysis shows that the affinity purified mono-specific antibody against PODXL is highly selective to the correct protein fragment and has a very low background to all other protein fragments analyzed on the array.

3) Sigmoid Colon Cancer TMA a) Material and Methods

Archival formalin-fixed paraffin-embedded tissue from a patient cohort consisting of 305 retrospectively identified cases from a prospective database with patients who underwent curative resection for sigmoid colon cancer (148 women and 157 men) between 1993 and 2003 was collected from the Department of Pathology, Malmö University Hospital, Sweden. The median age of patients was 74 (39-97) years. 47 tumors were Dukes' stage A, 129 Dukes' stage B, 84 Dukes' stage C and 45 with Dukes' stage D. Some of the patients diagnosed with cancer with Duke's stage C or D tumor were offered adjuvant treatment (5-FU) or in some cases palliative treatment. Information regarding the date of death was obtained from the regional cause-of-death registries for all patients. Ethical permission was obtained from the Local Ethics Committee.

All 305 cases were histopathologically re-evaluated on slides stained with hematoxylin and eosin. TMA:s were then constructed by sampling 2×1.0 mm cores per case from areas representative of sigmoid colon carcinoma. Automated immunohistochemistry was performed as previously described (Kampf C et al (2004) Clin. Proteomics 1:285-300). In brief, the glass slides were incubated for 45 min in 60° C., de-paraffinized in xylene (2×15 min) and hydrated in graded alcohols. For antigen retrieval, slides were immersed in TRS (Target Retrieval Solution, pH 6.0, Dako, Copenhagen, Denmark) and boiled for 4 min at 125° C. in a Decloaking Chamber® (Biocare Medical). Slides were placed in the Autostainer® (Dako) and endogenous peroxidase was initially blocked with $H_2O_2$ (Dako). The slides were incubated for 30 min at room temperature with the primary PODXL antibody obtained as in Examples, section 2, or with an anti-COX-2 antibody. For COX-2 IHC, a monoclonal antibody (Zymed, clone 18-7379) diluted 1:200 was used. This was followed by incubation for 30 min at room temperature with goat anti-rabbit peroxidase conjugated Envision®. Between all steps, slides were rinsed in wash buffer (Dako). Finally, diaminobenzidine (Dako) was used as chromogen and Harris hematoxylin (Sigma-Aldrich) was used for counterstaining. The slides were mounted with Pertex® (Histolab).

All samples of immunohistochemically stained tissue were manually evaluated under the microscope and annotated by a certified pathologist. Annotation of each sample was performed using a simplified scheme for classification of IHC outcome. Each tissue sample was examined for representativity and immunoreactivity.

Basic annotation parameters included an evaluation of subcellular localization (nuclear expression and/or membranous/cytoplasmic expression), staining intensity and fraction of stained cells. Staining intensity was subjectively evaluated in accordance to standards used in clinical histo-pathological diagnostics and outcome was classified as: absent=no immunoreactivity, weak=faint immunoreactivity, moderate=medium immunoreactivity, or strong=distinct and strong immunoreactivity. Also fraction of stained cells was subjectively evaluated in accordance with standards used in clinical histo-pathological diagnostics and outcome was classified according to the percentage immunoreactive cells of the relevant cell population. The skilled artisan will recognize that this annotation procedure is similar to a calculation of an Allred score, see e.g. Allred et al (1998) Mod Pathol 11(2), 155.

For statistical analyses, levels of cytoplasmic intensity (CI) and cytoplasmic fraction (CF) were evaluated in line with what is described above. (As explained above, CI and CF are based on membranous/cytoplasmic expression.) Briefly, the subjects were split into four groups based on PODXL protein expression, wherein:

"0" represents an absent cytoplasmic intensity (CI) and a cytoplasmic fraction (CF) of <1%;

"1" represents a weak CI and a CF of >1%;

"2" represents a moderate or strong CI and a CF of 1-50%; and

"3" represents moderate or strong CI and a CF of >50%.

Based on the survival trends for individual strata, dichotomized variables were constructed for further statistical analyses. For analysis using the anti-PODXL protein antibody, two definitions of PODXL protein "high" and "low" were employed. In the first one, "PODXL protein high" represented "2" or "3" according to the above, while "PODXL protein low" represented "0" or "1" according to the above. In the second one, "PODXL protein high" represented "1", "2" or "3" according to the above, while "PODXL protein low" represented "0" according to the above. Consequently, two different cut-off:s were employed and when using the latter, substantially all subjects showing PODXL protein expression ended up in the "high" category.

Further, the subjects were split into two groups (high and low) based on COX-2 expression, wherein "high" represented a CF of ≥10% and a strong CI and "low" represented a CF of <10% and/or an absent, weak or moderate cytoplasmic intensity.

The above classification of samples was used to estimate disease free survival (DFS) and overall survival (OS) according to the Kaplan-Meier estimator, and the log-rank test was used to compare survival in different strata. All statistical tests were two-sided, and p-values of <0.05 were considered significant. All calculations were made with the statistical package SPSS 17.0 (SPSS Inc. Illinois, USA).

b) Results

Immunohistochemical analysis of PODXL expression could be performed on 279 tumor samples. The remaining cores either did not contain tumor cells or had been lost during histoprocessing. PODXL expression analysis resulted in a membranous/cytoplasmic staining in 86 subjects. 193 (69%) lacked expression (CI<1%).

Survival analysis of the entire cohort revealed that expression of PODXL in tumor tissues was significantly correlated with overall and disease free survival (OS and DFS) (FIGS. 1-5). FIGS. 1A and B shows OS and DFS for all subjects when divided into four different categories based on the CI. For patients with an absent or weak PODXL expression both OS and DFS were higher than for patients with a moderate or strong expression, with a five-year OS and DFS of approximately 60% and 70% respectively. OS and DFS for patients with moderate or strong expression of PODXL were approximately 40% (FIGS. 1A and 1B). Thus, a lower CI indicates a relatively good prognosis whereas a higher CI indicates a relatively poor prognosis. Analysis of OS and DFS with dichotomized variables further supports these findings (FIGS. 2A, 2B, 3A and 3B). Further, these figures show that OS and DFS analyses at both a relatively low (FIG. 3) and a relatively high (FIG. 2) cut-off yield significant results.

Figure 4B:
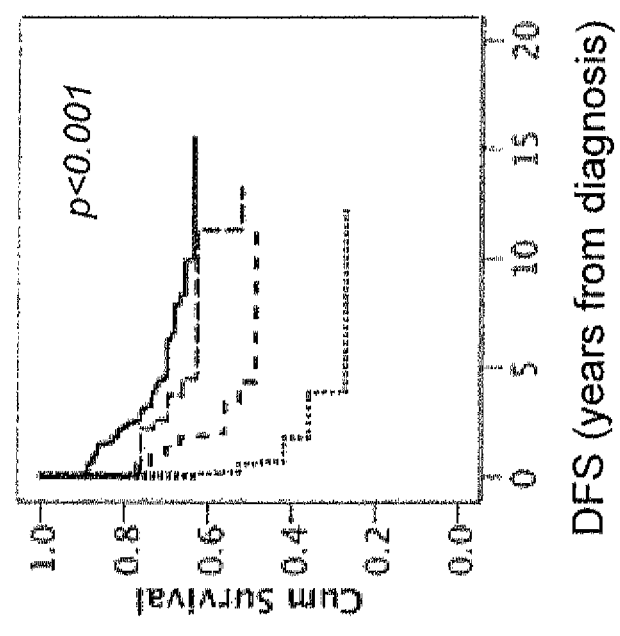
FIG. 4 shows the results of survival analysis of 279 subjects diagnosed with sigmoid colon cancer. Briefly, the subjects were split into four groups based on expression of PODXL protein and COX-2.
"0" represents subjects that are PODXL protein low and COX-2 low.
"1" represents subjects that are PODXL protein low and COX-2 high.
"2" represents subjects that are PODXL protein high and COX-2 low. Finally,
"3" represents subjects that are PODXL protein high and COX-2 high.
Figure 4A:
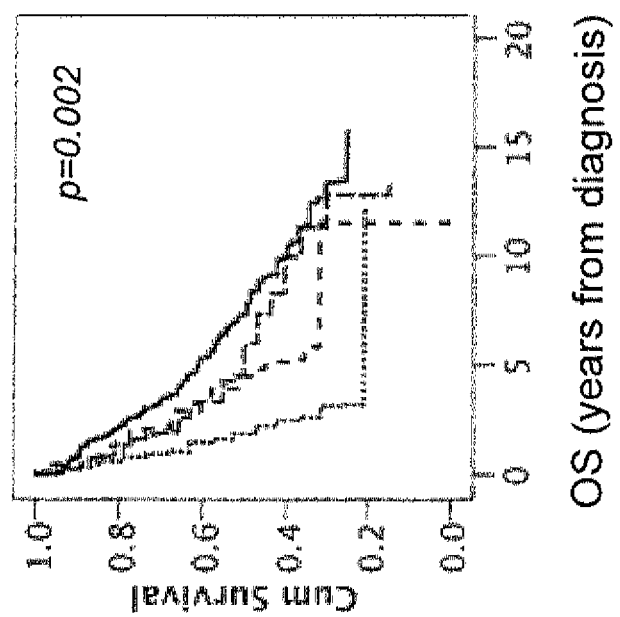

Next, the impact on DFS and OS of different combinations of PODXL protein expression and COX-2 expression was analyzed. Briefly, all subjects were split into four groups based on PODXL and COX-2 status, i.e. subjects that were PODXL low and COX-2 low, subjects that were PODXL low and COX-2 high, subjects that were PODXL high and COX-2 low and subjects that were PODXL high and COX-2 high. The analysis revealed that these strata were associated with differences in OS and DFS (FIGS. 4A and 4B). Surprisingly, PODXL high and COX-2 high patients had a particularly poor outcome whereas PODXL low and COX-2 low patients had a particularly good outcome. Further, PODXL protein is a more important prognostic marker than COX-2 according to FIG. 4. Analysis of OS and DFS with dichotomized variables, where one group consists of patients being PODXL low and/or COX-2 low and another group consists of patients being PODXL high and COX-2 high, further supports the differences in survival outcome (FIGS. 5A and 5B). This group of PODXL high patients may also be particularly interesting for COX-2 inhibition treatment.

In conclusion, for a patient diagnosed with sigmoid carcinoma, the use of PODXL protein as a biomarker may be of significant value for establishing a prognosis for a patient, e.g. the probability of survival, such as five-year survival, as can be seen in FIGS. 1 to 5. Further, the prognostic data may be refined by also considering the COX-2 status of the patient.

4) Colorectal Cancer TMA a) Material and Methods

Archival formalin-fixed paraffin-embedded tissue from 118 patients (61 women and 57 men) diagnosed with colorectal carcinoma between 1999 and 2002 was collected from the Department of Pathology, Malmö University Hospital, Sweden. The median age of patients was 73 (32-88) years. 51 of the samples were collected from colon and 67 from rectum. 35 tumors were Dukes' stage A, 42 Dukes' stage B, 35 Dukes' stage C and 6 Dukes' stage D. Information regarding the date of death was obtained from the regional cause-of-death registries for all patients. Ethical permission was obtained from the Local Ethics Committee.

All 118 cases of colorectal carcinoma were histopathologically re-evaluated on slides stained with hematoxylin and eosin. TMA:s were then constructed by sampling 2×1.0 mm cores per case from areas representative of invasive cancer. The TMA:s were prepared and automated immunohistochemistry was performed as described in section 3 above, using the PODXL antibody prepared as described in Examples, section 2 above and an anti-COX-2-monoclonal antibody (Zymed, clone 18-7379) diluted (1:200).

Annotation, classification, grouping and statistical analyses were performed as described in section 3a above. However, in the grouping based on COX-2 expression, "high" represented a CF of ≥10% and a moderate or strong CI and "low" represented a CF of <10% and/or an absent or weak (CI).

b) Results

Immunohistochemical analysis of PODXL expression could be performed on 112 tumor samples. The remaining cores either did not contain tumor cells or had been lost during histoprocessing. PODXL expression analysis resulted in a membranous/cytoplasmic staining in 67 subjects. 45 subjects (40%) lacked expression (CI<1%).

Survival analysis of the entire cohort revealed that membranous/cytoplasmic expression of PODXL in tumor tissues was significantly correlated with overall survival (OS) (FIGS. 6-7). FIG. 6A shows OS for all subjects when divided into four different categories based on the CI. Patients with an absent or weak PODXL expression had a higher OS than patients with a moderate or strong expression. Analysis of OS with dichotomized variables as seen in FIG. 6B reveal that the five-year OS for patients with absent or weak expression were above 60%, whereas the five-year OS for patients with moderate or strong expression were below 40%. Thus, a low CI indicates a relatively good prognosis whereas a high CI indicates a relatively poor prognosis. If excluding rectal samples from the OS analysis, the significant result remain, this finding further supports PODXL as an important marker for colon cancer aggressiveness (FIG. 7).

Next, the inventors investigated the association between the expression of PODXL and COX-2, given the proposed role for COX-2 as a predictor for poor prognosis in colon cancer. The impact on OS for patients with different combinations of PODXL protein expression and COX-2 expression were analyzed. Briefly, all subjects were split into four groups based on PODXL and COX-2 status, i.e. subjects that were PODXL low and COX-2 low, subjects that were PODXL low and COX-2 high, subjects that were PODXL high and COX-2 low and subjects that were PODXL high and COX-2 high. The analysis revealed that these defined strata were associated with differences in OS (FIG. 8A). Surprisingly, PODXL high and COX-2 high patients had a particularly poor outcome whereas PODXL low and COX-2 low patients had a particularly good outcome. Analysis of OS with dichotomized variables, where one group contains PODXL and/or COX-2 low patients and the second group consists of PODXL and COX-2 high patients, further supports the differences in survival outcome (FIG. 8B). This group of PODXL high patients may also be particularly interesting for COX-2 inhibition treatment.

Consequently, the results from the colorectal cancer cohort (the present section) are very similar to those from the sigmoid colon cancer cohort (section 3). The findings of the present disclosure thus indicate that PODXL protein, optionally in combination with COX-2, is a prognostically relevant biomarker in the whole colorectal region as well as in colon and a subregion thereof (i.e. the sigmoideum).

5) Colorectal Cancer TMA, Cohort II a) Material and Methods

Archival formalin-fixed paraffin-embedded tissue from 270 patients (137 women and 133 men), surgically treated for colorectal cancer between Jan. 1, 1990 and Dec. 31, 1991, was collected from the Department of Pathology, Malmö University Hospital, Sweden. The median age of patients was 73 (37-93) years. 217 of the samples were collected from colon and 51 from rectum. 42 tumors were Dukes' stage A, 118 Dukes' stage B, 70 Dukes' stage C and 40 Dukes' stage D. Information regarding the date of death was obtained from the regional cause-of-death registries for all patients. Ethical permission was obtained from the Local Ethics Committee.

All 270 cases of colorectal carcinoma were histopathologically re-evaluated on slides stained with hematoxylin and eosin. TMA:s were then constructed by sampling 2×1.0 mm cores per case from areas representative of invasive cancer. The TMA:s were prepared and automated immunohistochemistry was performed as described in section 3 above, using the PODXL antibody prepared as described in Examples, section 2 above.

Annotation, classification, grouping and statistical analyses were performed as described in section 3a above.

b) Results

Immunohistochemical analysis of PODXL expression could be performed on all 270 tumor samples. PODXL expression analysis resulted in a membranous/cytoplasmic staining in 121 subjects. 137 subjects (about 50%) lacked expression (CI<1%).

Survival analysis of the entire cohort revealed that membranous/cytoplasmic expression of PODXL in tumor tissues was significantly correlated with overall survival (OS) (FIG. 9). FIG. 9A shows OS for all subjects when divided into four different categories based on the CI. Patients with an absent or weak PODXL expression had a higher OS than patients with a moderate or strong expression. Analysis of OS with dichotomized variables as seen in FIG. 9B reveal that the five-year OS for patients with absent or weak expression (solid line) were approximately 50%, whereas the five-year OS for patients with moderate or strong expression (dotted line) were below 30%. Thus, a low CI indicates a relatively good prognosis whereas a high CI indicates a relatively poor prognosis.

When analyzing patients with highly differentiated tumors (FIG. 10A) there is a marked difference in OS between patients with an absent PODXL expression (solid line), who fared considerably better compared to those with tumors that stained positive for PODXL (dotted line).

When analyzing patients with Dukes stage A tumors (FIG. 10B) it can be seen that patients with absent or weak expression of PODXL (solid line) had a higher OS than patients with a moderate or strong expression (dotted line). The five-year survival for patients with low PODXL expression was almost 80%, while the five-year survival for patients expressing moderate to high PODXL levels, was only 40%.

The results from this colorectal cancer cohort (the present section) are thus similar to those from the other analyzed cohorts (sections 3 and 4).

6) Colorectal Cancer TMA, cohort III a) Materials and Methods

Cohort III consists of colorectal cancer (CRC) samples from the Malmö Diet and Cancer Study (MDCS), an ongoing population-based prospective cohort study with the primary aim to examine whether a Western diet rich in fat and low in fruit and vegetables increases the risk of certain forms of cancer (Berglund et al, 1993). Between 1991 and 1996, a total number of 28 098 individuals, 11 063 (39.4%) men and 17 035 (60.6%) women between 44 and 74 years where enrolled (from a background population of 74 138). Follow-up is done annually by record linkage to national registries for cancer and cause of death. Approval for the MDCS was obtained from the Ethics Committee at Lund University. Until the end of follow-up 31 Dec. 2008, 626 incident cases of CRC had been registered in the study population. Cases were identified from the Swedish Cancer Registry up until 31 Dec. 2007, and from The Southern Swedish Regional Tumor Registry for the period of 1 Jan. to 31 Dec. 2008. All tumors with available slides and/or paraffin blocks were histopathologically re-evaluated on haemotoxylin and eosin-stained slides. Histopathological, clinical and treatment data were obtained from clinical and/or pathology records. TNM staging was performed according to the American Joint Committee on Cancer (AJCC). Information on vital status and cause of death were obtained from the Swedish Cause of Death Registry up until 31 Dec. 2009. Follow-up started at the date of diagnosis and ended at death, emigration or 31 Dec. 2009, whichever came first.

Mean and median age of patients in the cohort was 71 years (range 50-86), and approximately 52% of the patients were female. Information on stage and grade was available for the majority of patients, T-stage ranging from 1-4 (appr. 60% of patients belonging to stage T3), N-stage ranging from 0-2 (appr. 60% to stage N0), and M-stage ranging from 0-1 (appr. 80% to stage M0). About 6% of patients had tumors with high differentiation grade, 70% with intermediate differentiation grade, and 22% with low differentiation grade. Information on adjuvant chemotherapy was also available for the majority of patients.

For TMA construction, tumors with an insufficient amount of material were excluded, and a total number of 557 (89%) tumors were used in the TMA. Areas representative of cancer were then marked on haematoxylin and eosin-stained slides and TMAs were constructed as previously described (Kononen et al, 1998). In brief, two 1.0 mm cores were taken from each tumor and mounted in a new recipient block using a semi-automated arraying device (TMArrayer, Pathology Devices, Westminster, Md., USA).

For immunohistochemical analysis, 4 mm TMA sections were automatically pre-treated using the PT-link system (DAKO, Glostrup, Denmark) and then stained in an Autostainer Plus(DAKO) with the affinity-purified polyclonal anti-PODXL antibody, obtained as described in Examples, Section 2 above, diluted 1:250. The Envision Flex/HRP (K8010) kit (DAKO) was used for visualisation of the staining. To control for heterogenous expression patterns, IHC was also performed on full-face sections from 10 randomly selected cases denoted as having negative PODXL expression and 10 cases with high (score 3-4) PODXL expression.

The PODXL protein was expressed in the cytoplasm of the tumor cells, with an accentuation towards the membrane in some cases. No expression was seen in the nuclei. The expression was recorded as negative (0), weakly positive in any proportion of cells (1), moderately positive in any proportion (2), positive with distinct membranous pattern in ≤50% of cells (3) and positive with distinct membranous pattern in >50% of cells (4). The staining was evaluated by two independent observers who were blinded to clinical and outcome data. Scoring differences were discussed in order to reach consensus.

For statistical purposes, categories of PODXL expression were trichotomised into negative (0), weak-moderate (1-2) and strong (3-4) PODXL staining, or dichotomised into low (0-2) and high (3-4) PODXL staining. Spearman's Rho and Chi-square-tests were used for comparison of PODXL expression and relevant clinicopathological characteristics. Kaplan-Meier analysis and log rank test were used to illustrate differences in colorectal cancer specific survival (CRCSS) and overall survival (OS) according to PODXL expression. Cox regression proportional hazards models were used for estimation of hazard ratios (HRs) for death from CRC and overall causes according to PODXL expression in both uni- and multivariate analysis, adjusted for age, gender, TNM status, differentiation grade and vascular invasion. A backward conditional selection method was used for variable selection by the model. The interaction between PODXL expression and adjuvant chemotherapy was explored by a Cox model including a treatment variable and an interaction variable. All tests were two-sided. A P-value of 0.05 was considered significant. All statistical analyses were performed using SPSS version 18 (SPSS Inc., Chicago, Ill., USA).

b) Results

Following antibody optimisation and staining, PODXL expression could be evaluated in 536 of the 557 (96.2%) of the tumors represented in the TMA. A total of 268 tumors (50.0%) were negative for PODXL, 196 (36.6%) displayed weak-moderate staining and 72 (13.4%) strong staining for PODXL. As endothelial cells express PODXL, entrapped vessels served as internal positive control. Notably, in the majority of cases denoted as positive, PODXL was distinctly expressed in scattered invasive cells at the tumor front, corresponding morphologically with tumor budding (Prall, 2007). PODXL expression in full-face sections (n=20) correlated with the TMA-based scoring in all cases. Analysis of the relationship between PODXL expression and established clinicopathological parameters revealed a strong correlation between high PODXL expression and more advanced T-stage (P<0.001), N-stage (P<0.001), M-stage (P=0.009), low differentiation grade (P<0.001) and presence of vascular invasion (P=0.008). There was no significant association between PODXL expression and age at diagnosis, gender or tumor location. Kaplan-Meier analysis revealed that PODXL expression correlated with a significantly shorter CRCSS and OS (FIG. 13), with the worst outcome for tumors with high PODXL expression (FIG. 13, line 3). These findings were confirmed in univariate Cox regression analysis using a dichotomised variable of low (0-2) and high (3-4) PODXL expression (HR=1.98; 95% confidence interval (CI) 1.38-2.84, P<0.001 for CRCSS and HR=1.85; 95% CI 1.29-2.64, P=0.001 for 5-year OS), and remained significant for 5-year OS in multivariate analysis (HR=1.52; 95% CI 1.03-2.25, P=0.036) and borderline significant for CRCSS(HR=1.57; 95% CI 0.99-2.18, P=0.055), adjusted for age, gender, TNM status, differentiation grade and vascular invasion. PODXL expression was also significantly associated with long-term OS, both in univariate analysis (HR=1.97; 95% CI 1.41-2.74, P<0.001) and multivariate analysis (HR=1.57; 95% CI 1.10-2.25, P=0.014).

Figure 14B:
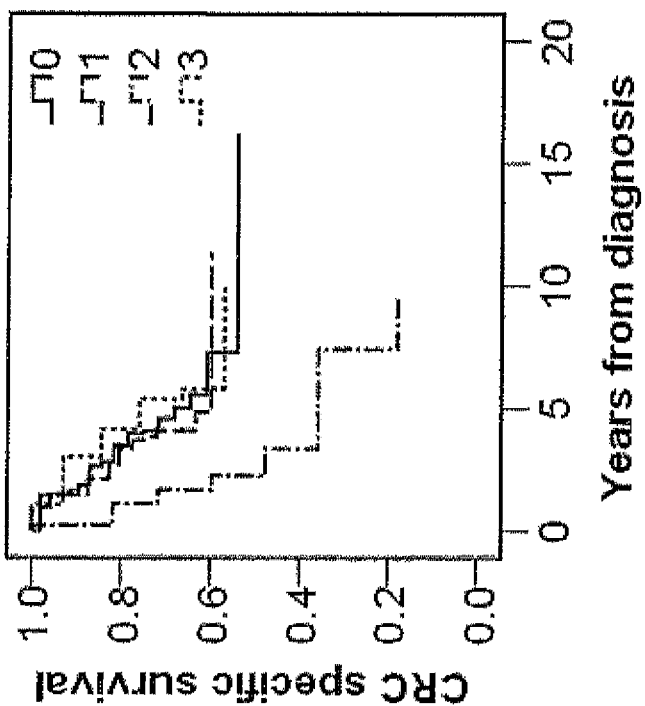
Figure 14A:
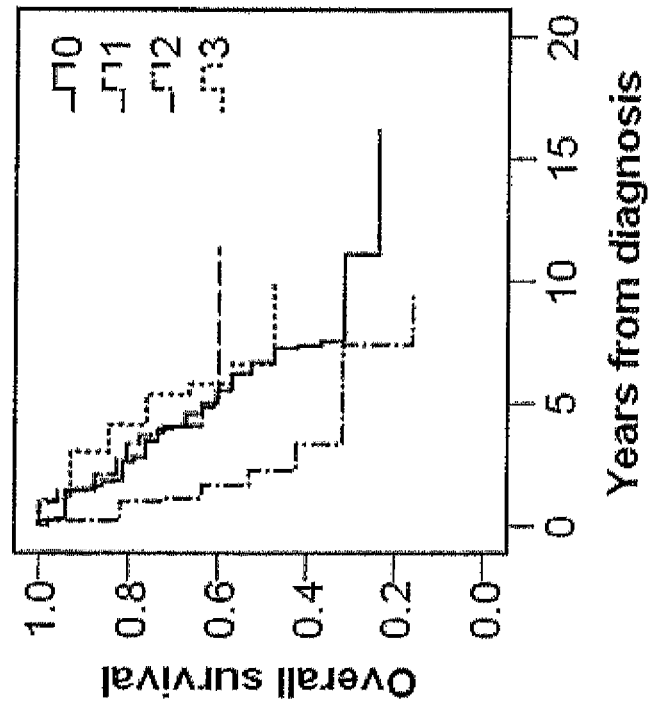

The impact of PODXL expression on survival in relation to adjuvant treatment was analysed in 122 curatively resected stage III (T1-4, N1-2, M0) patients, of whom 62 (50.8%) had received adjuvant treatment and 60 (49.2%) had not. Kaplan-Meier analysis in strata according to treatment and PODXL expression (FIG. 14) demonstrated that patients having tumors with high PODXL expression who were treated with adjuvant chemotherapy had a similar CRCSS (FIG. 14A, line 3) and OS (FIG. 14B, line 3) as patients with low PODXL-expressing tumors (FIG. 14, line 0 and 1). Untreated patients with tumors with high PODXL expression, however, had a significantly shorter CRCSS and OS (FIG. 14, line 2). Cox interaction analysis demonstrated that the P-value for the unadjusted interaction variable between treatment and PODXL status was 0.044 for 5-year OS, suggesting that patients having tumors with high expression of PODXL had benefited from adjuvant chemotherapy, whereas patients with low PODXL-expressing tumors did not benefit from adjuvant treatment. In addition, when adjusted for established prognostic factors, the term of interaction was significant for both CRCSS (P=0.004) and 5-year OS (P=0.015). The treatment benefit was similar for 5-fluorouracil alone or in combination with oxaliplatin. In patients with stage II disease (T3-4, N0, M0; n=205), high PODXL expression was associated with a significantly shorter OS(HR=3.03; 95% CI 1.45-6.34, P=0.003) and 5-year OS (HR=2.83; 95% CI 1.14-7.16, P=0.025), whereas the association with CRCSS did not reach significance (HR=2.19; 95% CI 0.84-5.75, P=0.11). Information on adjuvant chemotherapy was available for 170 patients with stage II disease, of whom only 13 (6.2%) had received treatment, an insufficient number to allow for analysis of a potential treatment benefit related to PODXL status in this group.

7) Colorectal Cancer TMA, Cohort IV
a) Materials and Methods

The colorectal cancer cohort IV consisted of 337 patients undergoing surgery for CRC at the Central District Hospital in Västerås, Sweden between June 2000 and December 2003. Tumor tissue for tissue microarray (TMA) construction was available from 320 (95%) patients. Follow-up started at date of diagnosis and ended at death or 15 Apr. 2010. Endpoints were defined according to Punt et al (*J Natl Cancer Inst* 2007. 99(13):998-1103). All observations were censored at loss to follow-up and at the end of the study period. Information on vital status and cause of death was obtained from the Regional Oncology Registry and hospital records. Histopathological, clinical, and treatment data were obtained from pathology and hospital records.

TMA construction and IHC staining was performed as described in Section 6 above, using the anti-PODXL antibody obtained as described in Section 2 above.

PODXL protein expression was recorded as negative (0), weakly positive in any proportion of cells (1), moderately positive in any proportion (2), positive with distinct membranous pattern in ≤50% of cells (3) and positive with distinct membranous pattern in >50% of cells (4). The staining was evaluated by two independent observers who were blinded to clinical and outcome data. Scoring differences were discussed in order to reach consensus.

For statistical purposes, categories of PODXL protein expression were dichotomized into low (0-2) and high (3-4) based on PODXL staining as described in Examples, Section 6 above. Spearman's Rho and Chi-square tests were used for comparison of PODXL expression and relevant clinicopathological characteristics. Kaplan-Meier analysis and log rank test were used to illustrate differences in disease free survival (DFS) and 5-year overall survival (OS) according to PODXL protein expression. Cox regression proportional hazards models were used for estimation of hazard ratios (HR) for DFS and TTR according to PODXL expression in both uni- and multivariable analysis adjusted for age, gender, TNM-status, differentiation grade, neural and vascular invasion. A backward conditional selection method was used for variable selection by the model. All tests were two sided. A p-value of 0.05 was considered significant. All statistical analyses were performed using SPSS version 19 (SPSS Inc, Chicago, Ill.).

b) Results

Following antibody optimization and staining, PODXL expression could be evaluated in 316/320 (98.8%) of tumors in the cohort. There were 291 (92.1%) tumors denoted as having low PODXL expression and 25 (7.9%) tumors with high expression.

High PODXL protein expression was associated with a more advanced T-stage (p=0.017), N-stage (p<0.001), M-stage (p<0.001), low differentiation grade (p=0.019) and presence of vascular (p=0.016) and neural invasion (p=0.002). There was no significant correlation between PODXL expression and age at diagnosis, gender, or tumor location.

Kaplan Meier analysis demonstrated that high PODXL protein expression was significantly associated with a shorter TTR and DFS in curatively treated patients. Cox univariate analysis confirmed this association with a shorter TTR (HR=2.93; 95% CI 1.26-6.82, p=0.013) and DFS (HR=2.44; 95% CI 1.32-4.54, p=0.005), remaining significant in multivariable analysis adjusted for age, gender, T- and N-status, differentiation grade, vascular and neural invasion, HR=2.50; 95% CI 1.05-5.96, p=0.038 for TTR and HR=2.11; 95% CI 1.13-3.94, p=0.019 for DFS.

8) Generation of Monoclonal Antibodies.
a) Materials and Methods

The purified fragment (SEQ ID NO:1) obtained in section 1 was used as antigen for production of monoclonal antibodies. Antigen was sent to AbSea Biotechnology Ltd (Beijing, China) and briefly, the antigen was injected subcutaneously into BALB/c mice (4-6 weeks old, female) at three week intervals. The antigen was mixed with complete Freund's adjuvant for the first injection and incomplete Freund's adjuvant for the following injections. Three days before fusion, the mouse was last challenged with antigen intravenously. Hybridomas were generated by fusion of mouse splenocytes with the Sp2/0 myeloma cell line. By screening several cell lines using ELISA, cells that secreted antibodies specific for the antigen (SEQ ID NO:1) were identified and delivered to Atlas Antibodies AB for further characterization. Cell lines that showed positive results in ELISA, Western blot (WB) and immunohistochemistry (IHC) were selected for subcloning, performed by AbSea Biotechnology Ltd.

In addition, the immunohistochemical staining patterns of the monoclonal antibodies were compared to that of the polyclonal anti-PODXL antibody generated in Section 2. This polyclonal antibody is sometimes referred to herein as "anti-PODXL".

b) Results

Cell-lines were screened by ELISA (at AbSea) to identify lines that produce monoclonal antibodies (mAbs) that recognize the antigen (SEQ ID NO:1), but not the affinity tag His-ABP. 22 cell-lines showed specific binding to the antigen SEQ ID NO:1 in ELISA and were selected for further testing. For each of the selected eight clones 150-300 µl supernatant was collected, azide was added, and the supernatants were delivered to Atlas Antibodies AB on wet ice. The supernatants were stored at +4° C. upon arrival according to the instructions from AbSea. Further testing of the cell lines resulted in the identification of three interesting cell lines, clones 8F6, 13C10 and 17C9, that gave positive results in both Western blot and IHC analysis. These clones were selected for subcloning and expansion, performed by AbSea Biotechnology Ltd.

9) Epitope Mapping Using Bioplex a) Synthetic Peptide Preparation

A PEPscreen library consisting of 26 biotinylated peptides corresponding to the protein fragment SEQ ID NO:1 of the PODXL protein (SEQ ID NO:2 or SEQ ID NO:3) was synthesized by Sigma-Genosys (Sigma-Aldrich). The peptides were 15 amino acids long with a 10 amino acid overlap, together covering the entire PrEST sequence (SEQ ID NO:1). The peptides were resolved in 80% DMSO to a final concentration of 10 mg/ml.

b) Bead Coupling

Neutravidin (Pierce, Rockford, Ill.) was immobilized on carboxylated beads (BioPlex COOH Beads, BioRad) in accordance to the manufacturer's protocol. Coupling of $10^6$ beads was performed using a filter membrane bottomed microtiter plate (MultiScreen-HTS, Millipore, Billerica, Mass.) as previously described (Larsson et al (2009) J Immunol Methods 15; 34(1-2):20-32, Schwenk et al (2007) Mol Cell Proteomics 6(1) 125:32). 26 distinct groups of beads with different color code IDs were activated using 1-Ethyl-3-(3-dimethylamino-propyl) carbodiimide and N-Hydroxysuccinimide. Neutravidin (250 µg/ml in 50 mM Hepes pH 7.4) was added to the beads and incubated for 120 min on a shaker. The beads were finally washed, re-suspended, and transferred to micro-centrifuge tubes for storage at 4° C. in PBS-BN (1×PBS, 1% BSA, 0.05% NaN3). The biotinylated peptides were diluted in PBS-BN to a concentration of 0.1 mg/ml, and 50 µl of each peptide was used in the coupling reaction, which was conducted for 60 min with shaking at RT. Finally, the beads were washed with 3×100 µl PBS-BN buffer and stored at 4° C. until further use.

c) Determination of Binding Specificity

A bead mixture containing all 26 bead IDs was prepared and 10 µl of rabbit anti-PODXL, obtained as described in section 2, was mixed with 30 µl of the bead mix and incubated for 60 min at RT. A filter bottomed microtiter plate (Millipore) was utilized for washing and following each incubation all wells were washed with 2×100 µl PBS-BN. To the beads, 25 µl of R-Phycoerythrine labeled anti-rabbit IgG antibody (Jackson ImmunoResearch) was added for a final incubation of 30 min at RT.

Measurements were performed using the Bioplex 200 Suspension Array instrumentation with Bio-Plex Manager 5.0 software. For each experiment, 50 events per bead ID were counted and the median fluorescence intensity (MFI) was used as a measurement of antibody binding to individual bead populations.

d) Results

The specificities of the polyclonal anti-PODXL antibody and the monoclonal anti-PODXL antibodies 8F6, 13C10 and 17C9 were tested in an assay using beads coupled with synthetic biotinylated peptides. The polyclonal anti-PODXL antibody showed binding to 11 of the peptides, namely 2, 3, 4, 5, 7, 8, 9, 18, 22, 24 and 25, corresponding to what can be regarded as six regions on the PrEST sequence (see FIG. 12). The first region (SEQ ID NO:10) corresponds to the overlap of peptides 2 and 3, the second region (SEQ ID NO:11) corresponds to the overlap of peptides 4 and 5, the third region (SEQ ID NO:12) corresponds to the overlap of peptides 7, 8, and 9, the fourth region (SEQ ID NO:13) corresponds to the peptide 18, the fifth region (SEQ ID NO:14) corresponds to the peptide 22 and the sixth region (SEQ ID NO:15) corresponds to the overlap of peptides 24 and 25. corresponding to five regions on the PrEST sequence.

The monoclonal antibodies 8F6, and 13C10 overlapped in specificity and both reacted with the peptide 22, corresponding to one distinct region on the PrEST sequence, sequence SEQ ID NO: 14 The monoclonal antibody 17C9 reacted with two peptides: 24 and 25, corresponding to one distinct region on the PrEST sequence, consensus sequence SEQ ID NO: 15.

10) Fractionation of the Polyclonal Anti-PODXL Antibody a) Materials and Methods Peptide specific antibodies were obtained by affinity purification of the polyclonal antibody against peptides to which the anti-PODXL antibody was shown to bind in Examples, section 9. Peptides 3, 7, 18, 22 and 24, corresponding to SEQ ID NO: 16, 17, 13, 14, and 18, respectively, were chosen, and 600 nmol of each biotinylated peptide were diluted with HiTrap™ Streptavidin binding buffer to a final volume of 1100 µl and applied to 1 ml HiTrap™ Streptavidin HP columns (GE Healthcare Bio-Sciences AB, Uppsala, Sweden) for binding. After coupling, columns were washed with HiTrap™ Streptavidin binding buffer to remove unbound peptides (and a blank run was performed on all columns prior to sample loading.)

Serum obtained from a New Zeeland white rabbit immunized with the recombinant PODXL fragment SEQ ID NO: 1 fused to a $His_6$-ABP tag, was purified on a ÄKTAxpress™ (GE Healthcare) liquid chromatography system on eight columns in a serial mode as follows: two 5 ml $His_6$-ABP columns followed by 5 epitope specific peptide columns and at the end a $His_6$-ABP-PODXL fusion protein column. After sample loading, the columns were washed and eluted in parallel to obtain separate antibody fractions. The eluted antibody fractions were epitope mapped using Bioplex, as described above.

b) Results

When fractions were epitope mapped, all fractionated antibodies bound their expected peptide. The fractions that bound peptides 7, 18, 22 and 24 were confirmed to bind the PODXL protein (SEQ ID NO:2 or SEQ ID NO:3) by IHC analysis. The fractions that bound peptides 3, 7, 22, and 24 were confirmed to bind the PODXL protein (SEQ ID NO:2 or SEQ ID NO:3) by Western Blot analysis.

12) Evaluation of Antibodies for IHC-Analysis of Colorectal Cancer Samples a) Material and Methods Tissue sections from Dukes stage C colorectal cancer samples, as well as samples from normal kidney (where PODXL is known to be expressed in glomeruli) were chosen for evaluation of six different primary antibodies. The antibodies evaluated were the mouse monoclonal anti-PODXL antibodies 8F6 (SEQ ID NO:14) and 17C9 (SEQ ID NO:15), a rabbit polyclonal anti-PODXL antibody from GeneTex, (catalogue no: GTX104764, obtained by using a peptide sequence within SEQ ID NO:19 as immunogen), a goat polyclonal anti-PODXL antibody from Abnova (catalogue no: PAB7292, obtained by using the peptide sequence SEQ ID NO:20 as immunogen), the polyclonal anti-PODXL antibody obtained as described in Section 2 above, and the fraction of the polyclonal anti-PODXL antibody binding peptide 24 (SEQ ID NO:18, obtained as described in Section 10 above). Automated immunohistochemistry was performed as previously described (Kampf C et al (2004) Clin. Proteomics 1:285-300). In brief, the glass slides were incubated for 45 min in 60° C., de-paraffinized in xylene (2×5 min+1×1 min) and hydrated in graded alcohols. During hydration, endogenous peroxidase was blocked with $H_2O_2$ (Merck). For antigen retrieval, slides were immersed in Citrate buffer pH 6 (PT Module Buffer 1, 100×-citrate buffer pH=6, Thermo Fisher Scientific) and boiled for 4 min at 125° C. in a Decloaking Chamber® (Biocare Medical). Slides were placed in the Lab Vision Autostainer 480® (Thermo Fisher Scientific) and incubated for 30 min at room temperature with the primary antibody. For goat and mouse primaries, slides were then incubated for 20-30 min at room temperature with either rabbit anti-goat secondary antibody (Rockland) for goat primaries, or Primary Antibody Enhancer (Thermo Fisher Scientific) for mouse primaries. All slides were then incubated with HRP Polymer (UltraVision LP detection system, Thermo Fisher Scientific)® for 30 min at room temp for all antibodies. Between all steps, slides were rinsed in wash buffer (ThermoFisher Scientific). Finally, diaminobenzidine (Thermo Fisher Scientific) was used as chromogen and Mayer's hematoxylin (Histolab) was used for counterstaining. The slides were mounted with Pertex® (Histolab).

All images of immunohistochemically stained tissue were manually evaluated under the microscope.

b) Results

The staining patterns were ranked by two independent experts in the field in a blind set-up for each of the tissue samples stained. The antibodies/stainings were ranked based on how distinct the staining was, and they were assigned a score from 1 to 6 with the most distinct staining pattern corresponding to the highest score. Thus, the least distinct staining pattern corresponded to a score of 1. A total score was then obtained for each tissue type (colorectal cancer and normal kidney) by adding the scores from the two independent experts for each of the antibodies. An overall score was then obtained for each of the antibodies by adding the total scores from each tissue type (see the Table). The monoclonal antibody 8F6 received the highest overall score, followed by the polyclonal anti-PODXL antibody, demonstrating that antibodies binding to SEQ ID NO:14 are superior for use in IHC compared to the other antibodies in the experiment, among those, antibodies binding to SEQ ID NO:15.

TABLE

| Antibody | Score 1 Kidney | Score 2 CRC | Overall score |
|---|---|---|---|
| 8F6 | 12 | 10 | 22 |
| 17C9 | 6 | 5 | 11 |
| GTX104764 | 2 | 2 | 4 |
| PAB7292 | 4 | 7 | 11 |
| anti-PODXL | 9 | 11 | 20 |
| Fraction binding peptide 24 | 9 | 7 | 16 |

13) In Vitro Binding of Antibodies to the Surface of Living Cells a) Materials and Methods The binding the polyclonal antibody, obtained as described in section 2, to cultured colon cancer cells in vitro was determined by LigandTracer Green (Rigeview Instruments AB, Uppsala, Sweden) measurements. The cell line used in the experiments was the colon cancer cell line CACO-2. Cells were grown in complete media supplemented with 20% fetal calf serum (Sigma, Germany), L-glutamine (2 mM) and PEST (penicillin 100 IU/ml, and streptomycin 100 µg/ml). The antibody was labeled with an amine-reactive TexasRed dye, and circular cell dishes with a large amount of CACO-2 cells were used in the assay. The TexasRed labeling procedure was performed as follows: The smallest amount of TexasRed that could be transferred from the stock vial was dissolved in 100 µl DMSO. A volume of 20 µl TexasRed solution was then mixed with 100 µl borate buffer pH9, approximately 20 µg antibody, and incubated for 60 minutes in room temperature. Free dye molecules were removed using a NAP-5 column.

The LigandTracer Green assay comprised one circular cell dish with CACO-2 seeded in a local portion of the cell dish. Labeled antibody was added, typically in the nM concentration range in two or more steps. The resulting binding traces shows if binding has taken place or not. TexasRed-labeled human serum albumin (HSA) (labeled with a much higher number of dye molecules per HSA) was used as negative control, and as positive control, the commercially available anti-PODXL antibody 3D3 (Santa Cruz Biotechnology, catalogue no: sc-23904) was used.

To confirm the results from the LigandTracer assay, manual binding studies were conducted in multi-well cell-culture dishes. Antibodies were radiolabeled with $^{125}I$ using the chloramine-T method. Briefly, $^{125}I$ was added to 40 µg of antibody in PBS and 10 µl chloramine-T (2 mg/ml in PBS, Sigma, USA) was added. After 60 s incubation the reaction was stopped by adding 25 µl sodium metabisulphite (2 mg/ml in PBS, Sigma, USA). Labeled antibody was separated from low molecular weight compounds using a NAP-5 column (cut-off 5 kDa, Amersham Biosciences, Uppsala, Sweden) equilibrated with PBS. Radiolabeled antibody was added to cells, sometimes supplemented with a high concentration of unlabeled antibody, and was then incubated for at least 4 hours. After incubation, the cells were washed quickly 4 times, released by trypsination, counted (#cells/ml) and quantified for radioactivity (Bq/ml) in a Wallac 1480 Wizard gamma counter (Turku, Finland). As positive control, the commercially available anti-PODXL antibody 3D3 (Santa Cruz Biotechnology, catalogue no: sc-23904) was used, and as negative control, a monoclonal IgG2a antibody against Troponin was used.

b) Results

The polyclonal anti-PODXL antibody was shown to bind to living colon cancer cells in vitro (FIG. 11). A concentration depentent binding of anti-PODXL to CACO-2 cells can be seen, with an increased binding, reflected by a clear increase in signal intensity, when exposing the cells to an increased concentration of anti-PODXL antibody. The manual binding studies confirmed the results from the LigandTracer assay using positive and negative controls (results not shown).

Establishment of a Prognosis for a Colon Cancer Patient

14) A Non-Limiting Example

A cancer patient can present with symptoms or signs from tumor growth, focal symptoms including pain and distress from the region where the tumor grows or more general symptoms such as weight loss and fatigue. Signs from growth of a colorectal tumor can also become evident through blood in feces and/or dysfunction, e.g. diarrhea/constipation.

The description below refers to the case where the colorectal cancer is located in the sigmoid colon.

Following the establishment of a sigmoid colon cancer diagnosis in a patient, a tumor tissue sample is obtained. The tumor tissue sample may be obtained from a biopsy performed earlier during the diagnosis of the cancer or from a specimen from an earlier surgical removal of the tumor. Further, for the provision of a "negative reference", a sample is taken from archival material comprising tissue having low, or essentially lacking, PODXL protein expression. Such archival tissue may for example be sigmoid colon tumor tissue having a pre-established low PODXL protein expression level. Further, for the provision of a "positive reference", a sample is taken from archival material comprising tissue having high PODXL protein expression, such as sigmoid colon tumor tissue having a pre-established high PODXL protein expression level.

The sample material is fixated in buffered formalin and histo-processed in order to obtain thin sections (4 μm) of the of the sample material.

Immunohistochemistry is performed as described in Examples, Section 3. One or more sample sections from each sample is/are mounted on glass slides that are incubated for 45 min in 60° C., de-paraffinized (if the sample in question was paraffinized) in xylene (2×15 min) and hydrated in graded alcohols. For antigen retrieval, slides are immersed in TRS (Target Retrieval Solution, pH 6.0, DakoCytomation) and boiled for 4 min at 125° C. in a Decloaking Chamber® (Biocare Medical). Slides are placed in the Autostainer® (DakoCytomation) and endogenous peroxidase is initially blocked with $H_2O_2$ (DakoCytomation). The reason for mounting multiple sample sections is to increase the accuracy of the results.

A primary PODXL protein specific antibody is added to the slides and incubated for 30 min in room temperature, followed by 30 min of incubation in room temperature with a labeled secondary antibody; e.g. goat-anti-rabbit peroxidase conjugated Envision®. The primary antibody may for example be produced as described in Examples, section 2 above. To detect the secondary antibody, diaminobenzidine (DakoCytomation) is used as chromogen, contrasted with a Harris hematoxylin (Sigma-Aldrich) counterstaining. Between all steps, slides are rinsed in wash buffer (DakoCytomation). The slides are then mounted with Pertex® (Histolab) mounting media.

As a tool to validate the staining procedure, two control cell-lines may be used; e.g. one slide with cells expressing PODXL protein (positive cell line) and one slide having cells with indistinct weak or no PODXL protein expression (negative cell line). The skilled artisan understands how to provide such cell lines, for example guided by the disclosure of Rhodes et al. (2006) The biomedical scientist, p 515-520. The control-line slides may be simultaneously stained in the same procedure as the colorectal cancer slides, i.e. incubated with the same primary and secondary antibodies.

For example, the sigmoid colon tumor slides, the staining reference slides, and optionally, the slides with control cell-lines, may be scanned in a light microscope using a ScanScope T2 automated slide scanning system (Aperio Technologies) at ×20 magnification. However, this scanning step is not necessary, but may make the procedure easier if, for example, the preparation and staining of the slides and the evaluation of the stained slides (see below) are performed at different locations or by different persons.

If control cell-lines are used, these are inspected to validate the staining procedure. If the cell-lines display staining results outside acceptable criteria, e.g. staining artifacts recognized by the skilled artisan, the staining of the biopsy samples is considered invalid and the whole staining procedure is repeated with new slides. If the positive and negative cell-lines display strong staining intensity and indistinct weak or no staining intensity, respectively, the staining is considered as valid.

The stained sample slide(s) from the tumor tissue is/are evaluated manually by visual inspection in accordance to standards used in clinical histo-pathological diagnostics, and the immunoreactivity of the colorectal cancer slide(s) is/are graded as described in Examples, Section 3.

That is, the cytoplasmic intensity (CI) and the cytoplasmic fraction (CF) are examined.

In the determination of the CI and CF, the person performing the evaluation and grading is aided by visual inspection of the stained reference slides, i.e. the "positive reference" and the "negative reference".

Each sample is then assigned a sample value on the scale 0-3, wherein:
"0" represents an absent CI and a CF of <1%;
"1" represents a weak CI and a CF of >1%;
"2" represents a moderate or strong CI and a CF of 1-50%; and
"3" represents moderate or strong CI and a CF of >50%.

The sample value(s) is/are then compared to a reference value.

The reference value may be "0" or "1", preferably "1".

Figure 2B:
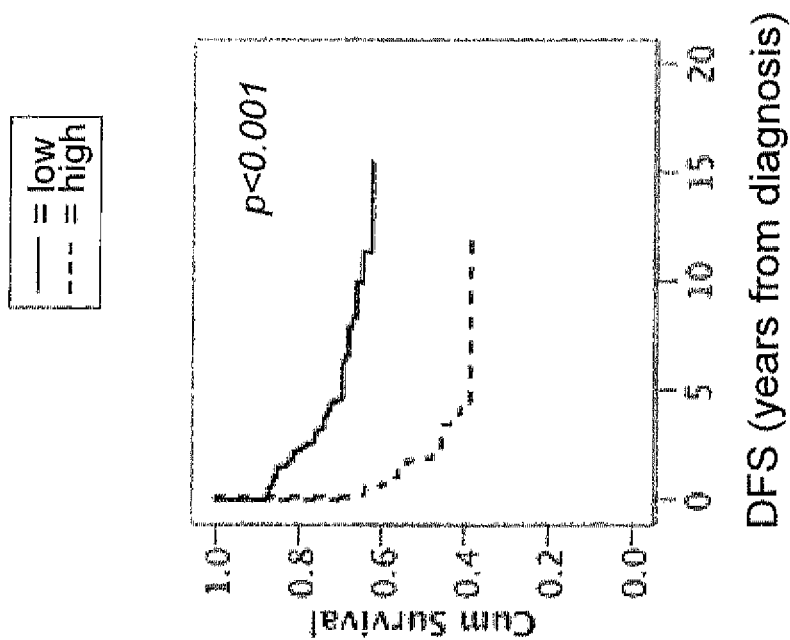
FIG. 2 shows the results of survival analysis of 279 subjects diagnosed with sigmoid colon cancer. Briefly, the subjects were split into two groups based on PODXL protein expression, wherein "low" represents "0" or "1" according to FIG. 1 and "high" represents "2" or "3" according to FIG. 1.
FIG. 2A shows OS and 2B shows DFS.
Figure 2A:
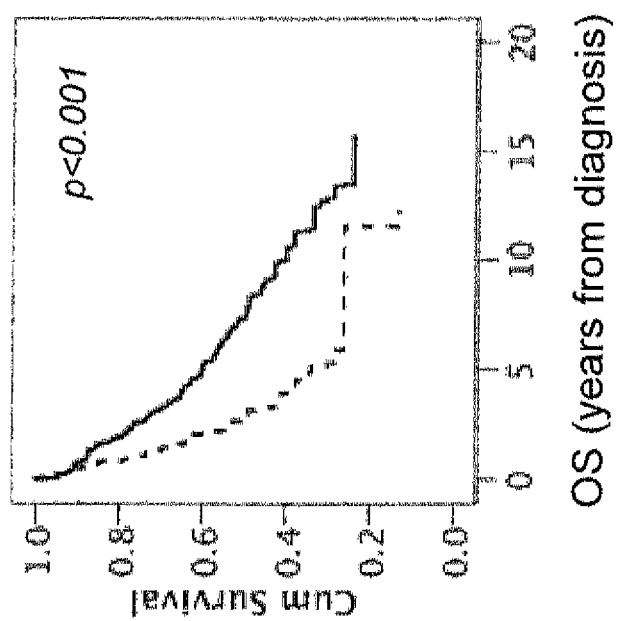

If the sample value(s) or a sample value average is/are equal to or lower than the reference value "1", it is concluded that the subject belongs to a group having a relatively good prognosis. FIG. 2 shows that the relatively good prognosis may be an overall five-year survival of about 60% (FIG. 2A, solid line) or a disease free five-year survival of about 69% (FIG. 2B, solid line).

If however the sample value(s) or a sample value average is/are higher than the reference value "1", it is concluded that the subject belongs to a group having a relatively poor prognosis. FIG. 2 shows that the relatively poor prognosis may be an overall five-year survival of about 34% (FIG. 2A, dashed line) or a disease free five-year survival of about 38% (FIG. 2B, dashed line).

Further, a primary COX-2 protein specific antibody (e.g. Zymed, clone 18-7379) may be added to slides from the same samples according to the staining and evaluation protocol outlined above.

Each sample stained with the anti-COX-2 antibody is then given a sample value selected from "high" and "low", wherein:
"high" represents a CF of ≥10% and a strong CI; and
"low" represents a CF of <10% and/or an absent, weak or moderate cytoplasmic intensity.

Here, the implicit reference value is "low".

If the COX-2 sample value(s) or a COX-2 sample value average is/are "low", it is concluded that the subject belongs to a subgroup having a relatively good prognosis.

If however the COX-2 sample value(s) or a COX-2 sample value average is/are "high", it is concluded that the subject belongs to a subgroup having a relatively good prognosis.

The prognosis based on the PODXL status may thus be detailed by also looking at the COX-2 status.

FIG. 4 shows that if the subject that has the lower PODXL sample value(s) is COX-2 low, the probability of five-year overall survival and disease free survival may be about 62% (FIG. 4A) and about 70% (FIG. 4B), respectively. However, if the subject that has the lower PODXL sample value(s) is COX-2 high, the probability of five-year overall survival and disease free survival may be about 50% (FIG. 4A) and about 63% (FIG. 4B), respectively.

Further, FIG. 4 shows that if the subject that has the higher PODXL sample value(s) is COX-2 low, the probability of five-year overall survival and disease free survival may be about 44% (FIG. 4A) and about 49% (FIG. 4B), respectively. However, if the subject that has the higher PODXL sample value(s) is COX-2 high, the probability of five-year overall survival and disease free survival may be about 21% (FIG. 4A) and about 28% (FIG. 4B), respectively.

The prognosis may then form a basis for further decisions relating to the treatment, or non-treatment, of the patient. For example, if the patient is shown to belong to the group having relatively high PODXL values and thus a relatively poor prognosis, particularly in combination with a high COX-2 expression level, the decision may be to apply a "more aggressive chemotherapy treatment" than what otherwise would have been considered.

Alternatively, the prognosis may form basis for further decisions relating to the treatment, or non-treatment, of the patient. For example, if the patient is shown to belong to the group having relatively high PODXL values and thus a relatively poor prognosis, the decision may be to apply immunotherapy using an anti-PODXL antibody.

All cited material, including but not limited to publications, DNA or protein data entries, and patents, referred to in this application are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. Method of treatment of a human subject having a TNM stage II or Dukes' stage B colorectal cancer, comprising:
   a) evaluating an amount of PODXL protein present in at least part of a colorectal tumor tissue sample from the subject using immunohistochemistry (IHC) and determining a sample value corresponding to the evaluated amount;
   b) comparing the sample value obtained in step a) with a reference value; and, if said sample value is higher than said reference value,
   c) treating said subject with adjuvant chemotherapy; and if said sample value is lower than or equal to said reference value,
   d) refraining from treating said subject with adjuvant chemotherapy,
wherein the evaluation of step a) is limited to the membranes of tumor cells of said sample, wherein step a) comprises:
   aI) applying to said sample of step a) a quantifiable affinity ligand capable of selective interaction with the PODXL protein to be evaluated, said application being performed under conditions that enable binding of the affinity ligand to PODXL protein present in the sample; and
   aII) quantifying the affinity ligand bound to said sample to evaluate said amount,
wherein said quantifiable affinity ligand is a monoclonal antibody or a Fab fragment, Fv fragment or scFv fragment thereof capable of selective interaction with a peptide consisting of the amino acid sequence SEQ ID NO:14.

2. Method according to claim 1, wherein the evaluation of step a) is limited to the membranes of tumor budding cells of said sample.

3. Method of treatment of a human subject having a TNM stage III or Dukes' stage C colorectal cancer, comprising:
   a) evaluating an amount of PODXL protein present in at least part of a colorectal tumor tissue sample from the subject using immunohistochemistry (IHC) and determining a sample value corresponding to the evaluated amount;
   b) comparing the sample value obtained in step a) with a reference value; and,
   if said sample value is higher than said reference value,
   c) treating said subject with adjuvant combination chemotherapy; and
   if said sample value is lower than or equal to said reference value,
   d) refraining from treating said subject with adjuvant combination chemotherapy, wherein the evaluation of step a) is limited to the membranes of tumor cells of said sample, wherein step a) comprises:
   aI) applying to said sample of step a) a quantifiable affinity ligand capable of selective interaction with the PODXL protein to be evaluated, said application being performed under conditions that enable binding of the affinity ligand to PODXL protein present in the sample; and
   aII) quantifying the affinity ligand bound to said sample to evaluate said amount,
wherein said quantifiable affinity ligand is a monoclonal antibody or a Fab fragment, Fv fragment or scFv fragment thereof capable of selective interaction with a peptide consisting of the amino acid sequence SEQ ID NO:14.

4. Method according to claim 3, wherein the evaluation of step a) is limited to the membranes of tumor budding cells of said sample.

5. Method of treatment of a human subject having a TNM stage III or Dukes' stage C colorectal cancer, comprising:
   a) evaluating an amount of PODXL protein present in at least part of a colorectal tumor tissue sample from the subject using immunohistochemistry (IHC) and determining a sample value corresponding to the evaluated amount;
   b) comparing the sample value obtained in step a) with a reference value; and,
   if said sample value is higher than said reference value,
   c) treating said subject with a more aggressive adjuvant chemotherapy; and
   if said sample value is lower than or equal to said reference value,
   d) treating said subject with a less aggressive adjuvant chemotherapy,
   wherein the less aggressive adjuvant chemotherapy involves the application of fewer chemotherapeutic agents or a chemotherapeutic substance in a lower dose as compared to the more aggressive adjuvant chemotherapy,
wherein the evaluation of step a) is limited to the membranes of tumor cells of said sample, wherein step a) comprises:

aI) applying to said sample of step a) a quantifiable affinity ligand capable of selective interaction with the PODXL protein to be evaluated, said application being performed under conditions that enable binding of the affinity ligand to PODXL protein present in the sample; and aII) quantifying the affinity ligand bound to said sample to evaluate said amount, wherein said quantifiable affinity ligand is a monoclonal antibody or a Fab fragment, Fv fragment or scFv fragment thereof capable of selective interaction with a peptide consisting of the amino acid sequence SEQ ID NO:14.

6. Method according to claim 5, wherein the evaluation of step a) is limited to the membranes of tumor budding cells of said sample.

* * * * *

UNITED STATES PATENT AND TRADEMARK OFFICE
CERTIFICATE OF CORRECTION

PATENT NO. : 8,999,656 B2
APPLICATION NO. : 13/456354
DATED : April 7, 2015
INVENTOR(S) : Jirström et al.

It is certified that error appears in the above-identified patent and that said Letters Patent is hereby corrected as shown below:

In the Specification:
Column 1, Line 5: Please correct "PCT/EP2010/0066168,"
to read -- PCT/EP2010/066168, --

Column 54, Line 43: Please correct "C11.26-6.82,"
to read -- CI 1.26-6.82 --

Signed and Sealed this
Fifth Day of January, 2016

Michelle K. Lee
*Director of the United States Patent and Trademark Office*

SEQUENCE LISTING

```
<160> NUMBER OF SEQ ID NOS: 20

<210> SEQ ID NO 1
<211> LENGTH: 138
<212> TYPE: PRT
<213> ORGANISM: Homo sapiens

<400> SEQUENCE: 1

Leu Pro Glu Thr Met Ser Ser Ser Pro Thr Ala Ala Ser Thr Thr His
1               5                   10                  15

Arg Tyr Pro Lys Thr Pro Ser Pro Thr Val Ala His Glu Ser Asn Trp
            20                  25                  30

Ala Lys Cys Glu Asp Leu Glu Thr Gln Thr Gln Ser Glu Lys Gln Leu
        35                  40                  45

Val Leu Asn Leu Thr Gly Asn Thr Leu Cys Ala Gly Gly Ala Ser Asp
    50                  55                  60

Glu Lys Leu Ile Ser Leu Ile Cys Arg Ala Val Lys Ala Thr Phe Asn
65                  70                  75                  80

Pro Ala Gln Asp Lys Cys Gly Ile Arg Leu Ala Ser Val Pro Gly Ser
                85                  90                  95

Gln Thr Val Val Val Lys Glu Ile Thr Ile His Thr Lys Leu Pro Ala
                100                 105                 110

Lys Asp Val Tyr Glu Arg Leu Lys Asp Lys Trp Asp Glu Leu Lys Glu
            115                 120                 125

Ala Gly Val Ser Asp Met Lys Leu Gly Asp
        130                 135

<210> SEQ ID NO 2
<211> LENGTH: 526
<212> TYPE: PRT
<213> ORGANISM: Homo sapiens

<400> SEQUENCE: 2

Met Arg Cys Ala Leu Ala Leu Ser Ala Leu Leu Leu Leu Leu Ser Thr
1               5                   10                  15

Pro Pro Leu Leu Pro Ser Ser Pro Ser Pro Ser Pro Ser Pro Ser Gln
            20                  25                  30

Asn Ala Thr Gln Thr Thr Thr Asp Ser Ser Asn Lys Thr Ala Pro Thr
        35                  40                  45

Pro Ala Ser Ser Val Thr Ile Met Ala Thr Asp Thr Ala Gln Gln Ser
```

```
                    50                  55                  60
Thr Val Pro Thr Ser Lys Ala Asn Glu Ile Leu Ala Ser Val Lys Ala
 65                  70                  75                  80

Thr Thr Leu Gly Val Ser Ser Asp Ser Pro Gly Thr Thr Leu Ala
                     85                  90                  95

Gln Gln Val Ser Gly Pro Val Asn Thr Thr Val Ala Arg Gly Gly Gly
                100                 105                 110

Ser Gly Asn Pro Thr Thr Thr Ile Glu Ser Pro Lys Ser Thr Lys Ser
                115                 120                 125

Ala Asp Thr Thr Thr Val Ala Thr Ser Thr Ala Thr Ala Lys Pro Asn
130                 135                 140

Thr Thr Ser Ser Gln Asn Gly Ala Glu Asp Thr Thr Asn Ser Gly Gly
145                 150                 155                 160

Lys Ser Ser His Ser Val Thr Thr Asp Leu Thr Ser Thr Lys Ala Glu
                165                 170                 175

His Leu Thr Thr Pro His Pro Thr Ser Pro Leu Ser Pro Arg Gln Pro
                180                 185                 190

Thr Ser Thr His Pro Val Ala Thr Pro Thr Ser Ser Gly His Asp His
                195                 200                 205

Leu Met Lys Ile Ser Ser Ser Ser Thr Val Ala Ile Pro Gly Tyr
210                 215                 220

Thr Phe Thr Ser Pro Gly Met Thr Thr Thr Leu Pro Ser Ser Val Ile
225                 230                 235                 240

Ser Gln Arg Thr Gln Gln Thr Ser Ser Gln Met Pro Ala Ser Ser Thr
                245                 250                 255

Ala Pro Ser Ser Gln Glu Thr Val Gln Pro Thr Ser Pro Ala Thr Ala
                260                 265                 270

Leu Arg Thr Pro Thr Leu Pro Glu Thr Met Ser Ser Pro Thr Ala
                275                 280                 285

Ala Ser Thr Thr His Arg Tyr Pro Lys Thr Pro Ser Pro Thr Val Ala
290                 295                 300

His Glu Ser Asn Trp Ala Lys Cys Glu Asp Leu Glu Thr Gln Thr Gln
305                 310                 315                 320

Ser Glu Lys Gln Leu Val Leu Asn Leu Thr Gly Asn Thr Leu Cys Ala
                325                 330                 335

Gly Gly Ala Ser Asp Glu Lys Leu Ile Ser Leu Ile Cys Arg Ala Val
                340                 345                 350

Lys Ala Thr Phe Asn Pro Ala Gln Asp Lys Cys Gly Ile Arg Leu Ala
                355                 360                 365

Ser Val Pro Gly Ser Gln Thr Val Val Lys Glu Ile Thr Ile His
370                 375                 380

Thr Lys Leu Pro Ala Lys Asp Val Tyr Glu Arg Leu Lys Asp Lys Trp
385                 390                 395                 400

Asp Glu Leu Lys Glu Ala Gly Val Ser Asp Met Lys Leu Gly Asp Gln
                405                 410                 415

Gly Pro Pro Glu Glu Ala Glu Asp Arg Phe Ser Met Pro Leu Ile Ile
                420                 425                 430

Thr Ile Val Cys Met Ala Ser Phe Leu Leu Leu Val Ala Ala Leu Tyr
                435                 440                 445

Gly Cys Cys His Gln Arg Leu Ser Gln Arg Lys Asp Gln Gln Arg Leu
                450                 455                 460

Thr Glu Glu Leu Gln Thr Val Glu Asn Gly Tyr His Asp Asn Pro Thr
465                 470                 475                 480
```

```
Leu Glu Val Met Glu Thr Ser Ser Glu Met Gln Lys Lys Val Val
                485                 490                 495

Ser Leu Asn Gly Glu Leu Gly Asp Ser Trp Ile Val Pro Leu Asp Asn
            500                 505                 510

Leu Thr Lys Asp Asp Leu Asp Glu Glu Asp Thr His Leu
        515                 520                 525

<210> SEQ ID NO 3
<211> LENGTH: 558
<212> TYPE: PRT
<213> ORGANISM: Homo sapiens

<400> SEQUENCE: 3

Met Arg Cys Ala Leu Ala Leu Ser Ala Leu Leu Leu Leu Ser Thr
1               5                   10                  15

Pro Pro Leu Leu Pro Ser Ser Pro Ser Pro Ser Pro Ser Gln
            20                  25                  30

Asn Ala Thr Gln Thr Thr Thr Asp Ser Ser Asn Lys Thr Ala Pro Thr
            35                  40                  45

Pro Ala Ser Ser Val Thr Ile Met Ala Thr Asp Thr Ala Gln Gln Ser
50                  55                  60

Thr Val Pro Thr Ser Lys Ala Asn Glu Ile Leu Ala Ser Val Lys Ala
65                  70                  75                  80

Thr Thr Leu Gly Val Ser Ser Asp Ser Pro Gly Thr Thr Leu Ala
                85                  90                  95

Gln Gln Val Ser Gly Pro Val Asn Thr Thr Val Ala Arg Gly Gly Gly
                100                 105                 110

Ser Gly Asn Pro Thr Thr Thr Ile Glu Ser Pro Lys Ser Thr Lys Ser
            115                 120                 125

Ala Asp Thr Thr Thr Val Ala Thr Ser Thr Ala Thr Ala Lys Pro Asn
        130                 135                 140

Thr Thr Ser Ser Gln Asn Gly Ala Glu Asp Thr Thr Asn Ser Gly Gly
145                 150                 155                 160

Lys Ser Ser His Ser Val Thr Thr Asp Leu Thr Ser Thr Lys Ala Glu
                165                 170                 175

His Leu Thr Thr Pro His Pro Thr Ser Pro Leu Ser Pro Arg Gln Pro
            180                 185                 190

Thr Ser Thr His Pro Val Ala Thr Pro Thr Ser Ser Gly His Asp His
        195                 200                 205

Leu Met Lys Ile Ser Ser Ser Ser Thr Val Ala Ile Pro Gly Tyr
    210                 215                 220

Thr Phe Thr Ser Pro Gly Met Thr Thr Thr Leu Leu Glu Thr Val Phe
225                 230                 235                 240

His His Val Ser Gln Ala Gly Leu Glu Leu Leu Thr Ser Gly Asp Leu
                245                 250                 255

Pro Thr Leu Ala Ser Gln Ser Ala Gly Ile Thr Ala Ser Ser Val Ile
            260                 265                 270

Ser Gln Arg Thr Gln Gln Thr Ser Ser Gln Met Pro Ala Ser Ser Thr
        275                 280                 285

Ala Pro Ser Ser Gln Glu Thr Val Gln Pro Thr Pro Ala Thr Ala
    290                 295                 300

Leu Arg Thr Pro Thr Leu Pro Glu Thr Met Ser Ser Ser Pro Thr Ala
305                 310                 315                 320

Ala Ser Thr Thr His Arg Tyr Pro Lys Thr Pro Ser Pro Thr Val Ala
```

|  | 325 |  |  | 330 |  |  | 335 |  |
|---|---|---|---|---|---|---|---|---|

His Glu Ser Asn Trp Ala Lys Cys Glu Asp Leu Glu Thr Gln Thr Gln
                340                 345                 350

Ser Glu Lys Gln Leu Val Leu Asn Leu Thr Gly Asn Thr Leu Cys Ala
            355                 360                 365

Gly Gly Ala Ser Asp Glu Lys Leu Ile Ser Leu Ile Cys Arg Ala Val
        370                 375                 380

Lys Ala Thr Phe Asn Pro Ala Gln Asp Lys Cys Gly Ile Arg Leu Ala
385                 390                 395                 400

Ser Val Pro Gly Ser Gln Thr Val Val Lys Glu Ile Thr Ile His
                405                 410                 415

Thr Lys Leu Pro Ala Lys Asp Val Tyr Glu Arg Leu Lys Asp Lys Trp
            420                 425                 430

Asp Glu Leu Lys Glu Ala Gly Val Ser Asp Met Lys Leu Gly Asp Gln
        435                 440                 445

Gly Pro Pro Glu Glu Ala Glu Asp Arg Phe Ser Met Pro Leu Ile Ile
    450                 455                 460

Thr Ile Val Cys Met Ala Ser Phe Leu Leu Leu Val Ala Ala Leu Tyr
465                 470                 475                 480

Gly Cys Cys His Gln Arg Leu Ser Gln Arg Lys Asp Gln Gln Arg Leu
                485                 490                 495

Thr Glu Glu Leu Gln Thr Val Glu Asn Gly Tyr His Asp Asn Pro Thr
            500                 505                 510

Leu Glu Val Met Glu Thr Ser Ser Glu Met Gln Glu Lys Lys Val Val
        515                 520                 525

Ser Leu Asn Gly Glu Leu Gly Asp Ser Trp Ile Val Pro Leu Asp Asn
    530                 535                 540

Leu Thr Lys Asp Asp Leu Asp Glu Glu Glu Asp Thr His Leu
545                 550                 555

<210> SEQ ID NO 4
<211> LENGTH: 1581
<212> TYPE: DNA
<213> ORGANISM: Homo sapiens

<400> SEQUENCE: 4

| atgcgctgcg cgctggcgct ctcggcgctg ctgctactgt tgtcaacgcc gccgctgctg | 60 |
| ccgtcgtcgc cgtcgccgtc gccgtcgccc tcccagaatg caacccagac tactacggac | 120 |
| tcatctaaca aaacagcacc gactccagca tccagtgtca ccatcatggc tacagataca | 180 |
| gcccagcaga gcacagtccc cacttccaag gccaacgaaa tcttggcctc ggtcaaggcg | 240 |
| accacccttg gtgtatccag tgactcaccg gggactacaa ccctggctca gcaagtctca | 300 |
| ggcccagtca cactaccgt ggctagagga ggcggctcag gcaaccctac taccaccatc | 360 |
| gagagcccca gagcacaaa aagtgcagac accactacag ttgcaaccct cacagccaca | 420 |
| gctaaaccta caccacaag cagccagaat ggagcagaag atacaacaaa ctctgggggg | 480 |
| aaaagcagcc acagtgtgac cacagacctc acatccacta aggcagaaca tctgacgacc | 540 |
| cctcacccta caagtccact tagccccga caacccactt cgacgcatcc tgtggccacc | 600 |
| ccaacaagct cgggacatga ccatcttatg aaaatttcaa gcagttcaag cactgtggct | 660 |
| atccctggct acaccttcac aagcccgggg atgaccacca ccctaccgtc atcggttatc | 720 |
| tcgcaaagaa ctcaacagac ctccagtcag atgccagcca gctctacggc cccttcctcc | 780 |
| caggagacag tgcagcccac gagcccggca acggcattga gaacacctac cctgccagag | 840 |

-continued

| | |
|---|---|
| accatgagct ccagccccac agcagcatca actacccacc gatacccaa aacaccttct | 900 |
| cccactgtgg ctcatgagag taactgggca aagtgtgagg atcttgagac acagacacag | 960 |
| agtgagaagc agctcgtcct gaacctcaca ggaaacaccc tctgtgcagg gggcgcttcg | 1020 |
| gatgagaaat tgatctcact gatatgccga gcagtcaaag ccaccttcaa cccggcccaa | 1080 |
| gataagtgcg gcatacggct ggcatctgtt ccaggaagtc agaccgtggt cgtcaaagaa | 1140 |
| atcactattc acactaagct ccctgccaag gatgtgtacg agcggctgaa ggacaaatgg | 1200 |
| gatgaactaa aggaggcagg ggtcagtgac atgaagctag gggaccaggg gccaccggag | 1260 |
| gaggccgagg accgcttcag catgcccctc atcatcacca tcgtctgcat ggcatcattc | 1320 |
| ctgctcctcg tggcggccct ctatggctgc tgccaccagc gcctctccca gaggaaggac | 1380 |
| cagcagcggc taacagagga gctgcagaca gtggagaatg gttaccatga caacccaaca | 1440 |
| ctggaagtga tggagacctc ttctgagatg caggagaaga aggtggtcag cctcaacggg | 1500 |
| gagctggggg acagctggat cgtccctctg gacaacctga ccaaggacga cctggatgag | 1560 |
| gaggaagaca cacacctcta g | 1581 |

<210> SEQ ID NO 5
<211> LENGTH: 1677
<212> TYPE: DNA
<213> ORGANISM: Homo sapiens

<400> SEQUENCE: 5

| | |
|---|---|
| atgcgctgcg cgctggcgct ctcggcgctg ctgctactgt tgtcaacgcc gccgctgctg | 60 |
| ccgtcgtcgc cgtcgccgtc gccgtcgccc tcccagaatg caacccagac tactacggac | 120 |
| tcatctaaca aaacagcacc gactccagca tccagtgtca ccatcatggc tacagataca | 180 |
| gcccagcaga gcacagtccc cacttccaag gccaacgaaa tcttggcctc ggtcaaggcg | 240 |
| accacccttg tgtatccag tgactcaccg gggactacaa ccctggctca gcaagtctca | 300 |
| ggcccagtca acactaccgt ggctagagga ggcggctcag gcaaccctac taccaccatc | 360 |
| gagagcccca agagcacaaa aagtgcagac accactacag ttgcaacctc cacagccaca | 420 |
| gctaaaccta cacacacaag cagccagaat ggagcagaag atacaacaaa ctctgggggg | 480 |
| aaaagcagcc acagtgtgac cacagacctc acatccacta aggcagaaca tctgacgacc | 540 |
| cctcacccta caagtccact tagccccga caacccactt cgacgcatcc tgtgccacc | 600 |
| ccaacaagct cgggacatga ccatcttatg aaaatttcaa gcagttcaag cactgtggct | 660 |
| atccctggct acaccttcac aagcccgggg atgaccacca ccctactaga acagtgttt | 720 |
| caccatgtca gccaggctgg tcttgaactc ctgacctcgg tgatctgcc caccttggcc | 780 |
| tcccaaagtg ctgggattac agcgtcatcg gttatctcgc aaagaactca acagacctcc | 840 |
| agtcagatgc cagccagctc tacggcccct tcctcccagg agacagtgca gcccacgagc | 900 |
| ccggcaacgg cattgagaac acctaccctg ccagagacca tgagctccag ccccacagca | 960 |
| gcatcaacta cccaccgata ccccaaaaca ccttctccca ctgtggctca tgagagtaac | 1020 |
| tgggcaaagt gtgaggatct tgagacacag acacagagtg agaagcagct cgtcctgaac | 1080 |
| ctcacaggaa cacctctg tgcaggggc gcttcggatg agaaattgat ctcactgata | 1140 |
| tgccgagcag tcaaagccac cttcaacccg gcccaagata agtgcggcat acggctggca | 1200 |
| tctgttccag gaagtcagac cgtggtcgtc aaagaaatca ctattcacac taagctccct | 1260 |
| gccaaggatg tgtacgagcg gctgaaggac aaatgggatg aactaaagga ggcagggtc | 1320 |

-continued

```
agtgacatga agctagggga ccaggggcca ccggaggagg ccgaggaccg cttcagcatg    1380
cccctcatca tcaccatcgt ctgcatggca tcattcctgc tcctcgtggc ggccctctat    1440
ggctgctgcc accagcgcct ctcccagagg aaggaccagc agcggctaac agaggagctg    1500
cagacagtgg agaatggtta ccatgacaac ccaacactgg aagtgatgga gacctcttct    1560
gagatgcagg agaagaaggt ggtcagcctc aacggggagc tggggacag ctggatcgtc     1620 cctctggaca acctgaccaa ggacgacctg gatgaggagg aagacacaca cctctag       1677
```

<210> SEQ ID NO 6
<211> LENGTH: 407
<212> TYPE: PRT
<213> ORGANISM: Homo sapiens

<400> SEQUENCE: 6

```
Ser Pro Ser Pro Ser Pro Ser Pro Ser Gln Asn Ala Thr Gln Thr Thr
1               5                   10                  15

Thr Asp Ser Ser Asn Lys Thr Ala Pro Thr Pro Ala Ser Ser Val Thr
            20                  25                  30

Ile Met Ala Thr Asp Thr Ala Gln Gln Ser Thr Val Pro Thr Ser Lys
        35                  40                  45

Ala Asn Glu Ile Leu Ala Ser Val Lys Ala Thr Thr Leu Gly Val Ser
    50                  55                  60

Ser Asp Ser Pro Gly Thr Thr Leu Ala Gln Gln Val Ser Gly Pro
65                  70                  75                  80

Val Asn Thr Thr Val Ala Arg Gly Gly Gly Ser Gly Asn Pro Thr Thr
                85                  90                  95

Thr Ile Glu Ser Pro Lys Ser Thr Lys Ser Ala Asp Thr Thr Thr Val
            100                 105                 110

Ala Thr Ser Thr Ala Thr Ala Lys Pro Asn Thr Thr Ser Ser Gln Asn
        115                 120                 125

Gly Ala Glu Asp Thr Thr Asn Ser Gly Gly Lys Ser Ser His Ser Val
    130                 135                 140

Thr Thr Asp Leu Thr Ser Thr Lys Ala Glu His Leu Thr Thr Pro His
145                 150                 155                 160

Pro Thr Ser Pro Leu Ser Pro Arg Gln Pro Thr Ser His Pro Val
                165                 170                 175

Ala Thr Pro Thr Ser Ser Gly His Asp His Leu Met Lys Ile Ser Ser
            180                 185                 190

Ser Ser Ser Thr Val Ala Ile Pro Gly Tyr Thr Phe Thr Ser Pro Gly
        195                 200                 205

Met Thr Thr Thr Leu Pro Ser Ser Val Ile Ser Gln Arg Thr Gln Gln
    210                 215                 220

Thr Ser Ser Gln Met Pro Ala Ser Ser Thr Ala Pro Ser Ser Gln Glu
225                 230                 235                 240

Thr Val Gln Pro Thr Ser Pro Ala Thr Ala Leu Arg Thr Pro Thr Leu
                245                 250                 255

Pro Glu Thr Met Ser Ser Ser Pro Thr Ala Ala Ser Thr Thr His Arg
            260                 265                 270

Tyr Pro Lys Thr Pro Ser Pro Val Ala His Glu Ser Asn Trp Ala
        275                 280                 285

Lys Cys Glu Asp Leu Glu Thr Gln Thr Gln Ser Glu Lys Gln Leu Val
    290                 295                 300

Leu Asn Leu Thr Gly Asn Thr Leu Cys Ala Gly Gly Ala Ser Asp Glu
305                 310                 315                 320
```

```
Lys Leu Ile Ser Leu Ile Cys Arg Ala Val Lys Ala Thr Phe Asn Pro
                325                 330                 335

Ala Gln Asp Lys Cys Gly Ile Arg Leu Ala Ser Val Pro Gly Ser Gln
            340                 345                 350

Thr Val Val Lys Glu Ile Thr Ile His Thr Lys Leu Pro Ala Lys
        355                 360                 365

Asp Val Tyr Glu Arg Leu Lys Asp Lys Trp Asp Glu Leu Lys Glu Ala
370                 375                 380

Gly Val Ser Asp Met Lys Leu Gly Asp Gln Gly Pro Pro Glu Glu Ala
385                 390                 395                 400

Glu Asp Arg Phe Ser Met Pro
                405

<210> SEQ ID NO 7
<211> LENGTH: 439
<212> TYPE: PRT
<213> ORGANISM: Homo sapiens

<400> SEQUENCE: 7

Ser Pro Ser Pro Ser Pro Ser Gln Asn Ala Thr Gln Thr Thr
1               5                   10                  15

Thr Asp Ser Ser Asn Lys Thr Ala Pro Thr Pro Ala Ser Ser Val Thr
            20                  25                  30

Ile Met Ala Thr Asp Thr Ala Gln Gln Ser Thr Val Pro Thr Ser Lys
        35                  40                  45

Ala Asn Glu Ile Leu Ala Ser Val Lys Ala Thr Thr Leu Gly Val Ser
    50                  55                  60

Ser Asp Ser Pro Gly Thr Thr Thr Leu Ala Gln Gln Val Ser Gly Pro
65                  70                  75                  80

Val Asn Thr Thr Val Ala Arg Gly Gly Gly Ser Gly Asn Pro Thr Thr
                85                  90                  95

Thr Ile Glu Ser Pro Lys Ser Thr Lys Ser Ala Asp Thr Thr Thr Val
            100                 105                 110

Ala Thr Ser Thr Ala Thr Ala Lys Pro Asn Thr Thr Ser Ser Gln Asn
        115                 120                 125

Gly Ala Glu Asp Thr Thr Asn Ser Gly Gly Lys Ser Ser His Ser Val
    130                 135                 140

Thr Thr Asp Leu Thr Ser Thr Lys Ala Glu His Leu Thr Thr Pro His
145                 150                 155                 160

Pro Thr Ser Pro Leu Ser Pro Arg Gln Pro Thr Ser Thr His Pro Val
                165                 170                 175

Ala Thr Pro Thr Ser Ser Gly His Asp His Leu Met Lys Ile Ser Ser
            180                 185                 190

Ser Ser Ser Thr Val Ala Ile Pro Gly Tyr Thr Phe Thr Ser Pro Gly
        195                 200                 205

Met Thr Thr Thr Leu Leu Glu Thr Val Phe His His Val Ser Gln Ala
    210                 215                 220

Gly Leu Glu Leu Leu Thr Ser Gly Asp Leu Pro Thr Leu Ala Ser Gln
225                 230                 235                 240

Ser Ala Gly Ile Thr Ala Ser Ser Val Ile Ser Gln Arg Thr Gln Gln
                245                 250                 255

Thr Ser Ser Gln Met Pro Ala Ser Ser Thr Ala Pro Ser Ser Gln Glu
            260                 265                 270

Thr Val Gln Pro Thr Ser Pro Ala Thr Ala Leu Arg Thr Pro Thr Leu
```

|  |  |  | 275 |  |  |  | 280 |  |  |  | 285 |  |  |
|--|--|--|--|--|--|--|--|--|--|--|--|--|--|

Pro Glu Thr Met Ser Ser Ser Pro Thr Ala Ala Ser Thr Thr His Arg
  290                          295                        300

Tyr Pro Lys Thr Pro Ser Pro Thr Val Ala His Glu Ser Asn Trp Ala
305                        310                      315                  320

Lys Cys Glu Asp Leu Glu Thr Gln Thr Gln Ser Glu Lys Gln Leu Val
                      325                      330                      335

Leu Asn Leu Thr Gly Asn Thr Leu Cys Ala Gly Gly Ala Ser Asp Glu
           340                      345                      350

Lys Leu Ile Ser Leu Ile Cys Arg Ala Val Lys Ala Thr Phe Asn Pro
                355                  360                  365

Ala Gln Asp Lys Cys Gly Ile Arg Leu Ala Ser Val Pro Gly Ser Gln
    370                      375                      380

Thr Val Val Val Lys Glu Ile Thr Ile His Thr Lys Leu Pro Ala Lys
385                        390                      395                  400

Asp Val Tyr Glu Arg Leu Lys Asp Lys Trp Asp Glu Leu Lys Glu Ala
                    405                      410                  415

Gly Val Ser Asp Met Lys Leu Gly Asp Gln Gly Pro Pro Glu Glu Ala
        420                      425                      430

Glu Asp Arg Phe Ser Met Pro
              435

```
<210> SEQ ID NO 8
<211> LENGTH: 18
<212> TYPE: DNA
<213> ORGANISM: Homo sapiens

<400> SEQUENCE: 8
ctgccagaga ccatgagc                                                  18

<210> SEQ ID NO 9
<211> LENGTH: 20
<212> TYPE: DNA
<213> ORGANISM: Homo sapiens

<400> SEQUENCE: 9
gtcccctagc ttcatgtcac                                                20

<210> SEQ ID NO 10
<211> LENGTH: 10
<212> TYPE: PRT
<213> ORGANISM: Homo sapiens

<400> SEQUENCE: 10
```

Ala Ala Ser Thr Thr His Arg Tyr Pro Lys
1               5                   10

```
<210> SEQ ID NO 11
<211> LENGTH: 10
<212> TYPE: PRT
<213> ORGANISM: Homo sapiens

<400> SEQUENCE: 11
```

Thr Pro Ser Pro Thr Val Ala His Glu Ser
1               5                   10

```
<210> SEQ ID NO 12
<211> LENGTH: 5
<212> TYPE: PRT
<213> ORGANISM: Homo sapiens
```

```
<400> SEQUENCE: 12

Gln Thr Gln Ser Glu
1               5

<210> SEQ ID NO 13
<211> LENGTH: 15
<212> TYPE: PRT
<213> ORGANISM: Homo sapiens

<400> SEQUENCE: 13

Cys Gly Ile Arg Leu Ala Ser Val Pro Gly Ser Gln Thr Val Val
1               5                   10                  15

<210> SEQ ID NO 14
<211> LENGTH: 15
<212> TYPE: PRT
<213> ORGANISM: Homo sapiens

<400> SEQUENCE: 14

Ile His Thr Lys Leu Pro Ala Lys Asp Val Tyr Glu Arg Leu Lys
1               5                   10                  15

<210> SEQ ID NO 15
<211> LENGTH: 15
<212> TYPE: PRT
<213> ORGANISM: Homo sapiens

<400> SEQUENCE: 15

Asp Lys Trp Asp Glu Leu Lys Glu Ala Gly Val Ser Asp Met Lys
1               5                   10                  15

<210> SEQ ID NO 16
<211> LENGTH: 15
<212> TYPE: PRT
<213> ORGANISM: Homo sapiens

<400> SEQUENCE: 16

Ala Ala Ser Thr Thr His Arg Tyr Pro Lys Thr Pro Ser Pro Thr
1               5                   10                  15

<210> SEQ ID NO 17
<211> LENGTH: 15
<212> TYPE: PRT
<213> ORGANISM: Homo sapiens

<400> SEQUENCE: 17

Asn Trp Ala Lys Cys Glu Asp Leu Glu Thr Gln Thr Gln Ser Glu
1               5                   10                  15

<210> SEQ ID NO 18
<211> LENGTH: 15
<212> TYPE: PRT
<213> ORGANISM: Homo sapiens

<400> SEQUENCE: 18

Tyr Glu Arg Leu Lys Asp Lys Trp Asp Glu Leu Lys Glu Ala Gly
1               5                   10                  15

<210> SEQ ID NO 19
<211> LENGTH: 55
<212> TYPE: PRT
<213> ORGANISM: Homo sapiens

<400> SEQUENCE: 19
```

```
Lys Glu Ala Gly Val Ser Asp Met Lys Leu Gly Asp Gln Gly Pro Pro
1               5                   10                  15

Glu Glu Ala Glu Asp Arg Phe Ser Met Pro Leu Ile Ile Thr Ile Val
                20                  25                  30

Cys Met Ala Ser Phe Leu Leu Leu Val Ala Ala Leu Tyr Gly Cys Cys
            35                  40                  45

His Gln Arg Leu Ser Gln Arg
    50                  55

<210> SEQ ID NO 20
<211> LENGTH: 15
<212> TYPE: PRT
<213> ORGANISM: Homo sapiens

<400> SEQUENCE: 20

Asp Asn Leu Thr Lys Asp Asp Leu Asp Glu Glu Asp Thr His
1               5                   10                  15
```